US008728470B2

(12) United States Patent
Fox et al.

(10) Patent No.: US 8,728,470 B2
(45) Date of Patent: May 20, 2014

(54) CAB MOLECULES

(75) Inventors: Judith A. Fox, San Francisco, CA (US); Fiona A. Harding, Santa Clara, CA (US); Rashid M. Harunur, Sunnyvale, CA (US); Volker Schellenberger, Palo Alto, CA (US)

(73) Assignee: Danisco US Inc., Palo Alto, CA (US)

( * ) Notice: Subject to any disclaimer, the term of this patent is extended or adjusted under 35 U.S.C. 154(b) by 191 days.

(21) Appl. No.: 13/287,642

(22) Filed: Nov. 2, 2011

(65) Prior Publication Data
US 2012/0107314 A1 May 3, 2012

Related U.S. Application Data

(62) Division of application No. 10/590,870, filed as application No. PCT/US2005/012270 on Apr. 12, 2005, now Pat. No. 8,088,609.

(60) Provisional application No. 60/562,386, filed on Apr. 15, 2004, provisional application No. 60/636,002, filed on Dec. 14, 2004.

(51) Int. Cl.
*A61K 39/395* (2006.01)
*C07K 16/00* (2006.01)

(52) U.S. Cl.
USPC .................................. 424/134.1; 435/188.5

(58) Field of Classification Search
CPC ...................... A61K 2039/505; C07K 16/3007
USPC ...................................... 424/178.1; 435/188.5
See application file for complete search history.

(56) References Cited

U.S. PATENT DOCUMENTS

| | | | |
|---|---|---|---|
| 4,458,066 A | 7/1984 | Caruthers et al. | 536/27 |
| 4,522,811 A | 6/1985 | Eppstein et al. | 514/2 |
| 4,675,187 A | 6/1987 | Konishi et al. | 424/117 |
| 4,711,845 A | 12/1987 | Gelfand et al. | 435/68 |
| 4,975,278 A | 12/1990 | Senter et al. | 424/94.3 |
| 5,711,944 A | 1/1998 | Gilbert et al. | 424/85.7 |
| 5,766,883 A | 6/1998 | Ballance et al. | 435/69.7 |
| 5,773,435 A | 6/1998 | Kadow et al. | 540/222 |
| 5,843,440 A | 12/1998 | Pouletty et al. | 424/133.1 |
| 6,537,988 B2 | 3/2003 | Lee | 514/221 |
| 6,835,550 B1 | 12/2004 | Estell et al. | 435/7.24 |
| 2003/0068792 A1 | 4/2003 | Chen et al. | 435/6 |
| 2003/0100467 A1 | 5/2003 | Aehle et al. | 510/392 |
| 2003/0147874 A1 | 8/2003 | Schellenberger | 424/94.1 |

FOREIGN PATENT DOCUMENTS

| | | |
|---|---|---|
| EP | 0 196 864 | 10/1996 |
| WO | WO 91/01990 | 2/1991 |
| WO | WO 00/24782 | 5/2000 |
| WO | WO 02/47717 A2 | 6/2002 |
| WO | WO 03/055527 A2 | 12/2002 |
| WO | WO 03/105757 A2 | 12/2003 |
| WO | WO 2005/058236 A2 | 6/2005 |

OTHER PUBLICATIONS

Garrett et al Europian J. of cancer 1999, 35, 2010-2030.*
Altschul et al., "Basic Local Alignment Search Tool," *J. of Molecular Biology*, vol. 215, pp. 403-410, 1990.
Altschul et al., "Gapped BLAST and PSI-BLAST: a new generation of protein database search programs," *Nucleic Acids Res.*, vol. 25, No. 17, pp. 3389-3402, 1997.
Ausubel et al., eds., *Current Protocols in Molecular Biology*, vol. I, Green Publishing Associates, Inc. and John Wiley & Sons, Inc., New York, p. 2.10.1-16 (1989).
Bagshawe et al., "Developments with targeted enzymes in cancer therapy," *Current Opinion in Immunology*, vol. 11, pp. 579-583, 1999.
Beaucage et al., "Deoxynucleoside Phosphoramidites—A new Class of Key Intermediates for Deoxypolynucleotide Synthesis," *Tetrahedron Lett.*, vol. 22, pp. 1859-1862, 1981.
Benito et al, "Insertion of a 27 amino acid viral peptide in different zones of *Escherichia coli* β-galactosidase: Effect on the enzyme activity," *FEMS Microbiology Letters*, vol. 123, pp. 107-112, 1994.
Bolivar et al., "Construction and Characterization of New Cloning Vehicles, " *Gene*, vol. 2, pp. 95-113, 1977.
Broach, J.R., "Construction of High Copy Yeast Vectors using 2-μm Circle Sequences," *Meth. In Enzymology*, vol. 101, pp. 307-324, 1983.
Brown et al., "Chemical Synthesis and Cloning of a Tyrosine tRNA Gene," *Meth. Enzymol.*, vol. 68, pp. 109-151, 1979.
Christofidou-Solomidou et al., "Immunotargeting of glucosooxidase to endothelium in vivo causes oxidative vascular injury in the lungs," *Am. J. Physiol. Lung Cell. Mol. Physiol.*, vol. 278, pp. L794-L805, 2000.
Clarke et al., "Selection Procedure for isolation of Centromere DNAs from *Saccharomyces cerevisiae*," *Meth.In Enz.*, vol. 101, pp. 300-307, 1983.
Clewell et al., "Supercoiled Circular Dna-Protein Complex in *Escherichia Coli*: Purification and Induced Conversion to an Open Circular DNA Form," *Proc. Natl. Acad. Sci. USA*, vol. 62, pp. 1159-1166, 1969.
Clewell, J., "Nature of col. $E_1$ Plasmid Replication in *Escherichia coli* in the Presence of Chloramphenicol," *Bacteriol.*, vol. 110, pp. 667-675, 1972.
Cohen et al., "Nonchromosomal Antibiotic Resistance in Bacteria: Genetic Transformation of *Escherichia coil* by R-Factor DNA," *Proc. Natl. Acad. Sci. USA*, vol. 69, pp. 2110-2114, 1972.
Denny, "Prodrug strategies in Cancer Therapy", *Eur. J. Med. Chem.*, 36:577-95 (2001).
Depicker et al., "Nopaline synthase: Transcript Mapping and DNA Sequence," *J. Mol. Appl. Gen.*, vol. 1, pp. 561-573, 1982.

(Continued)

*Primary Examiner* — Tekchand Saidha
*Assistant Examiner* — Md. Younus Meah
(74) *Attorney, Agent, or Firm* — Danisco US Inc.

(57) ABSTRACT

The present invention relates to CAB molecules, ADEPT constructs directed against CEA, and their use in therapy.

20 Claims, 39 Drawing Sheets

(56) References Cited

OTHER PUBLICATIONS

Fiers et al., "Complete nucleotide sequence of SV40 DNA," *Nature*, vol. 273, pp. 113-120, 1978.
Gold et al., "Demonstration of Tumor-Specific antigens in human colonic carcinomata by immunological tolerance and absorption techniques ", *J. Exp. Med.*, 121:439-462 (1965).
Goeddel et al., "Synthesis of human fibroblast interferon by *E. Coli,*" *Nuc. Acids Res.*, vol. 8, pp. 4057- 4075, 1980.
Goodchild,J., "Conjugates of Oligonucleotides and Modified Oligonucleotides: A Review of Their Synthesis and Properties," *Bioconjugate Chemistry*, vol. 1, No. 3, pp. 165-187, 1990.
Harding, F.A., et al., "A β-lactamase with reduced immunogenicity for the targeted delivery of chemotherapeutics using antibody-directed enzyme prodrug therapy." *Molecular Cancer Therapeutics* 4(11): 1791-1800, (2005).
Hefta et al., "Kinetic and affinity constants of epitope specific anti-carcinoembryonic antigen (CEA) monoclonal antibodies for CEA and engineered CEA domain constructs," *Immunotechnology*, 4:49-57, (1998).
Hess et al., "Cooperation of Glycolytic Enzymes," *J. Adv. Enzyme Reg.*, vol. 7, pp. 149-167, 1968.
Hitzeman et al., "Isolation and Characterization of the Yeast 3-Phosphoglycerokinase Gene (PGK) by an Immunological Screening Technique," *J. Biol. Chem.*, 255:2073 (1980).
Holland et al., "Isolation and Identification of Yeast Messenger Ribonucleic Acids Coding for Enolase, Glyceraldehyde-3-phosphate Dehydrogenase, and Phosphoglycerate Kinase," *Biochemistry*, vol. 17, pp. 4900-4907, 1978.
Holland et al., The Primary Structures of Two Yeast Enolase Genes, *J. Biol. Chem.*, vol. 256, No. 3, pp. 1385-1395, 1981.
Houghton et al., "Mouse monoclonal IgG3 antibody detecting GD3 ganglioside: A phase 1 trial in patients with malignant melanoma", *Proc. Natl. Acad. Sci. USA*, 82:1242-1246 (1985).
Hsiao et al., "High-Frequency transformation of yeast by plasmids containing the cloned yeast ARG4gene," *Proc. Natl. Acad. Sci. USA*, vol. 76, No. 8,pp. 3829-3833, 1979.
Kerr et al., "Development and Activitires of a New Melphalan Prodrug Designed for Tumor-Selective Activation ", *Bioconjugate Chem.*, 9:255-259 (1998).
Levy et al., "Biological and clinical implications of lymphocyte hybridomas: Tumor therapy with monoclonal antibodies,", *Ann. Rev. Med.*, 34:107-116 (1983).
Margolin et al., "Substrate Specificity of Penicillin Smidase From *E. coli*," *Biochim. Biophys. Acta.*, vol. 616, pp. 283-289, 1980.
Maxam et al., Sequencing End-Labeled DNA with Base-Specific Chemical Cleavages, *Methods in Enzymology*, vol. 65, pp. 499-560, 1980.
McDonagh et al., Improved Yield and Stability of L49-sFv-beta-Lactamase a Single-Chain Antibody Fusion Protein for Anticancer Prodrug Activation, by Protein Engineering, *Bioconjugate Chem.*, 14, 860-869, 2003.
Messing et al., "A system for shotgun DNA sequencing," *Nuc. Acids Res.*, vol. 9, pp. 309-321, 1981.
Meyer et al., "Site-Specific Prodrug Activation by Antibody-beta-Lactamase Conjugates: Preclincial Investigation of the Efficacy and Toxicity of Doxorubicin Delivered by Antibody Directed Catalysis," *American Chemical Society*, V.6, N. 4 pp. 440-446, (1995).
Miller et al., "An Insect Baculovirus Host-Vector System for High-Level Expression of Foreign Genes," *Genetic Engineering*, 1986, Setlow et al., Eds., Plenum Publishing, vol. 8, pp. 227-297.
Napier et al., "Antibody-directed Enzyme Prodrug Therapy: Efficacy and Mechanism of Action in Colorectal Carcinoma", *Clin. Cancer Res.*, 6:765-772 (2000).
Napolitano et al., "Glubodies: randomized libraries of glutathione transferase enzymes," *Chem. Biol.*, vol. 3, pp. 359-367, 1996.
Narang et al., "Improved Phosphotriester Method for the Synthesis of Gene Fragments," *Meth. In Enzymol.*, vol. 68, pp. 90-99, 1979.

Neumaier et al., "Cloning of the Genes for T84.66, an antibody that has a high specificity and affinity for carcinoembryonic antigen, and expression of chimeric human/mouse T84.66 genes in myeloma and Chinese hamster ovary cells,", *Cancer Research*, 50:2128-2134 (1990).
Niculescu-Duvaz et al., "Prodrugs for antibody- and gene-directed enzyme prodrug therapies (ADEPT and GDEPT)," *Anticancer Drug Des.*, vol. 14, pp. 517-538, 1999.
Sambrook et al, Eds. *Molecular Cloning: A Laboratory Manual*, 2d Ed., Cold Spring Harbor Laboratory Press, pp. 9.47-9.57, and Chapter 15.51, 1989.
Sanger et al., "DNA sequencing with chain-terminating inhibitors," *Proc. Natl. Acad. Sci. USA*, vol. 74, No. 12, pp. 5463-5467, 1977.
Sears et al., "Effects of Monoclonal Antibody Immunotherapy on Patients with Gastrointestinal Adenocarcinoma", *J. Biol. Resp. Modifiers*, 3:138-150 (1984).
Shaw et al., "A general method for the transfer of cloned genes to plant cells," *Gene*, vol. 23, pp. 315-330, 1983.
Shimatake et al., Purified a regulatory protein cll positively activates promoters for lysogenic development, Nature, vol. 292, pp. 128-132 1981.
Smith et al., "Protein Loop Grafting to Construct a Variant of Tissue-type Plasminogen Activator that Binds Platelet Integrin alpha IIb beta3 ", *J. Biol. Chem.*, 270:30486 (1995).
Smith et al., "Toward Antibody-directed Enzyme Prodrug Therapy with the T268G Mutant of Human Carboxypeptidase A1 and Novel in Vivo Stable Prodrugs of Methotrexate", *J. Biol. Chem.*, 272:15804-15816 (1997).
Solingen et al., "Fusion of Yeast Spheroplasts ", *J. Bact.*, 130:2, pp. 946-947 (1977).
Stella et al., "Prodrugs: A Chemical Approach to Targeted Drug Delivery," *Directed Drug Delivery*, R. Borchardt et al, Eds., pp. 247-267, Humana Press, 1985.
Stickler, M., et al., "CD4+ T-Cell Epitope Determination Using Unexposed Human Donor Peripheral Blood Mononuclear Cells." *J. Immunotherapy* 23(6): 654-660, (2000).
Stickler, M. et al., "Human Population-based Identification of CD4+ T-Cell Peptide Epitope Determinants," *Journal of Immunological Methods*, 281:95-108 (2003).
Stinchcomb et al., "Isolation and characterization of a yeat chromosomal replicator," *Nature*, vol. 282, pp. 39-43, 1979.
Thomson et al., "Version 2000: the new beta-lactamases of Gram-negative bacteria at the dawn of the new millenium", *Microbes and Infection*, 2:1225-1235 (2000).
Tschumper et al., Sequence of a yeast DNA fragment containing a chromosomal replicator and the TRP1 gene, *Gene*, vol. 10, 157-166, 1980.
Trouet et al., "A covalent linkage between daunorubicin and proteins that is stable in serum and reversible by lysosomal hydrolases, as required for a lysosomotropic drug-carrier conjugate: in vitro and in vivo studies," *Proc. Natl. Acad. Sci. USA*, vol. 79, pp. 626-629, 1982.
Umemoto et al., "Preparation and invitro cytotoxicity of a methotrexate-anit-MM46 monoclonal antibody conjugate via an oligopeptide spacer,", *Int. J. Cancer*, 43:677 (1989).
Wilman, "Prodrugs in Cancer Chemotherapy," *biochemical society Transactions*, 14:375-382 (615th Meeting Belfast 1986).
Wu et al., Tumor localization of anti-CEA single-chain Fvs: improved targeting by non-covalent dimers, *Immunotechnology*, V2, pp. 21-36, 1996.
Xu et al., "Strategies for Enzyme/Prodrug Cancer Therapy", *Clinical. Cancer Res.*, 7:3314-3324 (2001).
International Search Report for PCT Application No. PCT/US2005/012270 dated May 18, 2006.
International Preliminary Report on Patentability for Oct. 19, 2006 International Application No. PCT/US2005/12270 dated Oct. 19, 2006.
Written Opinion of the International Searching Authority for International Application No. PCT/US2005/12270 dated May 18, 2006.

\* cited by examiner

```
  1 DIVLTQSPAS LAVSLGQRAT MSCRAGESVD IFGVGFLHWY QQKPGQPPKL
 51 LIYRASNLES GIPVRFSGTG SRTDFTLIID PVEADDVATY YCQQTNEDPY
101 TFGGGTKLEI KGGGGSGGGG SGGGGSGGGG SGGGGSGGGG SEVQLQQSGA
151 ELVEPGASVK LSCTASGFNI KDTYMHWVKQ RPEQGLEWIG RIDPANGNSK
201 YVPKFQGKAT ITADTSSNTA YLQLTSLTSE DTAVYYCAPF GYYVSDYAMA
251 YWGQGTSVTV SS (SEQ ID NO:1)
```

FIG._1A

```
  1 GACATCGTCC TGACCCAGAG CCCGGCAAGC CTGGCTGTTT CCCTGGGCCA
 51 GCGTGCCACT ATGTCCTGCA GAGCGGGTGA GTCTGTTGAC ATTTTCGGTG
101 TCGGTTTTCT GCACTGGTAC AACAGAAAC  CGGGTCAGCC GCCAAAACTG
151 CTGATCTATC GTGCTTCTAA CCTGGAGTCC GGCATCCCGG TACGTTTCTC
201 CGGTACTGGC TCTCGTACTG ATTTTACCCT GATTATCGAC CCGGTGGAAG
251 CAGACGATGT TGCCACCTAC TATTGCCAGC AGACCAACGA GGATCCGTAC
301 ACCTTCGGTG GCGGTACTAA ACTGGAGATC AAAGGCGGTG GTGGTTCTGG
351 TGGTGGTGGT AGCGGCGGCG GTGGTAGCGG TGGCGGTGGC AGCGGTGGTG
401 GTGGCTCTGG TGGCGGTGGC TCTGAAGTGC AGCTGCAGCA GTCCGGTGCG
451 GAGCTCGTTG AACCGGGCGC TTCTGTGAAA CTGTCTTGCA CTGCATCTGG
501 TTTCAACATT AAGGACACCT ACATGCACTG GGTGAAACAA CGCCCGGAAC
551 AGGGTCTGGA GTGGATCGGT CGCATCGATC CGGCTAACGG TAACAGCAAA
601 TACGTGCCAA AATTCCAGGG TAAAGCAACC ATCACTGCTG ATACCTCCTC
651 TAACACTGCT TACCTGCAGC TGACTTCCCT GACTAGCGAA GACACCGCGG
701 TTTATTACTG CGCTCCGTTC GGCTACTATG TCAGCGATTA CGCAATGGCC
751 TACTGGGGTC AGGGCACCTC TGTTACCGTT TCTAGC (SEQ ID NO:3)
```

FIG._1B

```
263 TPVSEKQL   AEVVANTITP LMKAQSVPGM AVAVIYQGKP
301 HYYTFGKADI AANKPVTPQT LFELGSISKT FTGVLGGDAI ARGEISLDDA
351 VTRYWPQLTG KQWQGIRMLD LATYTAGGLP LQVPDEVTDN ASLLRFYQNW
401 QPQWKPGTTR LYANASIGLF GALAVKPSGM PYEQAMTTRV LKPLKLDHTW
451 INVPKAEEAH YAWGYRDGKA VRVSPGMLDA QAYGVKTNVQ DMANWVMANM
501 APENVADASL KQGIALAQSR YWRIGSMYQG LGWEMLNWPV EANTVVETSF
551 GNVALAPLPV AEVNPPAPPV KASWVHKTGS TGGFGSYVAF IPEKQIGIVM
602 LANTSYPNPA RVEAAYHILE ALQ (SEQ ID NO:11)
```

FIG._1C

```
   1  ACACCGGTGT  CAGAAAAACA  GCTGGCGGAG  GTGGTCGCGA  ATACGATTAC
  51  CCCGCTGATG  AAAGCCCAGT  CTGTTCCAGG  CATGGCGGTG  GCCGTTATTT
 101  ATCAGGGAAA  ACCGCACTAT  TACACATTTG  GCAAGGCCGA  TATCGCGGCG
 151  AATAAACCCG  TTACGCCTCA  GACCCTGTTC  GAGCTGGGTT  CTATAAGTAA
 201  AACCTTCACC  GGCGTTTTAG  GTGGGGATGC  CATTGCTCGC  GGTGAAATTT
 251  CGCTGGACGA  TGCGGTGACC  AGATACTGGC  CACAGCTGAC  GGGCAAGCAG
 301  TGGCAGGGTA  TTCGTATGCT  GGATCTCGCC  ACCTACACCG  CTGGCGGCCT
 351  GCCGCTACAG  GTACCGGATG  AGGTCACGGA  TAACGCCTCC  CTGCTGCGCT
 401  TTTATCAAAA  CTGGCAGCCG  CAGTGGAAGC  CTGGCACAAC  GCGTCTTTAC
 451  GCCAACGCCA  GCATCGGTCT  TTTTGGTGCG  CTGGCGGTCA  AACCTTCTGG
 501  CATGCCCTAT  GAGCAGGCCA  TGACGACGCG  GGTCCTTAAG  CCGCTCAAGC
 551  TGGACCATAC  CTGGATTAAC  GTGCCGAAAG  CGGAAGAGGC  GCATTACGCC
 601  TGGGGCTATC  GTGACGGTAA  AGCGGTGCGC  GTTTCGCCGG  GTATGCTGGA
 651  TGCACAAGCC  TATGGCGTGA  AAACCAACGT  GCAGGATATG  GCGAACTGGG
 701  TCATGGCAAA  CATGGCGCCG  GAGAACGTTG  CTGATGCCTC  ACTTAAGCAG
 751  GGCATCGCGC  TGGCGCAGTC  GCGCTACTGG  CGTATCGGGT  CAATGTATCA
 801  GGGTCTGGGC  TGGGAGATGC  TCAACTGGCC  CGTGGAGGCC  AACACGGTGG
 851  TCGAGACGAG  TTTTGGTAAT  GTAGCACTGG  CGCCGTTGCC  CGTGGCAGAA
 901  GTGAATCCAC  CGGCTCCCCC  GGTCAAAGCG  TCCTGGGTCC  ATAAAACGGG
 951  CTCTACTGGC  GGGTTTGGCA  GCTACGTGGC  CTTTATTCCT  GAAAAGCAGA
1001  TCGGTATTGT  GATGCTCGCG  AATACAAGCT  ATCCGAACCC  GGCACGCGTT
1051  GAGGCGGCAT  ACCATATCCT  CGAGGCGCTA  CAG (SEQ ID NO:12)
```

FIG._1D

```
   1  DIVLTQSPAS  LAVSLGQRAT  MSCRAGESVD  IFGVGFLHWY  QQKPGQPPKL
  51  LIYRASNLES  GIPVRFSGTG  SRTDFTLIID  PVEADDVATY  YCQQTNEDPY
 101  TFGGGTKLEI  KGGGGSGGGG  SGGGGSGGGG  SGGGGSGGGG  SEVQLQQSGA
 151  ELVEPGASVK  LSCTASGFNI  KDTYMHWVKQ  RPEQGLEWIG  RIDPANGNSK
 201  YVPKFQGKAT  ITADTSSNTA  YLQLTSLTSE  DTAVYYCAPF  GYYVSDYAMA
 251  YWGQGTSVTV  SSTPVSEKQL  AEVVANTITP  LMKAQSVPGM  AVAVIYQGKP
 301  HYYTFGKADI  AANKPVTPQT  LFELGSISKT  FTGVLGGDAI  ARGEISLDDA
 351  VTRYWPQLTG  KQWQGIRMLD  LATYTAGGLP  LQVPDEVTDN  ASLLRFYQNW
 401  QPQWKPGTTR  LYANASIGLF  GALAVKPSGM  PYEQAMTTRV  LKPLKLDHTW
 451  INVPKAEEAH  YAWGYRDGKA  VRVSPGMLDA  QAYGVKTNVQ  DMANWVMANM
 501  APENVADASL  KQGIALAQSR  YWRIGSMYQG  LGWEMLNWPV  EANTVVETSF
 551  GNVALAPLPV  AEVNPPAPPV  KASWVHKTGS  TGGFGSYVAF  IPEKQIGIVM
 601  LANTSYPNPA  RVEAAYHILE  ALQ (SEQ ID NO:2)
```

FIG._1E

```
   1 GACATCGTCC TGACCCAGAG CCCGGCAAGC CTGGCTGTTT CCCTGGGCCA
  51 GCGTGCCACT ATGTCCTGCA GAGCGGGTGA GTCTGTTGAC ATTTTCGGTG
 101 TCGGTTTTCT GCACTGGTAC CAACAGAAAC CGGGTCAGCC GCCAAAACTG
 151 CTGATCTATC GTGCTTCTAA CCTGGAGTCC GGCATCCCGG TACGTTTCTC
 201 CGGTACTGGC TCTCGTACTG ATTTTACCCT GATTATCGAC CCGGTGGAAG
 251 CAGACGATGT TGCCACCTAC TATTGCCAGC AGACCAACGA GGATCCGTAC
 301 ACCTTCGGTG CGGGTACTAA ACTGGAGATC AAAGGCGGTG GTGGTTCTGG
 351 TGGTGGTGGT AGCGGCGGCG GTGGTAGCGG TGGCGGTGGC AGCGGTGGTG
 401 GTGGCTCTGG TGGCGGTGGC TCTGAAGTGC AGCTGCAGCA GTCCGGTGCG
 451 GAGCTCGTTG AACCGGGCGC TTCTGTGAAA CTGTCTTGCA CTGCATCTGG
 501 TTTCAACATT AAGGACACCT ACATGCACTG GGTGAAACAA CGCCCGGAAC
 551 AGGGTCTGGA GTGGATCGGT CGCATCGATC CGGCTAACGG TAACAGCAAA
 601 TACGTGCCAA AATTCCAGGG TAAAGCAACC ATCACTGCTG ATACCTCCTC
 651 TAACACTGCT TACCTGCAGC TGACTTCCCT GACTAGCGAA GACACCGCGG
 701 TTTATTACTG CGCTCCGTTC GGCTACTATG TCAGCGATTA CGCAATGGCC
 751 TACTGGGGTC AGGGCACCTC TGTTACCGTT TCTAGCACAC GGTGTCAGA
 801 AAAACAGCTG GCGGAGGTGG TCGCAATAC GATTACCCCG CTGATGAAAG
 851 CCCAGTCTGT TCCAGGCATG GCGGTGGCCG TTATTTATCA GGGAAAACCG
 901 CACTATTACA CATTTGGCAA GGCCGATATC GCGGCGAATA AACCCGTTAC
 951 GCCTCAGACC CTGTTCGAGC TGGGTTCTAT AAGTAAAACC TTCACCGGCG
1001 TTTTAGTGG GGATGCCATT GCTCGCGGTG AAATTTCGCT GGACGATGCG
1051 GTGACCAGAT ACTGGCCACA GCTGACGGGC AAGCAGTGGC AGGGTATTCG
1101 TATGCTGGAT CTCGCCACCT ACACCGCTGG CGGCCTGCCG CTACAGGTAC
1151 CGGATGAGGT CACGGATAAC GCCTCCTGC TGCGCTTTTA TCAAAACTGG
1201 CAGCCGCAGT GGAAGCCTGG CACAACGCGT CTTTACGCCA ACGCCAGCAT
1251 CGGTCTTTTT GGTGCGCTGG CGGTCAAACC TTCTGGCATG CCCTATGAGC
1301 AGGCCATGAC GACGCGGGTC CTTAAGCCGC TCAAGCTGGA CCATACCTGG
1351 ATTAACGTGC CGAAAGCGGA AGAGGCGCAT TACGCCTGGG GCTATCGTGA
1401 CGGTAAAGCG GTGCGCGTTT CGCCGGGTAT GCTGGATGCA CAAGCCTATG
1451 GCGTGAAAAC CAACGTGCAG GATATGGCGA ACTGGGTCAT GGCAAACATG
1501 GCGCCGGAGA ACGTTGCTGA TGCCTCACTT AAGCAGGGCA TCGCGCTGGC
1551 GCAGTCGCGC TACTGGCGTA TCGGGTCAAT GTATCAGGGT CTGGGCTGGG
1601 AGATGCTCAA CTGGCCCGTG GAGGCCAACA CGGTGGTCGA GACGAGTTTT
1651 GGTAATGTAG CACTGGCGCC GTTGCCCGTG GCAGAAGTGA ATCCACCGGC
1701 TCCCCCGGTC AAAGCGTCCT GGGTCCATAA AACGGGCTCT ACTGGCGGGT
1751 TTGGCAGCTA CGTGGCCTTT ATTCCTGAAA AGCAGATCGG TATTGTGATG
1801 CTCGCGAATA CAAGCTATCC GAACCCGGCA CGCGTTGAGG CGGCATACCA
1851 TATCCTCGAG GCGCTACAG (SEQ ID NO:4)
```

FIG. _1F

```
  1 DIVLTQSPAS LSVSLGQRAT MSCRAGESVD IFGVGFLHWY QQKPGQPPKL
 51 LIYRASNLES GIPVRFSGTG SGTDFTLIID PVEADDVATY YCQQTNEDPY
101 TFGGGTKLEI KGGGGSGGGG SGGGGSGGGG SGGGGSGGGG SEVQLQQSGA
151 ELVEPGASVK LSCTASGFNI KDTYMHWVKQ RPEQGLEWIG RIDPANGNSK
201 YVPKFQGKAT ITADTSSNTA YLQLTSLTSE DTAVYYCAPF GYYVSDYAMA
251 YWGQGTSVTV SS (SEQ ID NO:5)
```

FIG. _2A

```
  1 GACATCGTCC TGACCCAGAG CCCGGCAAGC CTGTCTGTTT CCCTGGGCCA
 51 GCGTGCCACT ATGTCCTGCA GAGCGGGTGA GTCTGTTGAC ATTTTCGGTG
101 TCGGTTTTCT GCACTGGTAC CAACAGAAAC CGGGTCAGCC GCCAAAACTG
151 CTGATCTATC GTGCTTCTAA CCTGGAGTCC GGCATCCCGG TACGTTTCTC
201 CGGTACTGGC TCTGGTACTG ATTTTACCCT GATTATCGAC CCGGTGGAAG
251 CAGACGATGT TGCCACCTAC TATTGCCAGC AGACCAACGA GGATCCGTAC
301 ACCTTCGGTG CGGTACTAAA CTGGAGATCA AAGGCGGTG GTGGTTCTGG
351 TGGTGGTGGT AGCGGTGGCG GTGGTAGCGG TGGCGGTGGC AGCGGTGGTG
401 GTGGCTCTGG TGGCGGTGGC TCTGAAGTGC AGCTGCAGCA GTCCGGTGCG
451 GAGCTCGTTG AACCGGGCGC TTCTGTGAAA CTGTCTTGCA CTGCATCTGG
501 TTTCAACATT AAGGACACCT ACATGCACTG GGTGAAACAA CGCCCGGAAC
551 AGGGTCTGGA GTGGATCGGT CGCATCGATC CGGCTAACGG TAACAGCAAA
601 TACGTGCCAA AATTCCAGGG TAAAGCAACC ATCACTGCTG ATACCTCCTC
651 TAACACTGCT TACCTGCAGC TGACTTCCCT GACTAGCGAA GACACCGCGG
701 TTTATTACTG CGCTCCGTTC GGCTACTATG TCAGCGATTA CGCAATGGCC
751 TACTGGGGTC AGGGCACCTC TGTTACCGTT TCTAGC (SEQ ID NO:6)
```

FIG._2B

```
262 TPVSEKQL AEVVANTITP LMAAQSVPGM AVAVIYQGKP
301 HYYTFGKADI AANKPVTPQT LFELGSISKT FTGVLGGDAI ARGEISLDDA
351 VTRYWPQLTG KQWQGIRMLD LATYTAGGLP LQVPDEVTDN ASLLRFYQNW
401 QPQWKPGTTR LYANASIGLF GALAVKPSGM PYEQAMTTRV LKPLKLDHTW
451 INVPKAEEAH YAWGYRDGKA VRVSPGMLDA QAYGVKTNVQ DMANWVMANM
501 APENVADASL KQGIALAQSR YWRIGSMYQG LGWEMLNWPV EANTVVETSF
551 GNVALAPLPV AEVNPPAPPV KASWVHKTGS TGGFGAYVAF IPEKQIGIVM
601 LANTSYPNPA RVEAAYHILE ALQ (SEQ ID NO:13)
```

FIG._3

```
  1 DIVLTQSPAS LSVSLGQRAT MSCRAGESVD IFGVGFLHWY QQKPGQPPKL
 51 LIYRASNLES GIPVRFSGTG SGTDFTLIID PVEADDVATY YCQQTNEDPY
101 TFGGGTKLEI KGGGGSGGGG SGGGGSGGGG SGGGGSGGGG SEVQLQQSGA
151 ELVEPGASVK LSCTASGFNI KDTYMHWVKQ RPEQGLEWIG RIDPANGNSK
201 YVPKFQGKAT ITADTSSNTA YLQLTSLTSE DTAVYYCAPF GYYVSDYAMA
251 YWGQGTSVTV SSTPVSEKQL AEVVANTITP LMKAQSVPGM AVAVIYQGKP
301 HYYTFGKADI AANKPVTPQT LFELGSISKT FTGVLGGDAI ARGEISLDDA
351 VTRYWPQLTG KQWQGIRMLD LATYTAGGLP LQVPDEVTDN ASLLRFYQNW
401 QPQWKPGTTR LYANASIGLF GALAVKPSGM PYEQAMTTRV LKPLKLDHTW
451 INVPKAEEAH YAWGYRDGKA VRVSPGMLDA QAYGVKTNVQ DMANWVMANM
501 APENVADASL KQGIALAQSR YWRIGSMYQG LGWEMLNWPV EANTVVETSF
551 GNVALAPLPV AEVNPPAPPV KASWVHKTGS TGGFGSYVAF IPEKQIGIVM
601 LANTSYPNPA RVEAAYHILE ALQ (SEQ ID NO:7)
```

FIG._4A

```
   1  GACATCGTCC TGACCCAGAG CCCGGCAAGC CTGTCTGTTT CCCTGGGCCA
  51  GCGTGCCACT ATGTCCTGCA GAGCGGGTGA GTCTGTTGAC ATTTTCGGTG
 101  TCGGTTTTCT GCACTGGTAC CAACAGAAAC CGGGTCAGCC GCCAAAACTG
 151  CTGATCTATC GTGCTTCTAA CCTGGAGTCC GGCATCCCGG TACGTTTCTC
 201  CGGTACTGGC TCTGGTACTG ATTTTACCCT GATTATCGAC CCGGTGGAAG
 251  CAGACGATGT TGCCACCTAC TATTGCCAGC AGACCAACGA GGATCCGTAC
 301  ACCTTCGGTG GCGGTACTAA ACTGGAGATC AAAGGCGGTG GTGGTTCTGG
 351  TGGTGGTGGT AGCGGTGGCG GTGGTAGCGG TGGCGGTGGC AGCGGTGGTG
 401  GTGGCTCTGG TGGCGGTGGC TCTGAAGTGC AGCTGCAGCA GTCCGGTGCG
 451  GAGCTCGTTG AACCGGGCGC TTCTGTGAAA CTGTCTTGCA CTGCATCTGG
 501  TTTCAACATT AAGGACACCT ACATGCACTG GGTGAAACAA CGCCCGGAAC
 551  AGGGTCTGGA GTGGATCGGT CGCATCGATC CGGCTAACGG TAACAGCAAA
 601  TACGTGCCAA AATTCCAGGG TAAAGCAACC ATCACTGCTG ATACCTCCTC
 651  TAACACTGCT TACCTGCAGC TGACTTCCCT GACTAGCGAA GACACCGCGG
 701  TTTATTACTG CGCTCCGTTC GGCTACTATG TCAGCGATTA CGCAATGGCC
 751  TACTGGGGTC AGGGCACCTC TGTTACCGTT CTAGCACAC CGGTGTCAGA
 801  AAAACAGCTG GCGGAGGTGG TCGCGAATAC GATTACCCCG CTGATGAAAG
 851  CCCAGTCTGT TCCAGGCATG GCGGTGGCCG TTATTTATCA GGGAAAACCG
 901  CACTATTACA CATTTGGCAA GGCCGATATC GCGGCGAATA AACCCGTTAC
 951  GCCTCAGACC CTGTTCGAGC TGGGTTCTAT AAGTAAAACC TTCACCGGCG
1001  TTTTAGGTGG GGATGCCATT GCTCGCGGTG AAATTTCGCT GGACGATGCG
1051  GTGACCAGAT ACTGGCCACA GCTGACGGGC AAGCAGTGGC AGGGTATTCG
1101  TATGCTGGAT CTCGCCACCT ACACCGCTGG CGGCCTGCCG CTACAGGTAC
1151  CGGATGAGGT CACGGATAAC GCCTCCCTGC TGCGCTTTTA TCAAAACTGG
1201  CAGCCGCAGT GGAAGCCTGG CACAACGCGT CTTTACGCCA ACGCCAGCAT
1251  CGGTCTTTTT GGTGCGCTGG CGGTCAAACC TTCTGGCATG CCCTATGAGC
1301  AGGCCATGAC GACGCGGGTC CTTAAGCCGC TCAAGCTGGA CCATACCTGG
1351  ATTAACGTGC CGAAAGCGGA AGAGGCGCAT TACGCCTGGG CTATCGTGA
1401  CGGTAAAGCG GTGCGCGTTT CGCCGGGTAT GCTGGATGCA CAAGCCTATG
1451  GCGTGAAAAC CAACGTGCAG GATATGGCGA ACTGGGTCAT GGCAAACATG
1501  GCGCCGGAGA ACGTTGCTGA TGCCTCACTT AAGCAGGGCA TCGCGCTGGC
1551  GCAGTCGCGC TACTGGCGTA TCGGGTCAAT GTATCAGGGT CTGGGCTGGG
1601  AGATGCTCAA CTGGCCCGTG GAGGCCAACA CGGTGGTCGA CGAGTTTTT
1651  GGTAATGTAG CACTGGCGCC GTTGCCCGTG GCAGAAGTGA ATCCACCGGC
1701  TCCCCCGGTC AAAGCGTCCT GGGTCCATAA AACGGGCTCT ACTGGCGGGT
1751  TTGGCAGCTA CGTGGCCTTT ATTCCTGAAA AGCAGATCGG TATTGTGATG
1801  CTCGCGAATA CAAGCTATCC GAACCCGGCA CGCGTTGAGG CGGCATACCA
1851  TATCCTCGAG GCGCTACAG (SEQ ID NO:9)
```

FIG._4B

```
  1 DIVLTQSPAS LSVSLGQRAT MSCRAGESVD IFGVGFLHWY QQKPGQPPKL
 51 LIYRASNLES GIPVRFSGTG SGTDFTLIID PVEADDVATY YCQQTNEDPY
101 TFGGGTKLEI KGGGGSGGGG SGGGGSGGGG SGGGGSGGGG SEVQLQQSGA
151 ELVEPGASVK LSCTASGFNI KDTYMHWVKQ RPEQGLEWIG RIDPANGNSK
201 YVPKFQGKAT ITADTSSNTA YLQLTSLTSE DTAVYYCAPF GYYVSDYAMA
251 YWGQGTSVTV SSTPVSEKQL AEVVANTITP LMAAQSVPGM AVAVIYQGKP
301 HYYTFGKADI AANKPVTPQT LFELGSISKT FTGVLGGDAI ARGEISLDDA
351 VTRYWPQLTG KQWQGIRMLD LATYTAGGLP LQVPDEVTDN ASLLRFYQNW
401 QPQWKPGTTR LYANASIGLF GALAVKPSGM PYEQAMTTRV LKPLKLDHTW
451 INVPKAEEAH YAWGYRDGKA VRVSPGMLDA QAYGVKTNVQ DMANWVMANM
501 APENVADASL KQGIALAQSR YWRIGSMYQG LGWEMLNWPV EANTVVETSF
551 GNVALAPLPV AEVNPPAPPV KASWVHKTGS TGGFGAYVAF IPEKQIGIVM
601 LANTSYPNPA RVEAAYHILE ALQ (SEQ ID NO:8)
```

FIG._4C

```
   1  GACATCGTCC TGACCCAGAG CCCGGCAAGC CTGTCTGTTT CCCTGGGCCA
  51  GCGTGCCACT ATGTCCTGCA GAGCGGGTGA GTCTGTTGAC ATTTTCGGTG
 101  TCGGTTTTCT GCACTGGTAC CAACAGAAAC CGGGTCAGCC GCCAAAACTG
 151  CTGATCTATC GTGCTTCTAA CCTGGAGTCC GGCATCCCGG TACGTTTCTC
 201  CGGTACTGGC TCTGGTACTG ATTTTACCCT GATTATCGAC CCGGTGGAAG
 251  CAGACGATGT TGCCACCTAC TATTGCCAGC AGACCAACGA GGATCCGTAC
 301  ACCTTCGGTG CGGTACTAA ACTGGAGATC AAAGGCGGTG GTGGTTCTGG
 351  TGGTGGTGGT AGCGGTGGCG GTGGTAGCGG TGGCGGTGGC AGCGGTGGTG
 401  GTGGCTCTGG TGGCGGTGGC TCTGAAGTGC AGCTGCAGCA GTCCGGTGCG
 451  GAGCTCGTTG AACCGGGCGC TTCTGTGAAA CTGTCTTGCA CTGCATCTGG
 501  TTTCAACATT AAGGACACCT ACATGCACTG GGTGAAACAA CGCCCGGAAC
 551  AGGGTCTGGA GTGGATCGGT CGCATCGATC CGGCTAACGG TAACAGCAAA
 601  TACGTGCCAA AATTCCAGGG TAAAGCAACC ATCACTGCTG ATACCTCCTC
 651  TAACACTGCT TACCTGCAGC TGACTTCCCT GACTAGCGAA GACACCGCGG
 701  TTTATTACTG CGCTCCGTTC GGCTACTATG TCAGCGATTA CGCAATGGCC
 751  TACTGGGGTC AGGGCACCTC TGTTACCGTT TCTAGCACAC CGGTGTCAGA
 801  AAAACAGCTG GCGGAGGTGG TCGCGAATAC GATTACCCCG CTGATGGCGG
 851  CCCAGTCTGT TCCAGGCATG GCGGTGGCCG TTATTTATCA GGGAAAACCG
 901  CACTATTACA CATTTGGCAA GGCCGATATC GCGGCGAATA AACCCGTTAC
 951  GCCTCAGACC CTGTTCGAGC TGGGTTCTAT AAGTAAAACC TTCACCGGCG
1001  TTTTAGGTGG GGATGCCATT GCTCGCGGTG AAATTTCGCT GGACGATGCG
1051  GTGACCAGAT ACTGGCCACA GCTGACGGGC AAGCAGTGGC AGGGTATTCG
1101  TATGCTGGAT CTCGCCACCT ACACCGCTGG CGGCCTGCCG CTACAGGTAC
1151  CGGATGAGGT CACGGATAAC GCCTCCCTGC TGCGCTTTTA TCAAAACTGG
1201  CAGCCGCAGT GGAAGCCTGG CACAACGCGT CTTTACGCCA ACGCCAGCAT
1251  CGGTCTTTTT GGTGCGCTGG CGGTCAAACC TTCTGGCATG CCCTATGAGC
1301  AGGCCATGAC GACGCGGGTC CTTAAGCCGC TCAAGCTGGA CCATACCTGG
1351  ATTAACGTGC CGAAAGCGGA AGAGGCGCAT TACGCCTGGG CTATCGTGA
1401  CGGTAAAGCG GTGCGCGTTT CGCCGGGTAT GCTGGATGCA CAAGCCTATG
1451  GCGTGAAAAC CAACGTGCAG GATATGGCGA ACTGGGTCAT GGCAAACATG
1501  GCGCCGGAGA ACGTTGCTGA TGCCTCACTT AAGCAGGGCA TCGCGCTGGC
1551  GCAGTCGCGC TACTGGCGTA TCGGGTCAAT GTATCAGGGT CTGGGCTGGG
1601  AGATGCTCAA CTGGCCCGTG GAGGCCAACA CGGTGGTCGA GACGAGTTTT
1651  GGTAATGTAG CACTGGCGCC GTTGCCCGTG GCAGAAGTGA ATCCACCGGC
1701  TCCCCGGTC AAAGCGTCCT GGGTCCATAA AACGGGCTCT ACTGGCGGGT
1751  TGGCGCGTA CGTGGCCTTT ATTCCTGAAA AGCAGATCGG TATTGTGATG
1801  CTCGCGAATA CAAGCTATCC GAACCCGGCA CGCGTTGAGG CGGCATACCA
1851  TATCCTCGAG GCGCTACAG (SEQ ID NO:10)
```

FIG._4D

```
   1  AGGAATTATC ATATGAAATA CCTGCTGCCG ACCGCTGCTG CTGGTCTGCT
  51  GCTCCTCGCT GCCCAGCCGG CCATGGCCGA CATCGTCCTG ACCCAGAGCC
 101  CGGCAAGCCT GTCTGTTTCC CTGGGCCAGC GTGCCACTAT GTCCTGCAGA
 151  GCGGGTGAGT CTGTTGACAT TTTCGGTGTC GGTTTTCTGC ACTGGTACCA
 201  ACAGAAACCG GGTCAGCCGC CAAAACTGCT GATCTATCGT GCTTCTAACC
 251  TGGAGTCCGG CATCCCGGTA CGTTTCTCCG GTACTGGCTC TGGTACTGAT
 301  TTTACCCTGA TTATCGACCC GGTGGAAGCA GACGATGTTG CCACCTACTA
 351  TTGCCAGCAG ACCAACGAGG ATCCGTACAC CTTCGGTGGC GGTACTAAAC
 401  TGGAGATCAA AGGCGGTGGT GGTTCTGGTG GTGGTGGTAG CGGTGGCGGT
 451  GGTAGCGGTG GCGGTGGCAG CGGTGGTGGT GGCTCTGGTG GCGGTGGCTC
 501  TGAAGTGCAG CTGCAGCAGT CCGGTGCGGA GCTCGTTGAA CCGGGCGCTT
 551  CTGTGAAACT GTCTTGCACT GCATCTGGTT TCAACATTAA GGACACCTAC
 601  ATGCACTGGG TGAAACAACG CCCGGAACAG GGTCTGGAGT GGATCGGTCG
 651  CATCGATCCG GCTAACGGTA ACAGCAAATA CGTGCCAAAA TTCCAGGGTA
 701  AAGCAACCAT CACTGCTGAT ACCTCCTCTA ACACTGCTTA CCTGCAGCTG
 751  ACTTCCCTGA CTAGCGAAGA CACCGCGGTT TATTACTGCG CTCCGTTCGG
 801  CTACTATGTC AGCGATTACG CAATGGCCTA CTGGGGTCAG GGCACCTCTG
 851  TTACCGTTTC TAGCACACCG GTGTCAGAAA AACAGCTGGC GGAGGTGGTC
 901  GCGAATACGA TTACCCCGCT GATGGCGGCC CAGTCTGTTC AGGCATGGC
 951  GGTGGCCGTT ATTTATCAGG GAAAACCGCA CTATTACACA TTTGGCAAGG
1001  CCGATATCGC GGCGAATAAA CCCGTTACGC CTCAGACCCT GTTCGAGCTG
1051  GGTTCTATAA GTAAAACCTT CACCGGCGTT TTAGGTGGGG ATGCCATTGC
1101  TCGCGGTGAA ATTTCGCTGG ACGATGCGGT GACCAGATAC TGGCCACAGC
1151  TGACGGGCAA GCAGTGGCAG GGTATTCGTA TGCTGGATCT CGCCACCTAC
1201  ACCGCTGGCG GCCTGCCGCT ACAGGTACCG GATGAGGTCA CGGATAACGC
1251  CTCCCTGCTG CGCTTTTATC AAAACTGGCA GCCGCAGTGG AAGCCTGGCA
1301  CAACGCGTCT TTACGCCAAC GCCAGCATCG GTCTTTTTGG TGCGCTGGCG
1351  GTCAAACCTT CTGGCATGCC CTATGAGCAG GCCATGACGA CGCGGGTCCT
1401  TAAGCCGCTC AAGCTGGACC ATACCTGGAT TAACGTGCCG AAAGCGGAAG
1451  AGGCGCATTA CGCCTGGGGC TATCGTGACG GTAAAGCGGT GCGCGTTTCG
1501  CCGGGTATGC TGGATGCACA AGCCTATGGC GTGAAAACCA ACGTGCAGGA
1551  TATGGCGAAC TGGGTCATGG CAAACATGGC GCCGGAGAAC GTTGCTGATG
1601  CCTCACTTAA GCAGGGCATC GCGCTGGCGC AGTCGCGCTA CTGGCGTATC
1651  GGGTCAATGT ATCAGGGTCT GGGCTGGGAG ATGCTCAACT GGCCCGTGGA
1701  GGCCAACACG GTGGTCGAGA CGAGTTTTGG TAATGTAGCA CTGGCGCCGT
1751  TGCCCGTGGC AGAAGTGAAT CCACCGGCTC CCCCGGTCAA AGCGTCCTGG
1801  GTCCATAAAA CGGGCTCTAC TGGCGGGTTT GGCGCGTACG TGGCCTTTAT
1851  TCCTGAAAAG CAGATCGGTA TTGTGATGCT CGCGAATACA AGCTATCCGA
1901  ACCCGGCACG CGTTGAGGCG GCATACCATA TCCTCGAGGC GCTACAGTAG
1951  GAATTCGAGC TCCGTCGACA AGCTTGCGGC CGCACTCGAG ATCAAACGGG
2001  CTAGCCAGCC AGAACTCGCC CCGGAAGACC CCGAGGATGT CGAGCACCAC
2051  CACCACCACC ACTGAGATCC GGCTGCTAAC AAAGCCCGAA AGGAAGCTGA
2101  GTTGGCTGCT GCCACCGCTG AGCAATAACT AGCATAACCC CTTGGGGCCT
2151  CTAAACGGGT CTTGAGGGGT TTTTTGCTGA AAGGAGGAAC TATATCCGGA
2201  TTGGCGAATG GGACGCGCCC TGTAGCGGCG CATTAAGCGC GGCGGGTGTG
2251  GTGGTTACGC GCAGCGTGAC CGCTACACTT GCCAGCGCCC TAGCGCCCGC
2301  TCCTTTCGCT TTCTTCCCTT CCTTTCTCGC CACGTTCGCC GGCTTTCCCC
```

FIG._4E-1

```
2351  GTCAAGCTCT AAATCGGGGG CTCCCTTTAG GGTTCCGATT TAGTGCTTTA
2401  CGGCACCTCG ACCCCAAAAA ACTTGATTAG GGTGATGGTT CACGTAGTGG
2451  GCCATCGCCC TGATAGACGG TTTTTCGCCC TTTGACGTTG GAGTCCACGT
2501  TCTTTAATAG TGGACTCTTG TTCCAAACTG GAACAACACT CAACCCTATC
2551  TCGGTCTATT CTTTTGATTT ATAAGGGATT TTGCCGATTT CGGCCTATTG
2601  GTTAAAAAAT GAGCTGATTT AACAAAAATT TAACGCGAAT TTTAACAAAA
2651  TATTAACGCT TACAATTTCC TGATGCGGTA TTTTCTCCTT ACGCATCTGT
2701  GCGGTATTTC ACACCGCATA TGGTGCACTC TCAGTACAAT CTGCTCTGAT
2751  GCCGCATAGT TAAGCCAGCC CCGACACCCG CCAACACCCG CTGACGCGCC
2801  CTGACGGGCT TGTCTGCTCC CGGCATCCGC TTACAGACAA GCTGTGACCG
2851  TCTCCGGGAG CTGCATGTGT CAGAGGTTTT CACCGTCATC ACCGAAACGC
2901  GCGAGACGAA AGGGCCTCGT GATACGCCTA TTTTTATAGG TTAATGTCAT
2951  GATAATAATG GTTTCTTAGA CGTCAGGTGG CACTTTTCGG GGAAATGTGC
3001  GCGGAACCCC TATTTGTTTA TTTTTCTAAA TACATTCAAA TATGTATCCG
3051  CTCATGAGAC AATAACCCTG TGGCAGCATC ACCCGACGCA CTTTGCGCCG
3101  AATAAATACC TGTGACGGAA GATCACTTCG CAGAATAAAT AAATCCTGGT
3151  GTCCCTGTTG ATACCGGGAA GCCCTGGGCC AACTTTTGGC GAAAATGAGA
3201  CGTTGATCGG CACGTAAGAG GTTCCAACTT TCACCATAAT GAAATAAGAT
3251  CACTACCGGG CGTATTTTTT GAGTTATCGA GATTTTCAGG AGCTAAGGAA
3301  GCTAAAATGG AGAAAAAAAT CACTGGATAT ACCACCGTTG ATATATCCCA
3351  ATGGCATCGT AAAGAACATT TTGAGGCATT TCAGTCAGTT GCTCAATGTA
3401  CCTATAACCA GACCGTTCAG CTGGATATTA CGGCCTTTTT AAAGACCGTA
3451  AAGAAAAATA AGCACAAGTT TTATCCGGCC TTTATTCACA TTCTTGCCCG
3501  CCTGATGAAT GCTCATCCGG AATTCCGTAT GGCAATGAAA GACGGTGAGC
3551  TGGTGATATG GGATAGTGTT CACCCTTGTT ACACCGTTTT CCATGAGCAA
3601  ACTGAAACGT TTTCATCGCT CTGGAGTGAA TACCACGACG ATTTCCGGCA
3651  GTTTCTACAC ATATATTCGC AAGATGTGGC GTGTTACGGT GAAAACCTGG
3701  CCTATTTCCC TAAAGGGTTT ATTGAGAATA TGTTTTTCGT CTCAGCCAAT
3751  CCCTGGGTGA GTTTCACCAG TTTTGATTTA AACGTGGCCA ATATGGACAA
3801  CTTCTTCGCC CCCGTTTTCA CGATGGCAA ATATTATACG CAAGGCGACA
3851  AGGTGCTGAT GCCGCTGGCG ATTCAGGTTC ATCATGCCGT CTGTGATGGC
3901  TTCCATGTCG GCAGAATGCT TAATGAATTA CAACAGTACT GCGATGAGTG
3951  GCAGGGCGGG GCGTAAAGAC AGATCGCTGA GATAGGTGCC TCACTGATTA
4001  AGCATTGGTA ACTGTCAGAC CAAGTTTACT CATATATACT TTAGATTGAT
4051  TTAAAACTTC ATTTTTAATT TAAAAGGATC TAGGTGAAGA TCCTTTTTGA
4101  TAATCTCATG ACCAAAATCC CTTAACGTGA GTTTTCGTTC CACTGAGCGT
4151  CAGACCCCGT AGAAAAGATC AAAGGATCTT CTTGAGATCC TTTTTTTCTG
4201  CGCGTAATCT GCTGCTTGCA AACAAAAAAA CCACCGCTAC CAGCGGTGGT
4251  TTGTTTGCCG GATCAAGAGC TACCAACTCT TTTTCCGAAG GTAACTGGCT
4301  TCAGCAGAGC GCAGATACCA AATACTGTTC TTCTAGTGTA GCCGTAGTTA
4351  GGCCACCACT TCAAGAACTC TGTAGCACCG CCTACATACC TCGCTCTGCT
4401  AATCCTGTTA CCAGTGGCTG CTGCCAGTGG CGATAAGTCG TGTCTTACCG
4451  GGTTGGACTC AAGACGATAG TTACCGGATA AGGCGCAGCG GTCGGGCTGA
4501  ACGGGGGGTT CGTGCACACA GCCCAGCTTG GAGCGAACGA CCTACACCGA
4551  ACTGAGATAC CTACAGCGTG AGCTATGAGA AAGCGCCACG CTTCCCGAAG
4601  GGAGAAAGGC GGACAGGTAT CCGGTAAGCG GCAGGGTCGG AACAGGAGAG
4651  CGCACGAGGG AGCTTCCAGG GGGAAACGCC TGGTATCTTT ATAGTCCTGT
```

FIG._4E-2

```
4701  CGGGTTTCGC  CACCTCTGAC  TTGAGCGTCG  ATTTTTGTGA  TGCTCGTCAG
4751  GGGGGCGGAG  CCTATGGAAA  AACGCCAGCA  ACGCGGCCTT  TTTACGGTTC
4801  CTGGCCTTTT  GCTGGCCTTT  TGCTCACATG  TTCTTTCCTG  CGTTATCCCC
4851  TGATTCTGTG  GATAACCGTA  TTACCGCCTT  TGAGTGAGCT  GATACCGCTC
4901  GCCGCAGCCG  AACGACCGAG  CGCAGCGAGT  CAGTGAGCGA  GGAAGCGGAA
4951  GAGCGCCCAA  TACGCAAACC  GCCTCTCCCC  GCGCGTTGGC  CGATTCATTA
5001  ATGCAGCTGG  CACGACAGGT  TTCCCGACTG  GAAAGCGGGC  AGTGAGCGCA
5051  ACGCAATTAA  TGTGAGTTAG  CTCACTCATT  AGGCACCCCA  GGCTTTACAC
5101  TTTATGCTTC  CGGCTCGTAT  GTTGTGTGGA  ATTGTGAGCG  GATAACAATT
5151  TCACACAGGA  AACAGCTATG  ACCATGATTA  CGCCAAGCTA  TTTAGGTGAC
5201  ACTATAGAAT  ACTCAAGCTT  TCTAGATTAA  GG
```

FIG._4E-3

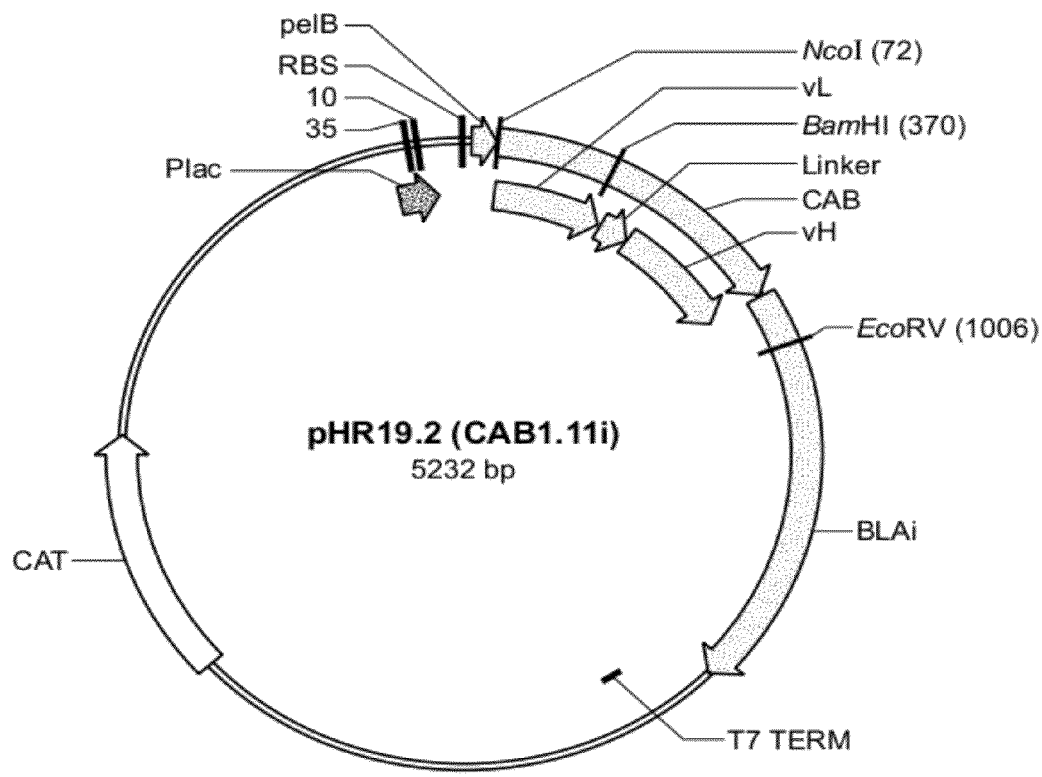
FIG._5
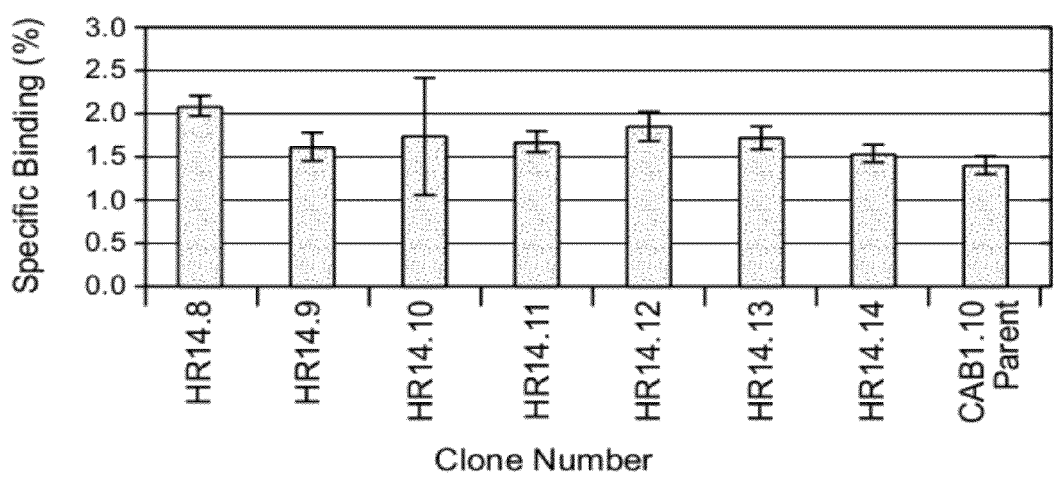
FIG._6

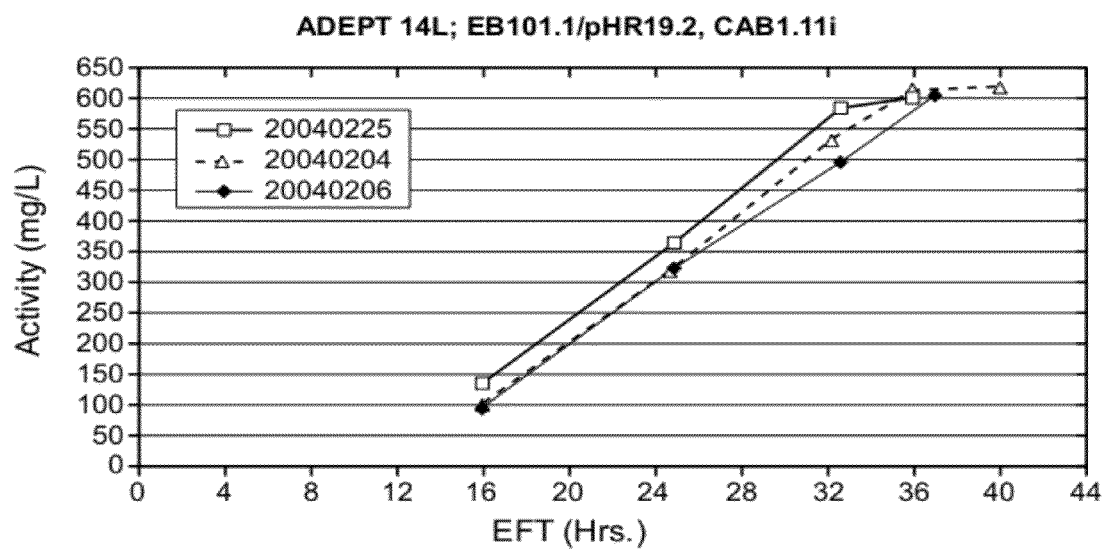
FIG._7
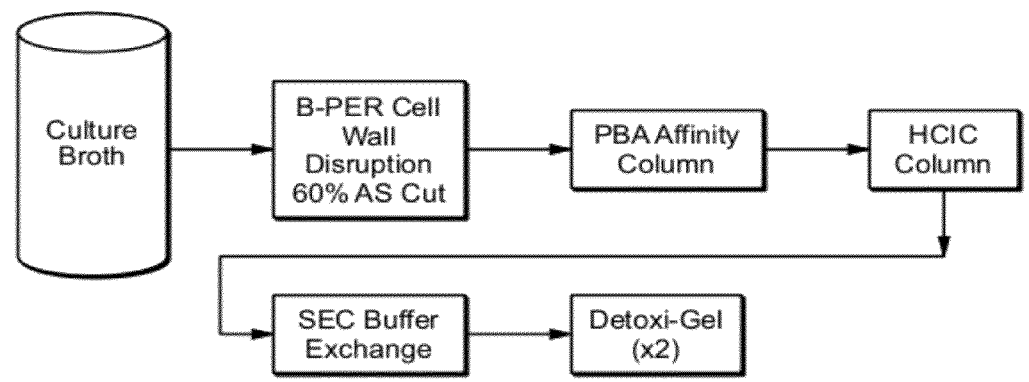
FIG._8

Lane 1: Molecular Weight Standard; Lanes 3-5: Unrelated Proteins; Lane 6: CAB1.11i.
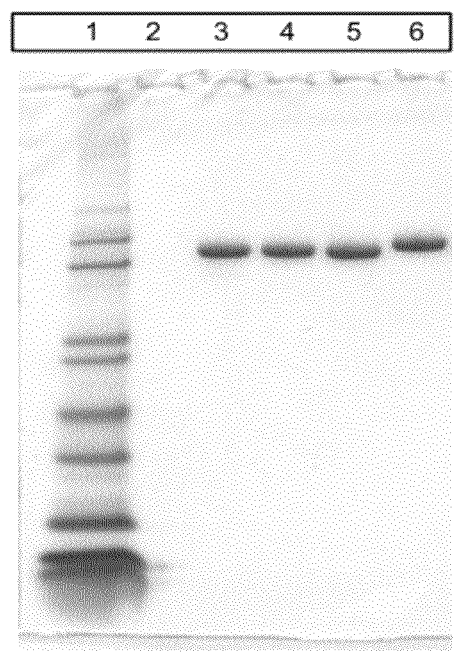
*FIG._9*

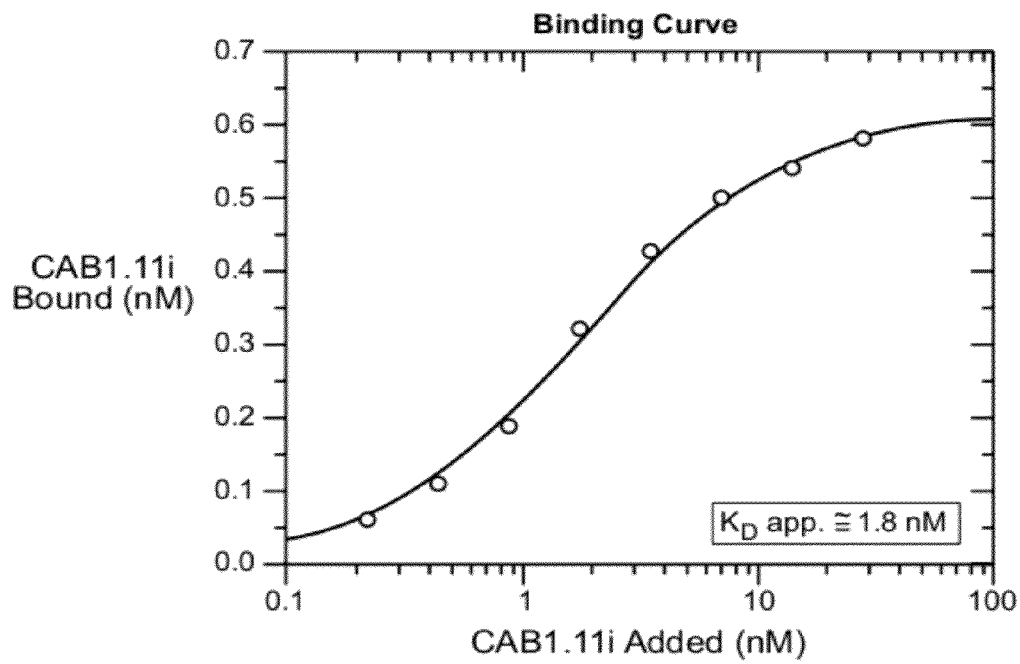
FIG._10A
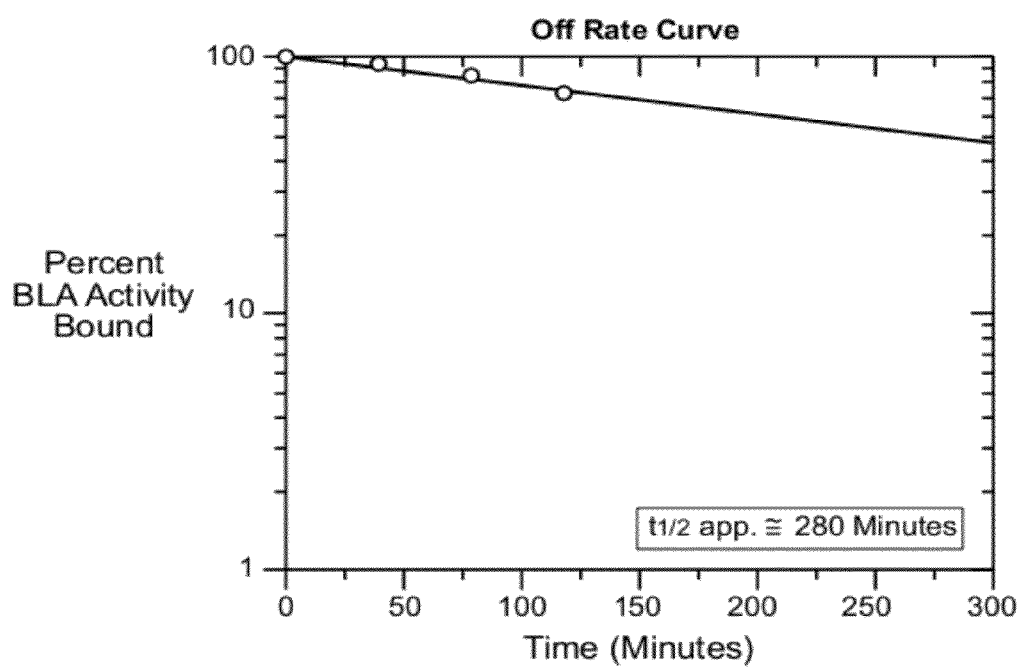
FIG._10B

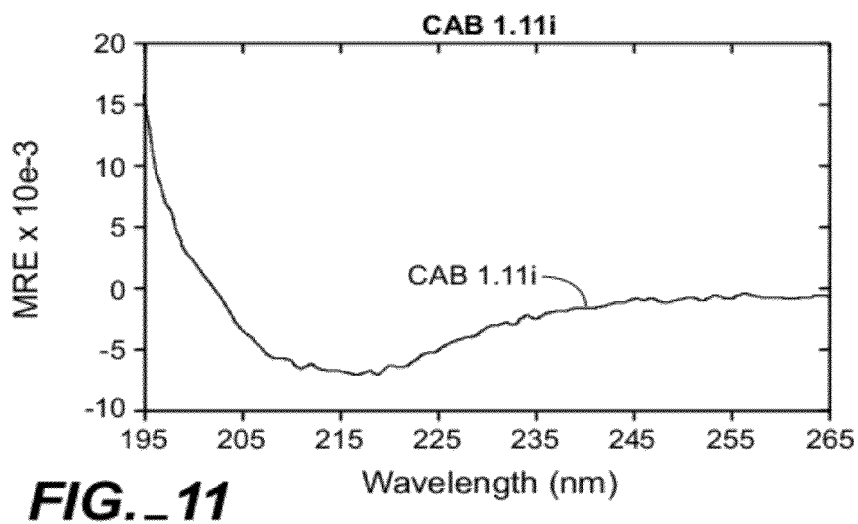
FIG._11
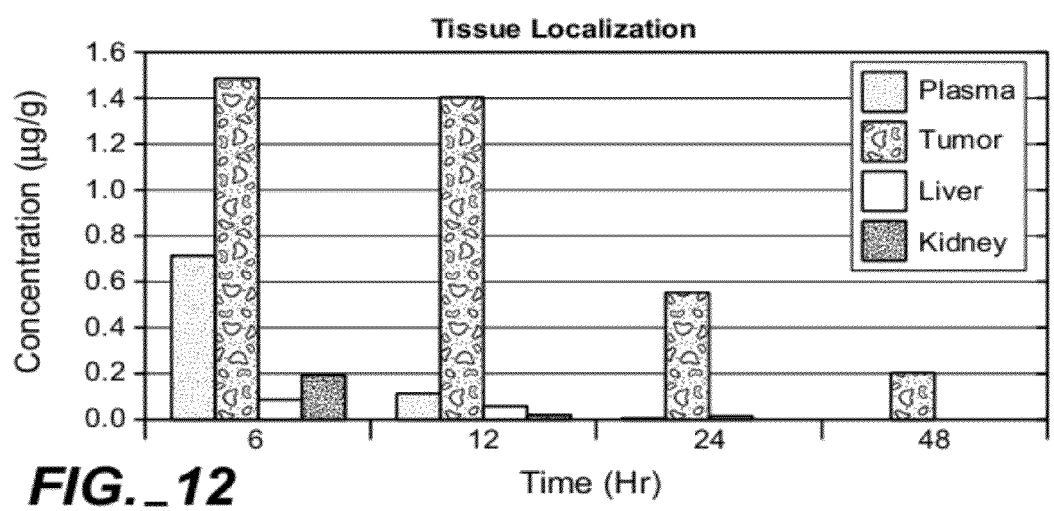
FIG._12

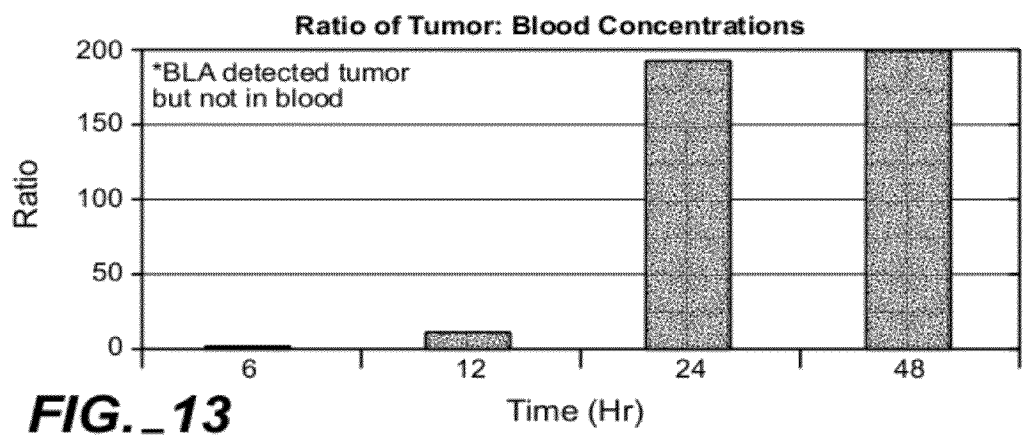
FIG._13
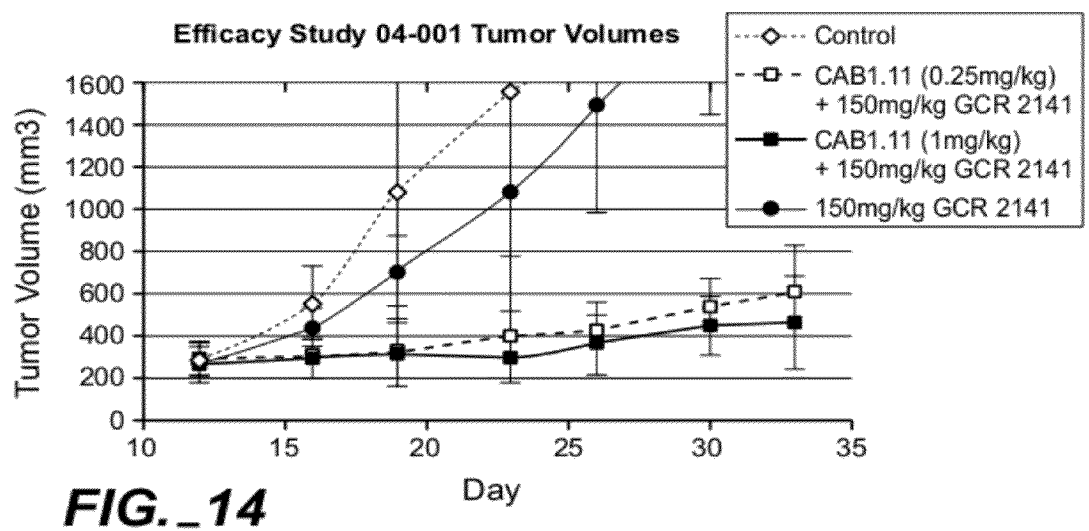
FIG._14

FIG._15A

| Case ID | ASM | Sample ID | Sample Pathology |
|---|---|---|---|
| CI0000000255 | DF5 | FR00005C7B | Adenocarcinoma of lung |
| CI0000005496 | FF5 | FR5B337147 | Adenocarcinoma of lung |
| CI0000011577 | FF1 | FR5B34059F | Adenocarcinoma of lung |
| CI7000000241 | AF4 | FR00033A78 | Adenocarcinoma of lung |
| CI0000007518 | AF5 | FR0001FD15 | Carcinoma of lung, squamous cell |
| CI0000008475 | HF4 | FR65EE0784 | Adenocarcinoma of colon, metastatic |
| CI0000015252 | FF2 | FR5B342166 | Adenocarcinoma of colon |

FIG._15B

| Case Diagnosis | Tissue of Origin/Site of Finding | H/E |
|---|---|---|
| Adenocarcinoma of lung<br>Grade: AJCC G3: Poorly differentiated<br>Stage: IIIA | Lung/Lung | 4X  20X |
| Adenocarcinoma of lung<br>Grade: AJCC G3: Poorly differentiated<br>Stage: IIIB | Lung/Lung | 4X  20X |
| Adenocarcinoma of lung<br>Grade: AJCC G2: Moderately differentiated<br>Stage: IIIA | Lung/Lung | 4X  20X |
| Adenocarcinoma of lung<br>Grade: AJCC G2: Moderately differentiated<br>Stage: IIIA | Lung/Lung | 4X  20X |
| Carcinoma of lung, squamous cell<br>Grade: AJCC G3: Poorly differentiated<br>Stage: IIIA | Lung/Lung | 4X  20X |
| Adenocarcinoma of colon, metastatic<br>Grade: Not Reported<br>Stage: IV | Colon/Liver | 4X  20X |
| Adenocarcinoma of colon<br>Grade: AJCC G3: Poorly differentiated<br>Stage: IIIB | Cecum/Cecum | 4X  20X |

FIG. 15C

| Anti-Human Cytokeratin AE1/AE3 | CAB/GCR3708 (0.2ug/ml) |
|---|---|
| Immunogencity: Tumor (100%, Variable to 3+ Cyto)<br>Necrosis (Variable to 3+ EC)<br>Specificity: High<br>4x　　　　　　　　20x<br>SF00029758 | Immunogencity: Tumor (100%, Variable to 3+ Cyto)<br>Mixed inflammatory cells (Variable to 1+ Cyto)<br>Specificity: High<br>4x　　　　　　　　20x<br>SF00029756 |
|  | Immunogencity: Tumor (15%, Variable to 3+ Cyto)<br>Intra-alveolar macrophages (Variable to 2+ Cyto)<br>Mixed inflammatory cells (Variable to 2+ Cyto)<br>Specificity: High<br>4x　　　　　　　　20x<br>SF0002975B |
|  | Immunogencity: Tumor (100%, 2+ Cyto)<br>Cellular stroma (1+ Cyto)<br>Chronic inflammatory cells (Variable to 1+ Cyto)<br>Specificity: High<br>4x　　　　　　　　20x<br>SF0002977F |
|  | Immunogencity: Tumor (75%, Variable to 3+ Cyto)<br>Cellular stroma (Variable to 2+ Cyto)<br>Necrosis (Variable to 2+ EC)<br>Intra-alveolar macrophages (Variable to 2+ Cyto)<br>Specificity: High<br>4x　　　　　　　　20x<br>SF0002978B |
|  | Immunogencity: Tumor (100%, 3+ Cyto)<br>Fibrotic stroma (1+ Cyto)<br>Necrosis (Variable to 3+ EC)<br>Specificity: High<br>4x　　　　　　　　20x<br>SF0002975F |
| Immunogencity: Tumor (98%, Variable to 3+<br>Mem, Variable to 3+ Cyto)<br>Fibrotic stroma (Variable to 1+ Cyto)<br>Normal liver parenchyma (2+ Cyto)<br>Necrosis (Variable to 3+ EC)<br>Specificity: High<br>4x　　　　　　　　20x<br>SF0002976A | Immunogencity: Tumor (95%, Variable to 3+<br>Mem, Variable to 3+ Cyto)<br>Fibrotic stroma (Variable to 1+ Cyto)<br>Normal liver parenchyma (1+ Cyto)<br>Necrosis (Variable to 3+ EC)<br>Specificity: High<br>4x　　　　　　　　20x<br>SF00029768<br>Normal liver parenchyma shows positive staining (1+) |
|  | Immunogencity: Tumor (85%, Variable to 3+<br>Mem, Variable to 3+ Cyto)<br>Cellular stroma (1+ Cyto)<br>Normal muscle (Variable to 2+ Cyto)<br>Specificity: High<br>4x　　　　　　　　20x<br>SF00029783 |

*FIG._15D*

| CAB/GCR5517 (0.2ug/ml) | CAB/GCR6798 (0.2ug/ml) |
|---|---|
| Immunogencity: Tumor (100%, Variable to 3+ Cyto)<br>Mixed inflammatory cells (Variable to 3+ Cyto)<br>Necrosis (Variable to 2+ EC)<br>Specificity: High<br>4x 20x<br>SF00029757 | Immunogencity: Tumor (100%, Variable to 3+ Cyto)<br>Mixed inflammatory cells (Variable to 1+ Cyto)<br>Specificity: High<br>4x 20x<br>SF00029753 |
| Immunogencity: Tumor (40%, Variable to 3+ Cyto)<br>Intra-alveolar macrophages (Variable to 2+ Cyto)<br>Mixed inflammatory cells (Variable to 2+ Cyto)<br>Specificity: High<br>4x 20x<br>SF0002975C | Immunogencity: Tumor (10%, Variable to 2+ Cyto)<br>Intra-alveolar macrophages (Variable to 2+ Cyto)<br>Mixed inflammatory cells (Variable to 2+ Cyto)<br>Specificity: High<br>4x 20x<br>SF00029759 |
| Immunogencity: Tumor (100%, 2+ Cyto)<br>Cellular stroma (1+ Cyto)<br>Chronic inflammatory cells (Variable to 1+ Cyto)<br>Specificity: High<br>4x 20x<br>SF00029780 | Immunogencity: Tumor (100%, 2+ Cyto)<br>Cellular stroma (1+ Cyto)<br>Chronic inflammatory cells (Variable to 1+ Cyto)<br>Specificity: High<br>4x 20x<br>SF0002977D |
| Immunogencity: Tumor (85%, Variable to 3+ Cyto)<br>Cellular stroma (Variable to 2+ Cyto)<br>Necrosis (Variable to 2+ EC)<br>Intra-alveolar macrophages (Variable to 2+ Cyto)<br>Specificity: High<br>4x 20x<br>SF0002978C | Immunogencity: Tumor (75%, Variable to 3+ Cyto)<br>Cellular stroma (Variable to 2+ Cyto)<br>Necrosis (Variable to 2+ EC)<br>Intra-alveolar macrophages (Variable to 2+ Cyto)<br>Specificity: High<br>4x 20x<br>SF00029789 |
| Immunogencity: Tumor (100%, 3+ Cyto)<br>Fibrotic stroma (1+ Cyto)<br>Necrosis (Variable to 3+ EC)<br>Specificity: High<br>4x 20x<br>SF00029760 | Immunogencity: Tumor (100%, 3+ Cyto)<br>Fibrotic stroma (1+ Cyto)<br>Necrosis (Variable to 3+ EC)<br>Specificity: High<br>4x 20x<br>SF0002975D |
| Immunogencity: Tumor (98%, Variable to 3+ Mem, Variable to 3+ Cyto)<br>Fibrotic stroma (Variable to 1+ Cyto)<br>Normal liver parenchyma (2+ Cyto)<br>Necrosis (Variable to 3+ EC)<br>Specificity: High<br>4x 20x<br>SF00029769 | Immunogencity: Tumor (95%, Variable to 3+ Mem, Variable to 3+ Cyto)<br>Fibrotic stroma (Variable to 1+ Cyto)<br>Normal liver parenchyma (1+ Cyto)<br>Necrosis (Variable to 3+ EC)<br>Specificity: High<br>4x 20x<br>SF00029765<br>Normal liver parenchyma shows positive staining (1+) |
| Immunogencity: Tumor (85%, Variable to 3+ Mem, Variable to 3+ Cyto)<br>Cellular stroma (1+ Cyto)<br>Normal muscle (Variable to 2+ Cyto)<br>Specificity: High<br>4x 20x<br>SF00029784 | Immunogencity: Tumor (95%, Variable to 3+ Mem, Variable to 3+ Cyto)<br>Cellular stroma (1+ Cyto)<br>Normal muscle (Variable to 2+ Cyto)<br>Specificity: High<br>4x 20x<br>SF00029781 |

FIG._15E

| CAB/GCR8886 (0.196ug/ml) | No Antibody Control (Prediluted) |
|---|---|
| Immunogencity: Tumor (100%, Variable to 3+ Cyto)<br>Mixed inflammatory cells (Variable to 1+ Cyto)<br>Specificity: High<br>4x　　　　　20x<br>SF00029754 | Immunogencity: N/A<br>Specificity: Unknown<br><br>SF00029755 |
| Immunogencity: Tumor (10%, Variable to 2+ Cyto)<br>Intra-alveolar macrophages (Variable to 2+ Cyto)<br>Mixed inflammatory cells (Variable to 2+ Cyto)<br>Specificity: High<br>4x　　　　　20x<br>SF0002975A | |
| Immunogencity: Tumor (100%, 2+ Cyto)<br>Cellular stroma (1+ Cyto)<br>Chronic inflammatory cells (Variable to 1+ Cyto)<br>Specificity: High<br>4x　　　　　20x<br>SF0002977E | |
| Immunogencity: Tumor (75%, Variable to 3+ Cyto)<br>Cellular stroma (Variable to 2+ Cyto)<br>Necrosis (Variable to 2+ EC)<br>Intra-alveolar macrophages (Variable to 2+ Cyto)<br>Specificity: High<br>4x　　　　　20x<br>SF0002978A | |
| Immunogencity: Tumor (100%, 3+ Cyto)<br>Fibrotic stroma (1+ Cyto)<br>Necrosis (Variable to 3+ EC)<br>Specificity: High<br>4x　　　　　20x<br>SF0002975E | |
| Immunogencity: Tumor (95%, Variable to 3+<br>Mem, Variable to 3+ Cyto)<br>Fibrotic stroma (Variable to 1+ Cyto)<br>Normal liver parenchyma (1+ Cyto)<br>Necrosis (Variable to 3+ EC)<br>Specificity: High<br>4x　　　　　20x<br>SF00029766<br>Normal liver parenchyma shows positive staining (1+) | Immunogencity: N/A<br>Specificity: Unknown<br><br>SF00029767 |
| Immunogencity: Tumor (95%, Variable to 3+<br>Mem, Variable to 3+ Cyto)<br>Cellular stroma (1+ Cyto)<br>Normal muscle (Variable to 2+ Cyto)<br>Specificity: High<br>4x　　　　　20x<br>SF00029782 | |

| | | | |
|---|---|---|---|
| CI0000017970 | HF1 | FR65EE7B3D | Adenocarcinoma of colon |
| CI0000010013 | AF2 | FR00028F2E | Adenocarcinoma of pancreas, metastatic |
| CI0000009651 | AF1 | FR0002B111 | Adenocarcinoma of pancreas, ductal |
| CI0000008690 | CF4 | FR00027B0E | Adenocarcinoma of pancreas, ductal |
| CI0000007678 | AF3 | FR0002575B | Adenocarcinoma of pancreas, ductal |
| CI0000009736 | AF2 | FR0002BAB4 | Adenocarcinoma of pancreas, ductal |

*FIG._15F*

| | | |
|---|---|---|
| Adenocarcinoma of colon<br>Grade: AJCC G3: Moderately differentiated<br>Stage: IIIC | Colon/Colon | 4X  20X |
| Adenocarcinoma of pancreas, metastatic<br>Grade: Not Reported<br>Stage: IV | Pancreas/Omentum | 4X  20X |
| Adenocarcinoma of pancreas, ductal<br>Grade: AJCC G2: Moderately differentiated<br>Stage: IIB | Pancreas/Pancreas | 4X  20X |
| Adenocarcinoma of pancreas, ductal<br>Grade: AJCC G1: Well differentiated<br>Stage: IIA | Pancreas/Pancreas | 4X  20X |
| Adenocarcinoma of pancreas, ductal<br>Grade: AJCC G2: Moderately differentiated<br>Stage: III | Pancreas/Pancreas | 4X  20X |
| Adenocarcinoma of pancreas, ductal<br>Grade: AJCC G2: Moderately differentiated<br>Stage: IIB | Pancreas/Pancreas | 4X  20X |

*FIG._15G*

| | Immunogencity: Tumor (100%, 3+ Cyto)<br>Cellular stroma (1+ Cyto)<br>Necrosis (Variable to 3+ EC)<br>Specificity: High<br>4x      20x<br>SF00029787 |
|---|---|
| Immunogencity: Tumor (100%, 3+ Cyto)<br>Fibroadipose tissue (Variable to 1+ Cyto)<br>Specificity: High<br>4x      20x<br>SF0002977C | Immunogencity: Tumor (100%, 3+ Cyto)<br>Fibroadipose tissue (Variable to 2+ Cyto)<br>Specificity: High<br>4x      20x<br>SF0002977A |
| | Immunogencity: Tumor (100%, 3+ Cyto)<br>Desmoplastic stroma (Variable to 2+ Cyto)<br>Specificity: High<br>4x      20x<br>SF00029771 |
| | Immunogencity: Tumor (100%, 3+ Cyto)<br>Myxoid stroma (Variable to 2+ Cyto)<br>Specificity: High<br>4x      20x<br>SF0002976D |
| | Immunogencity: Tumor (85%, Variable to 3+ Cyto)<br>Cellular stroma (Variable to 1+ Cyto)<br>Chronic pancreatitis (Variable to 1+ Cyto)<br>Specificity: High<br>4x      20x<br>SF00029763 |
| | Immunogencity: Tumor (100%, 3+ Cyto)<br>Chronic pancreatitis (Variable to 2+ Cyto)<br>Fibrotic stroma (Variable to 2+ Cyto)<br>Specificity: High<br>4x      20x<br>SF00029775 |

*FIG._15H*

| Immunogencity: Tumor (100%, 3+ Cyto)<br>Cellular stroma (1+ Cyto)<br>Necrosis (Variable to 3+ EC)<br>Specificity: High<br>4x                20x<br>SF00029788 | Immunogencity: Tumor (100%, 3+ Cyto)<br>Cellular stroma (1+ Cyto)<br>Necrosis (Variable to 3+ EC)<br>Specificity: High<br>4x                20x<br>SF00029785 |
|---|---|
| Immunogencity: Tumor (100%, 3+ Cyto)<br>Fibroadipose tissue (Variable to 2+ Cyto)<br>Specificity: High<br>4x                20x<br>SF0002977B | Immunogencity: Tumor (100%, 3+ Cyto)<br>Fibroadipose tissue (Variable to 2+ Cyto)<br>Specificity: High<br>4x                20x<br>SF00029777 |
| Immunogencity: Tumor (100%, 3+ Cyto)<br>Desmoplastic stroma (Variable to 2+ Cyto)<br>Specificity: High<br>4x                20x<br>SF00029772 | Immunogencity: Tumor (100%, 3+ Cyto)<br>Desmoplastic stroma (Variable to 2+ Cyto)<br>Specificity: High<br>4x                20x<br>SF00029770 |
| Immunogencity: Tumor (100%, 3+ Cyto)<br>Myxoid stroma (Variable to 2+ Cyto)<br>Specificity: High<br>4x                20x<br>SF0002976E | Immunogencity: Tumor (100%, 3+ Cyto)<br>Myxoid stroma (Variable to 2+ Cyto)<br>Specificity: High<br>4x                20x<br>SF0002976B |
| Immunogencity: Tumor (85%, Variable to 3+ Cyto)<br>Cellular stroma (Variable to 1+ Cyto)<br>Chronic pancreatitis (Variable to 1+ Cyto)<br>Specificity: High<br>4x                20x<br>SF00029764 | Immunogencity: Tumor (85%, Variable to 3+ Cyto)<br>Cellular stroma (Variable to 1+ Cyto)<br>Chronic pancreatitis (Variable to 1+ Cyto)<br>Specificity: High<br>4x                20x<br>SF00029761 |
| Immunogencity: Tumor (100%, 3+ Cyto)<br>Chronic pancreatitis (Variable to 2+ Cyto)<br>Fibrotic stroma (Variable to 2+ Cyto)<br>Specificity: High<br>4x                20x<br>SF00029776 | Immunogencity: Tumor (100%, 3+ Cyto)<br>Chronic pancreatitis (Variable to 1+ Cyto)<br>Fibrotic stroma (Variable to 1+ Cyto)<br>Specificity: High<br>4x                20x<br>SF00029773 |

FIG._15I

| | |
|---|---|
| Immunogencity: Tumor (100%, 3+ Cyto)<br>Cellular stroma (1+ Cyto)<br>Necrosis (Variable to 3+ EC)<br>Specificity: High<br>4x              20x<br>SF00029786 | |
| Immunogencity: Tumor (100%, 3+ Cyto)<br>Fibroadipose tissue (Variable to 2+ Cyto)<br>Specificity: High<br>4x              20x<br>SF00029778 | Immunogencity: N/A<br>Specificity: N/A<br><br>SF00029779 |
| Immunogencity: Tumor (100%, 3+ Cyto)<br>Desmoplastic stroma (Variable to 2+ Cyto)<br>Specificity: High<br>4x              20x<br>SF0002976F | |
| Immunogencity: Tumor (100%, 3+ Cyto)<br>Myxoid stroma (Variable to 2+ Cyto)<br>Specificity: High<br>4x              20x<br>SF0002976C | |
| Immunogencity: Tumor (85%, Variable to 3+ Cyto)<br>Cellular stroma (Variable to 1+ Cyto)<br>Chronic pancreatitis (Variable to 1+ Cyto)<br>Specificity: High<br>4x              20x<br>SF00029762 | |
| Immunogencity: Tumor (100%, 3+ Cyto)<br>Chronic pancreatitis (Variable to 2+ Cyto)<br>Fibrotic stroma (Variable to 2+ Cyto)<br>Specificity: High<br>4x              20x<br>SF00029774 | |

*FIG._15J*

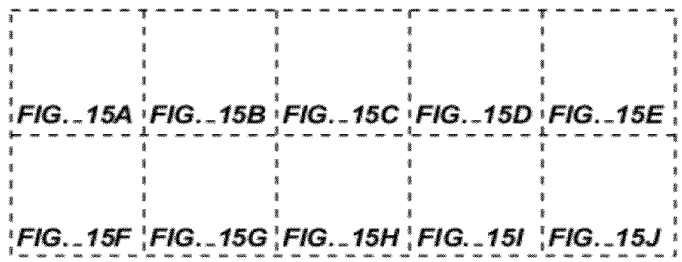

*FIG._15*

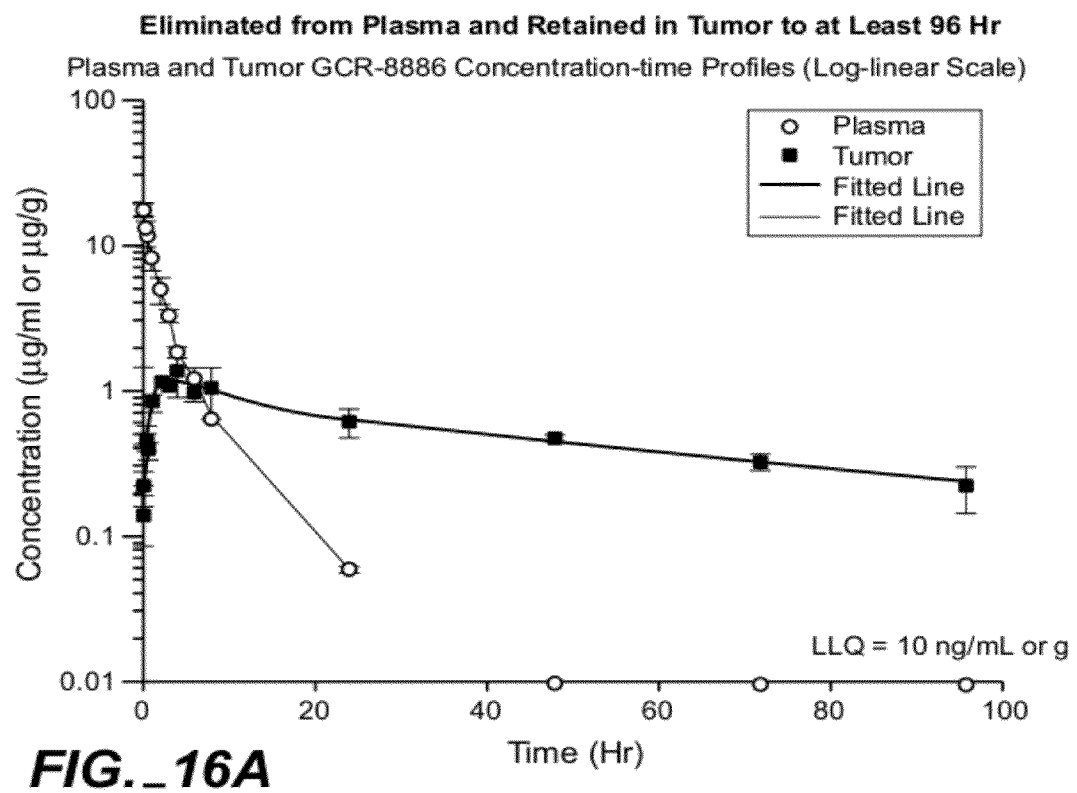
FIG._16A

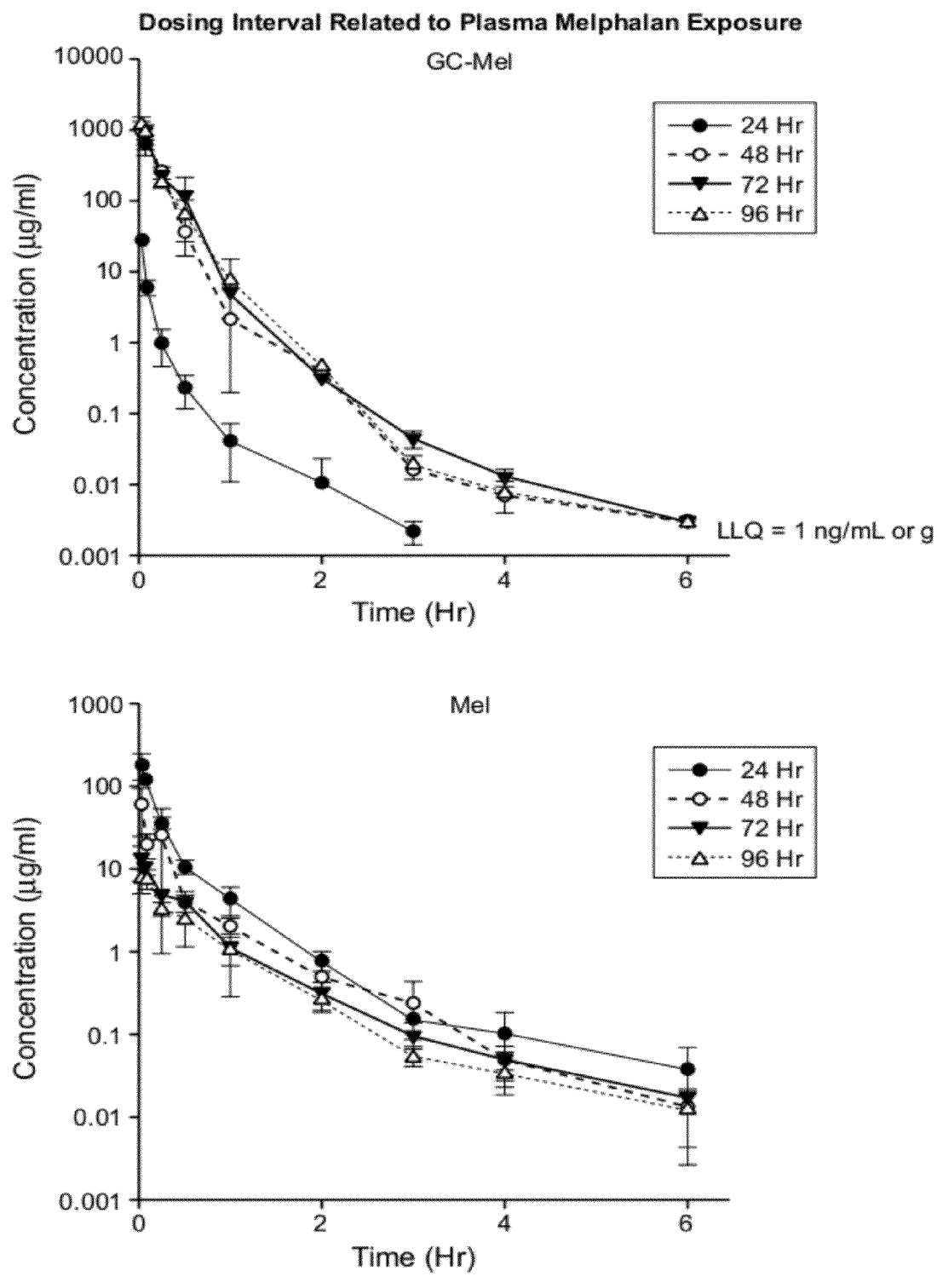
FIG._16B-1

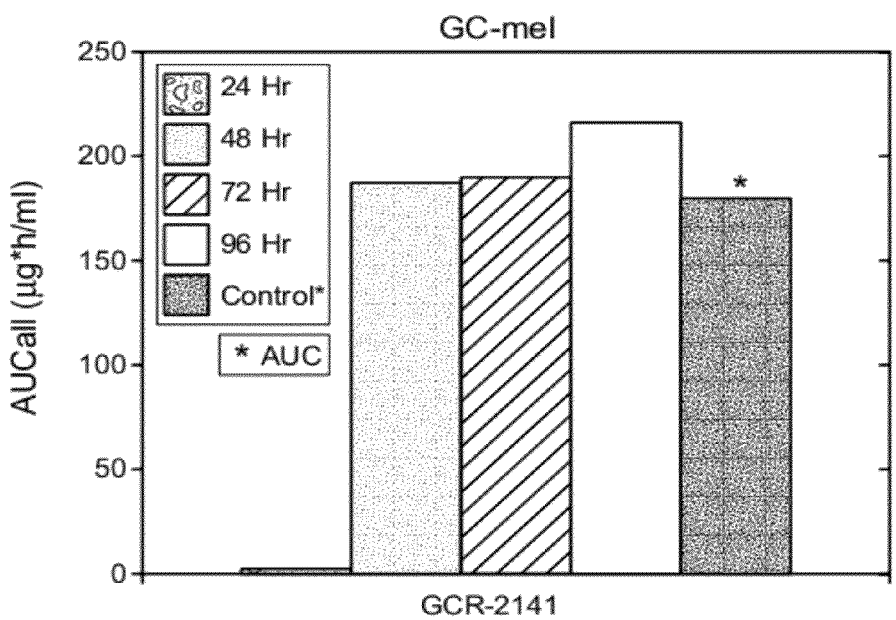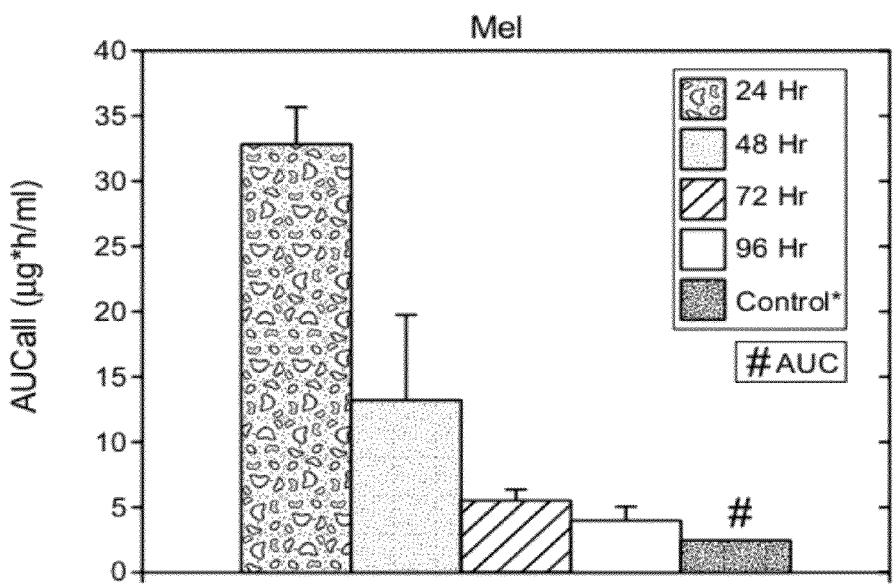
FIG._16B-2

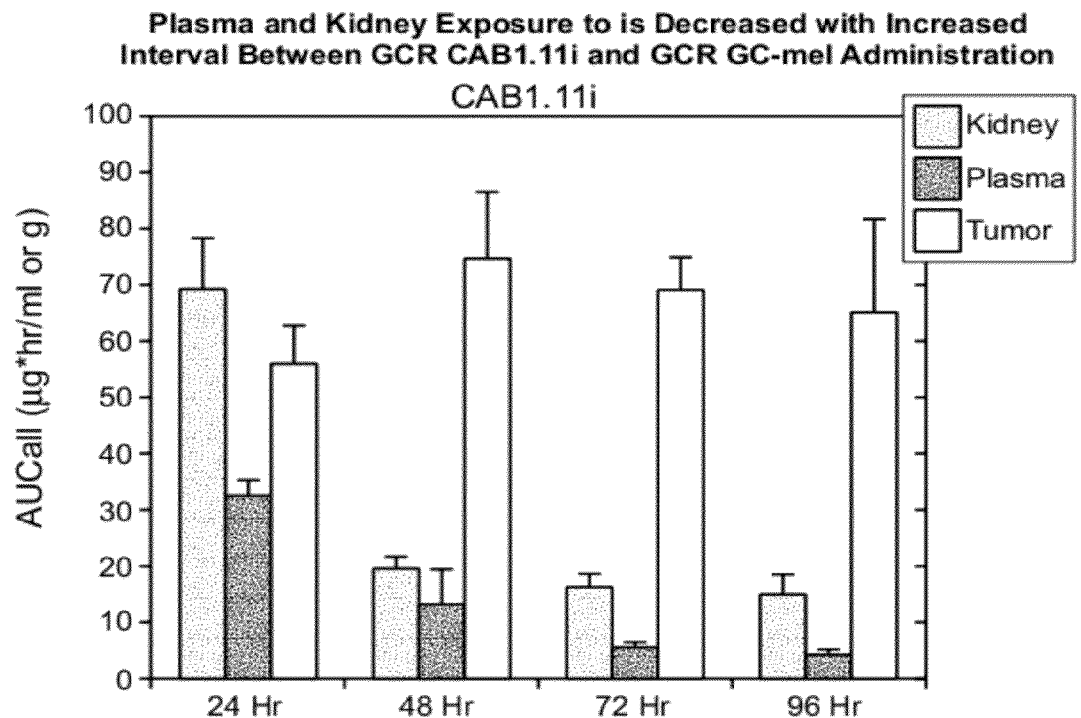
FIG._17
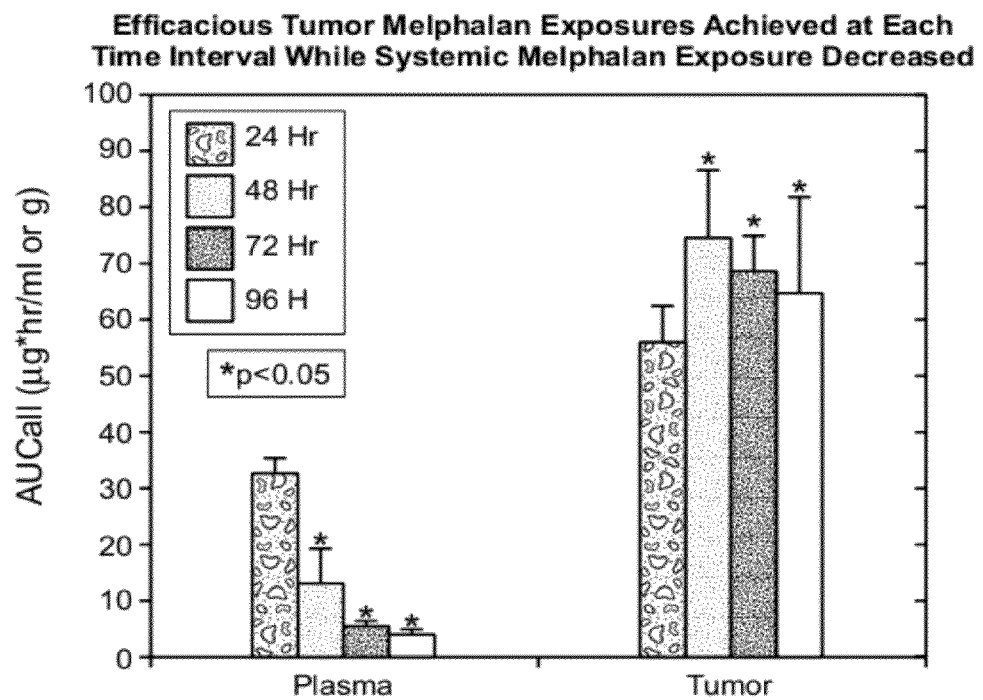
FIG._18

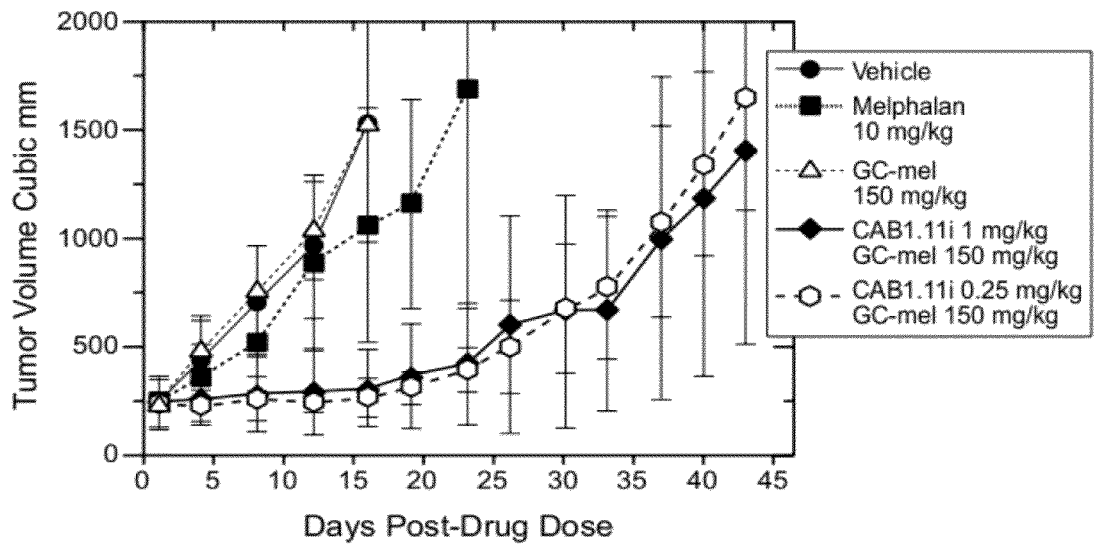
FIG._19A
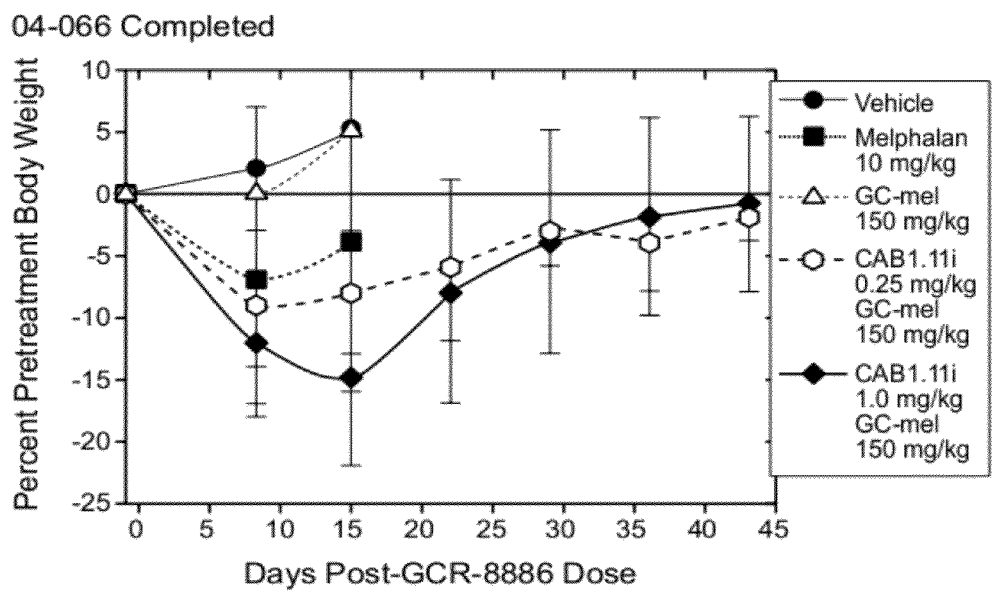
FIG._19B

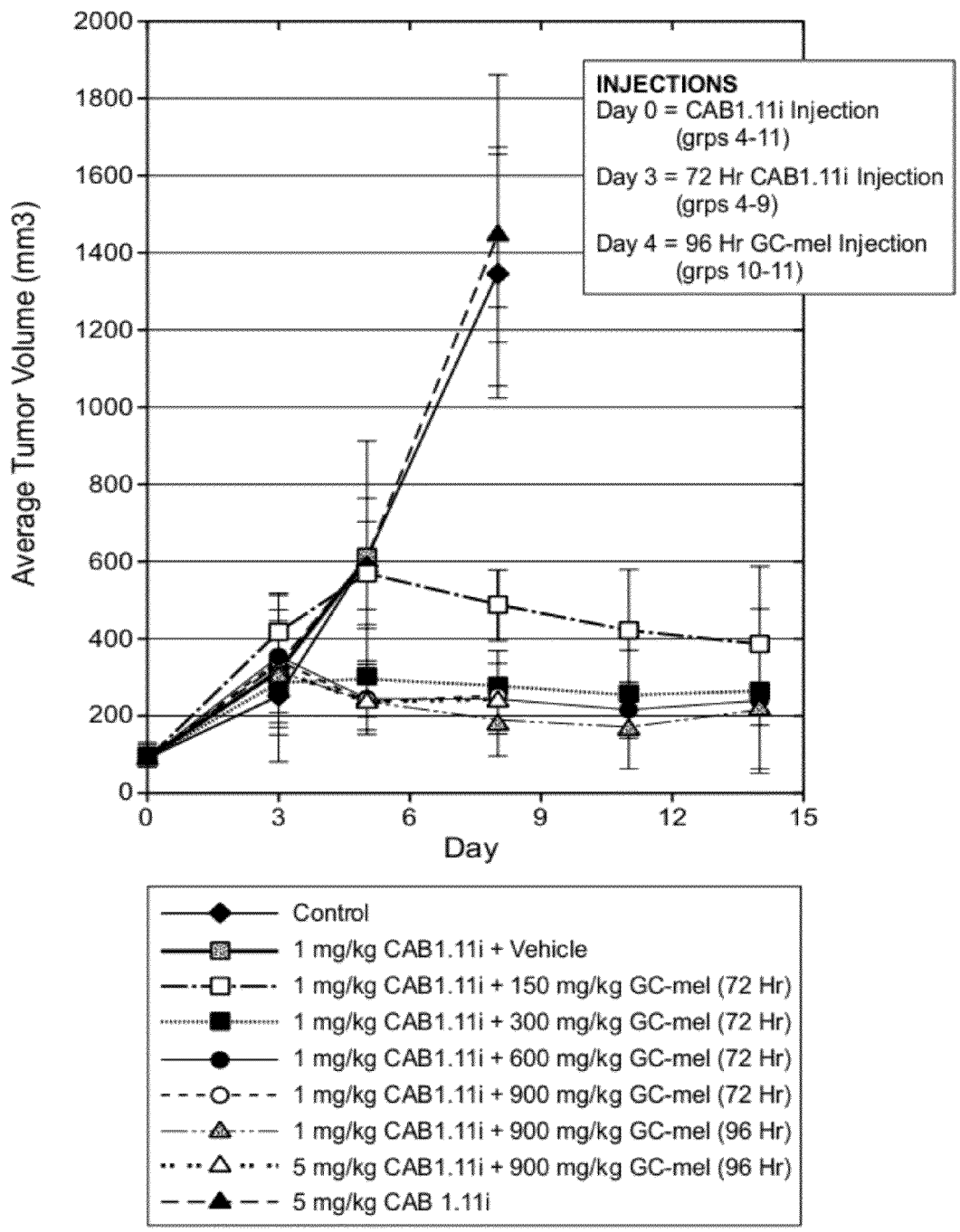
FIG._21

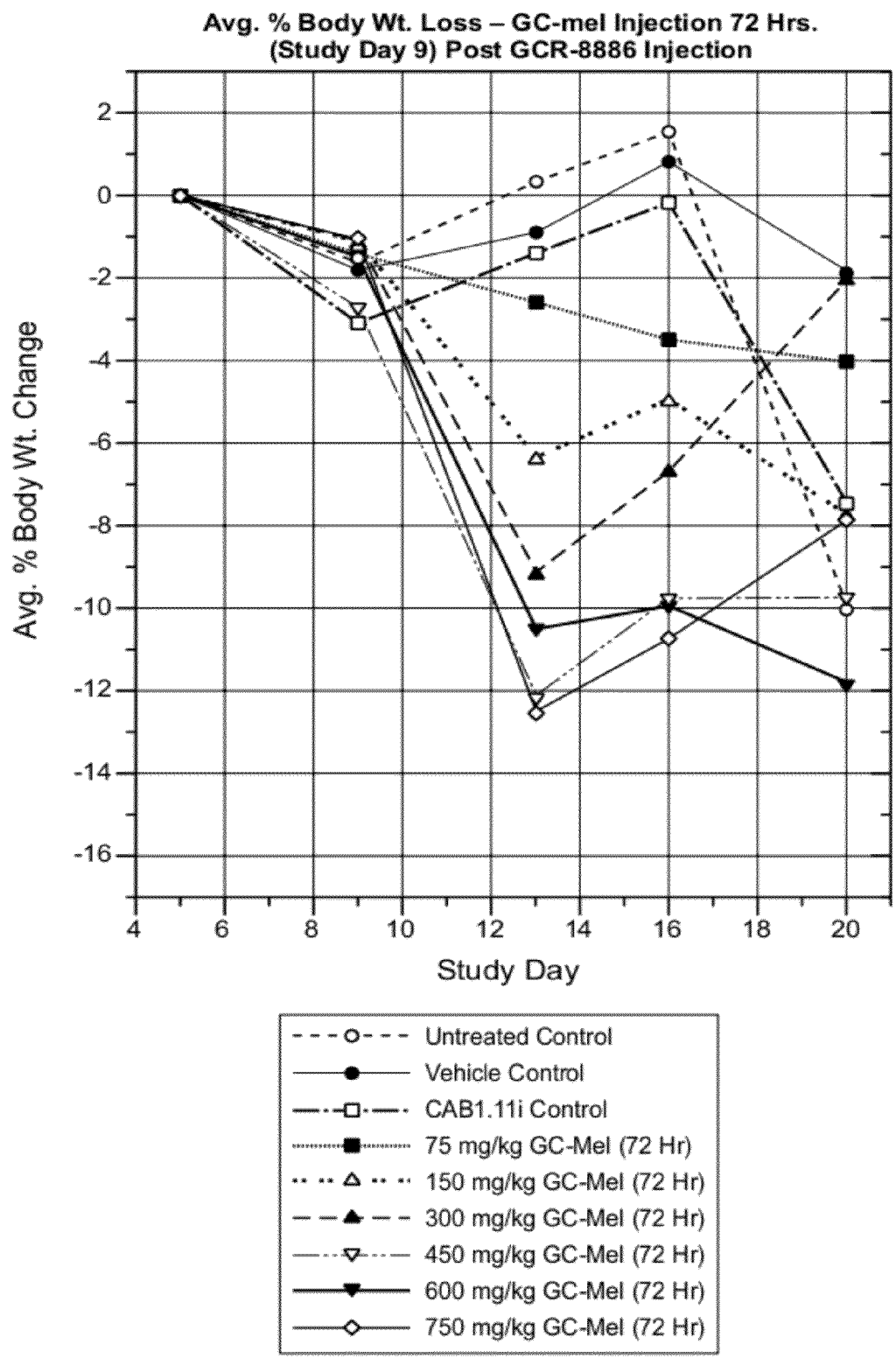
FIG._22A

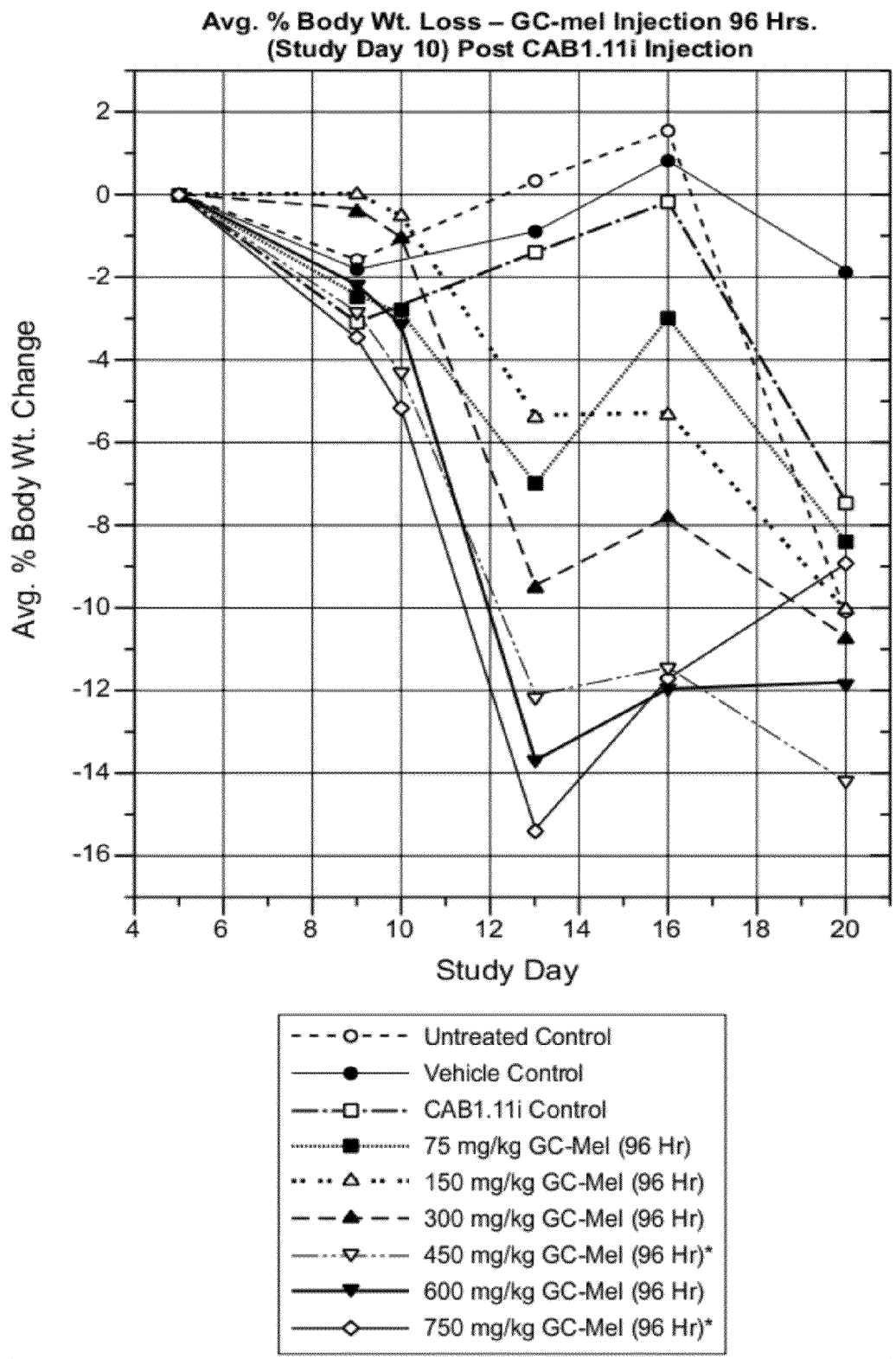
FIG._22B

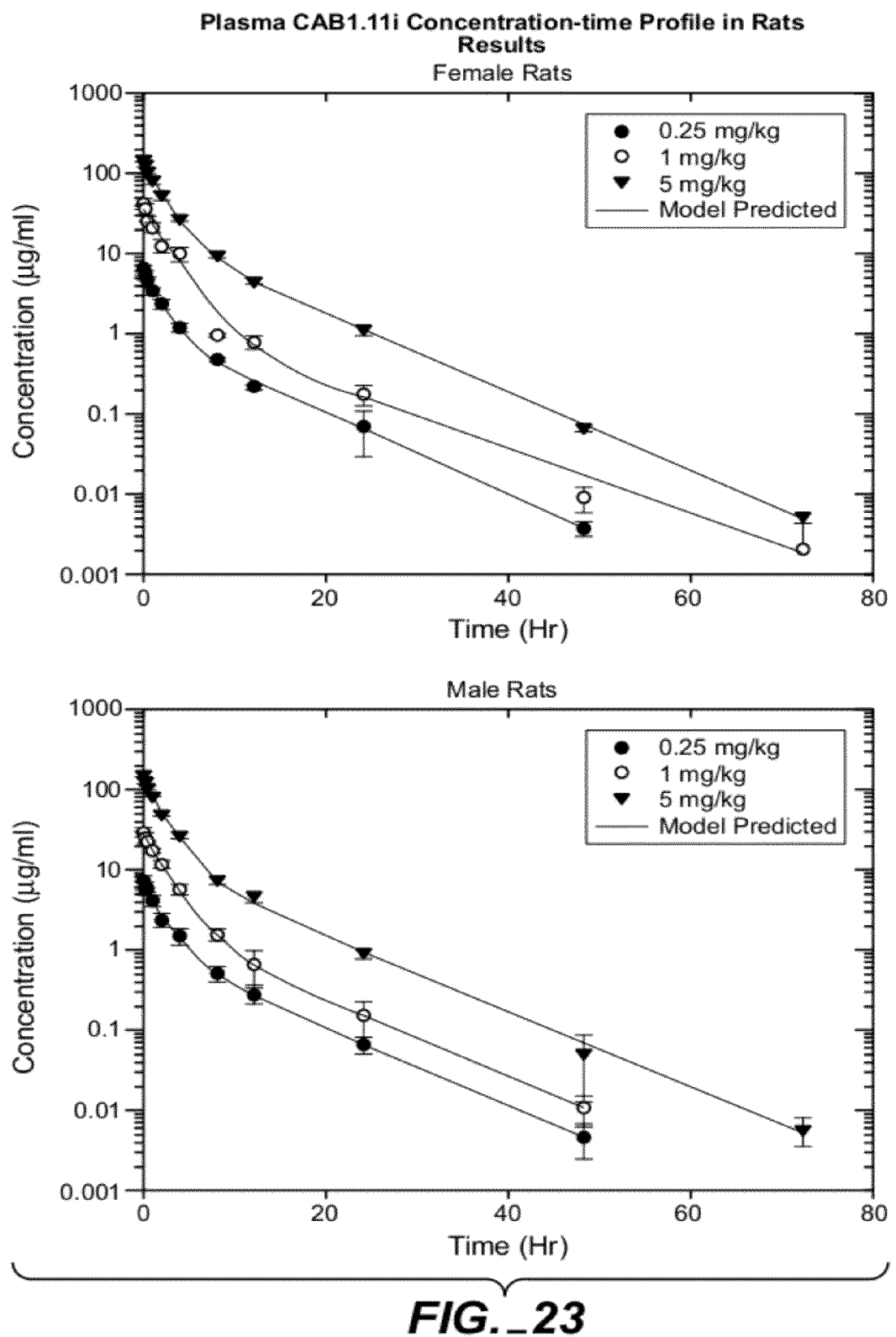
FIG._23

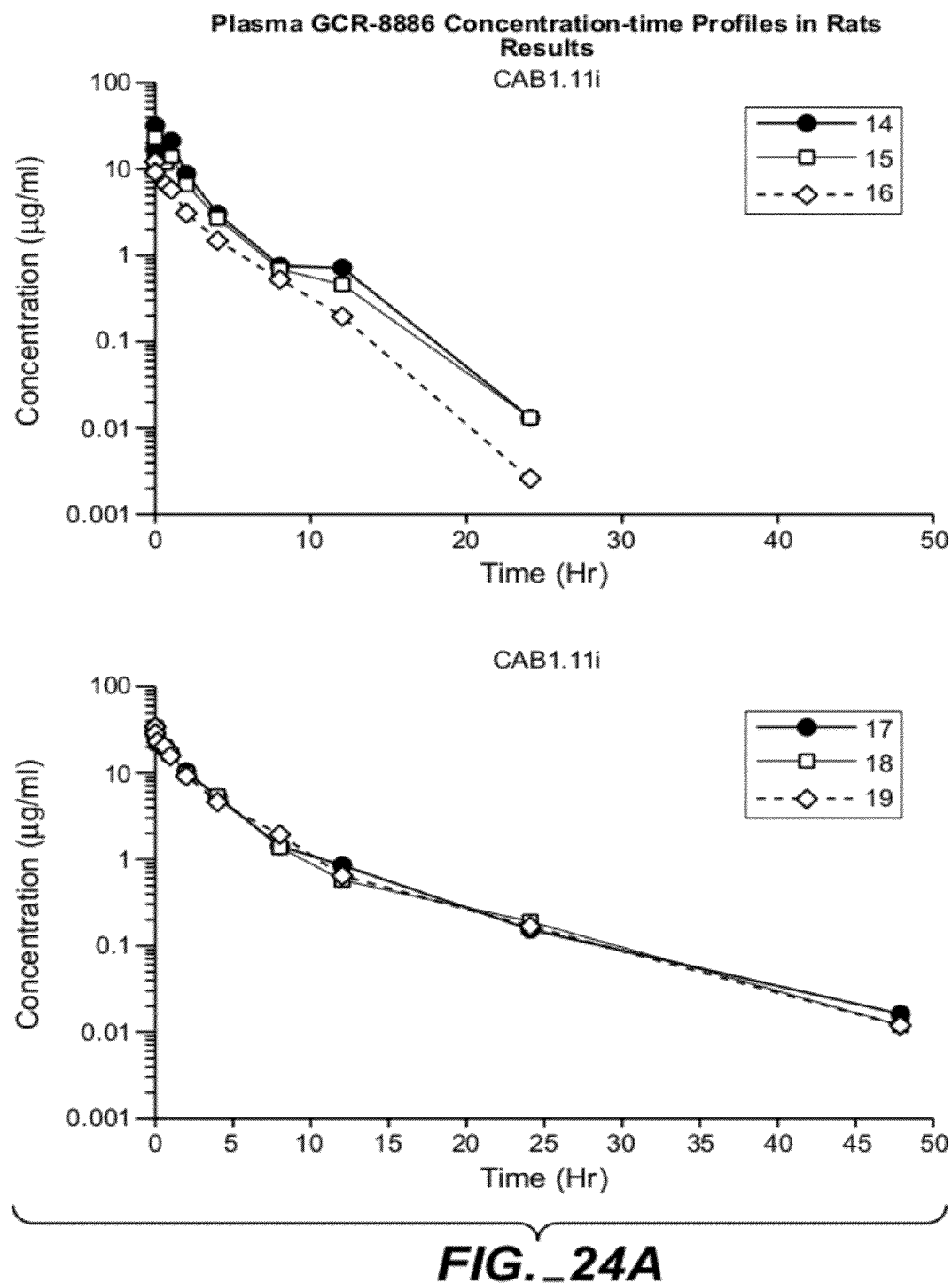
FIG._24A

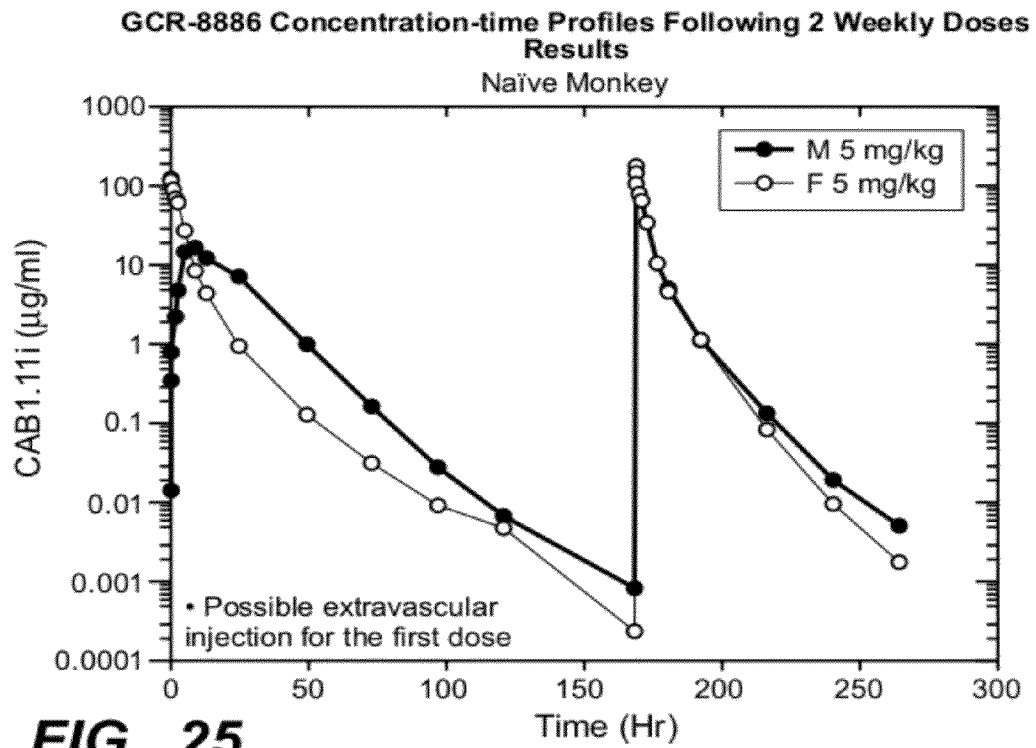
FIG._25
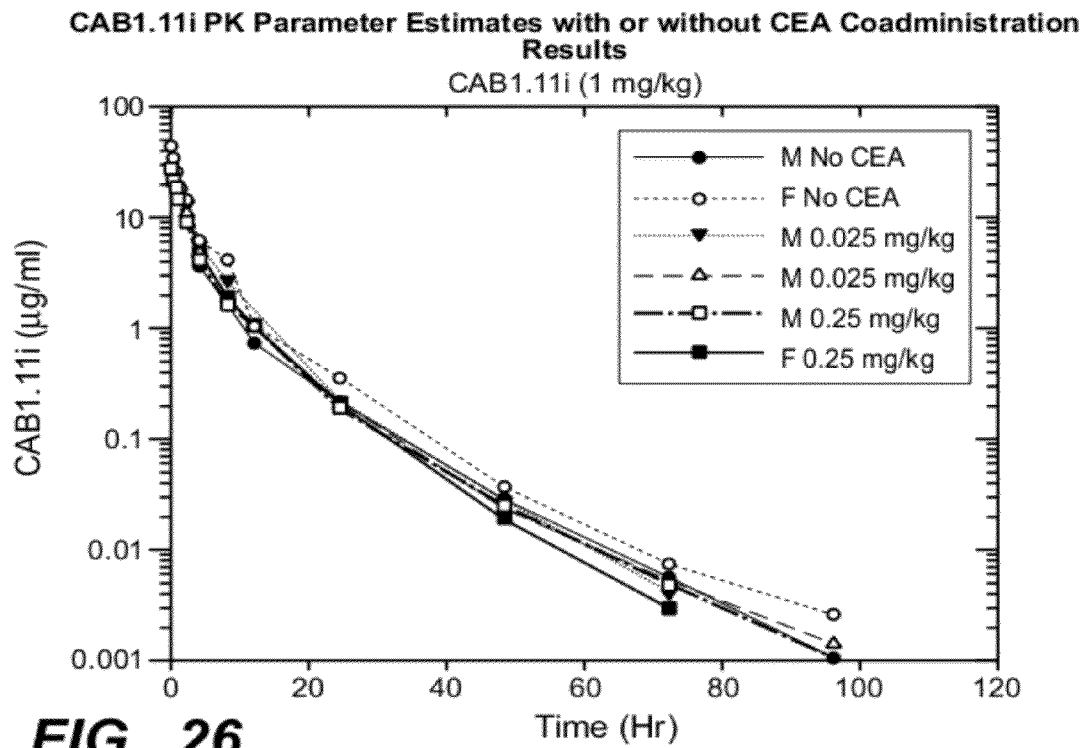
FIG._26

US 8,728,470 B2

SEQUENCE LISTING

```
<160> NUMBER OF SEQ ID NOS: 51

<210> SEQ ID NO 1
<211> LENGTH: 262
<212> TYPE: PRT
<213> ORGANISM: Artificial Sequence
<220> FEATURE:
<223> OTHER INFORMATION: engineered T84.66 antibody

<400> SEQUENCE: 1

Asp Ile Val Leu Thr Gln Ser Pro Ala Ser Leu Ala Val Ser Leu Gly
1               5                   10                  15

Gln Arg Ala Thr Met Ser Cys Arg Ala Gly Glu Ser Val Asp Ile Phe
            20                  25                  30

Gly Val Gly Phe Leu His Trp Tyr Gln Gln Lys Pro Gly Gln Pro Pro
        35                  40                  45

Lys Leu Leu Ile Tyr Arg Ala Ser Asn Leu Glu Ser Gly Ile Pro Val
    50                  55                  60

Arg Phe Ser Gly Thr Gly Ser Arg Thr Asp Phe Thr Leu Ile Ile Asp
65                  70                  75                  80

Pro Val Glu Ala Asp Asp Val Ala Thr Tyr Tyr Cys Gln Gln Thr Asn
                85                  90                  95

Glu Asp Pro Tyr Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gly Gly
        115                 120                 125

Gly Gly Ser Gly Gly Gly Gly Ser Gly Gly Gly Gly Ser Glu Val Gln
    130                 135                 140

Leu Gln Gln Ser Gly Ala Glu Leu Val Glu Pro Gly Ala Ser Val Lys
145                 150                 155                 160

Leu Ser Cys Thr Ala Ser Gly Phe Asn Ile Lys Asp Thr Tyr Met His
                165                 170                 175

Trp Val Lys Gln Arg Pro Glu Gln Gly Leu Glu Trp Ile Gly Arg Ile
            180                 185                 190

Asp Pro Ala Asn Gly Asn Ser Lys Tyr Val Pro Lys Phe Gln Gly Lys
        195                 200                 205

Ala Thr Ile Thr Ala Asp Thr Ser Ser Asn Thr Ala Tyr Leu Gln Leu
    210                 215                 220

Thr Ser Leu Thr Ser Glu Asp Thr Ala Val Tyr Tyr Cys Ala Pro Phe
225                 230                 235                 240

Gly Tyr Tyr Val Ser Asp Tyr Ala Met Ala Tyr Trp Gly Gln Gly Thr
                245                 250                 255

Ser Val Thr Val Ser Ser
            260
```

<210> SEQ ID NO 2
<211> LENGTH: 623
<212> TYPE: PRT
<213> ORGANISM: Artificial Sequence
<220> FEATURE:
<223> OTHER INFORMATION: CAB 1.10 construct

<400> SEQUENCE: 2

```
Asp Ile Val Leu Thr Gln Ser Pro Ala Ser Leu Ala Val Ser Leu Gly
1               5                   10                  15

Gln Arg Ala Thr Met Ser Cys Arg Ala Gly Glu Ser Val Asp Ile Phe
            20                  25                  30

Gly Val Gly Phe Leu His Trp Tyr Gln Gln Lys Pro Gly Gln Pro Pro
        35                  40                  45

Lys Leu Leu Ile Tyr Arg Ala Ser Asn Leu Glu Ser Gly Ile Pro Val
    50                  55                  60

Arg Phe Ser Gly Thr Gly Ser Arg Thr Asp Phe Thr Leu Ile Ile Asp
65                  70                  75                  80

Pro Val Glu Ala Asp Asp Val Ala Thr Tyr Tyr Cys Gln Gln Thr Asn
                85                  90                  95

Glu Asp Pro Tyr Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gly Gly
        115                 120                 125

Gly Gly Ser Gly Gly Gly Gly Ser Gly Gly Gly Gly Ser Glu Val Gln
    130                 135                 140

Leu Gln Gln Ser Gly Ala Glu Leu Val Glu Pro Gly Ala Ser Val Lys
145                 150                 155                 160

Leu Ser Cys Thr Ala Ser Gly Phe Asn Ile Lys Asp Thr Tyr Met His
                165                 170                 175

Trp Val Lys Gln Arg Pro Glu Gln Gly Leu Glu Trp Ile Gly Arg Ile
            180                 185                 190

Asp Pro Ala Asn Gly Asn Ser Lys Tyr Val Pro Lys Phe Gln Gly Lys
        195                 200                 205

Ala Thr Ile Thr Ala Asp Thr Ser Ser Asn Thr Ala Tyr Leu Gln Leu
    210                 215                 220

Thr Ser Leu Thr Ser Glu Asp Thr Ala Val Tyr Tyr Cys Ala Pro Phe
225                 230                 235                 240

Gly Tyr Tyr Val Ser Asp Tyr Ala Met Ala Tyr Trp Gly Gln Gly Thr
                245                 250                 255

Ser Val Thr Val Ser Ser Thr Pro Val Ser Lys Gln Leu Ala Glu
            260                 265                 270

Val Val Ala Asn Thr Ile Thr Pro Leu Met Lys Ala Gln Ser Val Pro
        275                 280                 285

Gly Met Ala Val Ala Val Ile Tyr Gln Gly Lys Pro His Tyr Tyr Thr
    290                 295                 300

Phe Gly Lys Ala Asp Ile Ala Ala Asn Lys Pro Val Thr Pro Gln Thr
305                 310                 315                 320

Leu Phe Glu Leu Gly Ser Ile Ser Lys Thr Phe Thr Gly Val Leu Gly
                325                 330                 335

Gly Asp Ala Ile Ala Arg Gly Glu Ile Ser Leu Asp Asp Ala Val Thr
            340                 345                 350

Arg Tyr Trp Pro Gln Leu Thr Gly Lys Gln Trp Gln Gly Ile Arg Met
        355                 360                 365

Leu Asp Leu Ala Thr Tyr Thr Ala Gly Gly Leu Pro Leu Gln Val Pro
    370                 375                 380
```

```
Asp Glu Val Thr Asp Asn Ala Ser Leu Leu Arg Phe Tyr Gln Asn Trp
385                 390                 395                 400

Gln Pro Gln Trp Lys Pro Gly Thr Thr Arg Leu Tyr Ala Asn Ala Ser
            405                 410                 415

Ile Gly Leu Phe Gly Ala Leu Ala Val Lys Pro Ser Gly Met Pro Tyr
        420                 425                 430

Glu Gln Ala Met Thr Thr Arg Val Leu Lys Pro Leu Lys Leu Asp His
            435                 440                 445

Thr Trp Ile Asn Val Pro Lys Ala Glu Glu Ala His Tyr Ala Trp Gly
        450                 455                 460

Tyr Arg Asp Gly Lys Ala Val Arg Val Ser Pro Gly Met Leu Asp Ala
465                 470                 475                 480

Gln Ala Tyr Gly Val Lys Thr Asn Val Gln Asp Met Ala Asn Trp Val
            485                 490                 495

Met Ala Asn Met Ala Pro Glu Asn Val Ala Asp Ala Ser Leu Lys Gln
        500                 505                 510

Gly Ile Ala Leu Ala Gln Ser Arg Tyr Trp Arg Ile Gly Ser Met Tyr
        515                 520                 525

Gln Gly Leu Gly Trp Glu Met Leu Asn Trp Pro Val Glu Ala Asn Thr
        530                 535                 540

Val Val Glu Thr Ser Phe Gly Asn Val Ala Leu Ala Pro Leu Pro Val
545                 550                 555                 560

Ala Glu Val Asn Pro Ala Pro Pro Val Lys Ala Ser Trp Val His
            565                 570                 575

Lys Thr Gly Ser Thr Gly Gly Phe Gly Ser Tyr Val Ala Phe Ile Pro
            580                 585                 590

Glu Lys Gln Ile Gly Ile Val Met Leu Ala Asn Thr Ser Tyr Pro Asn
            595                 600                 605

Pro Ala Arg Val Glu Ala Ala Tyr His Ile Leu Glu Ala Leu Gln
    610                 615                 620

<210> SEQ ID NO 3
<211> LENGTH: 786
<212> TYPE: DNA
<213> ORGANISM: Artificial Sequence
<220> FEATURE:
<223> OTHER INFORMATION: engineered T84.66 antibody

<400> SEQUENCE: 3
gacatcgtcc tgacccagag cccggcaagc ctggctgttt ccctgggcca gcgtgccact     60
atgtcctgca gagcgggtga gtctgttgac attttcggtg tcggttttct gcactggtac    120
caacagaaac cgggtcagcc gccaaaactg ctgatctatc gtgcttctaa cctggagtcc    180
ggcatcccgg tacgtttctc cggtactggc tctcgtactg attttaccct gattatcgac    240
ccggtggaag cagacgatgt tgccacctac tattgccagc agaccaacga ggatccgtac    300
accttcggtg gcggtactaa actggagatc aaaggcggtg gtggttctgg tggtggtggt    360
agcggcggcg gtggtagcgg tggcggttgg cagcggtggtg gtggctctgg tggcggtggc    420
tctgaagtgc agctgcagca gtccggtgcg gagctcgttg aaccgggcgc ttctgtgaaa    480
ctgtcttgca ctgcatctgg tttcaacatt aaggacacct acatgcactg ggtgaaacaa    540
cgcccggaac agggtctgga gtggatcggt cgcatcgatc cggctaacgg taacagcaaa    600
tacgtgccaa aattccaggg taaagcaacc atcactgctg atacctcctc taacactgct    660
tacctgcagc tgacttccct gactagcgaa gacaccgcgg tttattactg cgctccgttc    720
```

-continued

```
ggctactatg tcagcgatta cgcaatggcc tactggggtc agggcacctc tgttaccgtt      780
tctagc                                                                786

<210> SEQ ID NO 4
<211> LENGTH: 1869
<212> TYPE: DNA
<213> ORGANISM: Artificial Sequence
<220> FEATURE:
<223> OTHER INFORMATION: CAB 1.10 construct

<400> SEQUENCE: 4
gacatcgtcc tgacccagag cccggcaagc ctggctgttt ccctgggcca gcgtgccact       60
atgtcctgca gagcgggtga gtctgttgac attttcggtg tcggttttct gcactggtac      120
caacagaaac cggtcagcc gccaaaactg ctgatctatc gtgcttctaa cctggagtcc       180
ggcatcccgg tacgtttctc cggtactggc tctcgtactg attttaccct gattatcgac      240
ccggtggaag cagacgatgt tgccacctac tattgccagc agaccaacga ggatccgtac      300
accttcggtg gcggtactaa actggagatc aaaggcggtg gtggttctgg tggtggtggt      360
agcggcggcg gtggtagcgg tggcggtggc agcggtggtg gtggctctgg tggcggtggc      420
tctgaagtgc agctgcagca gtccggtgcg gagctcgttg aaccgggcgc ttctgtgaaa      480
ctgtcttgca ctgcatctgg tttcaacatt aaggacacct acatgcactg ggtgaaacaa      540
cgcccggaac agggtctgga gtggatcggt cgcatcgatc cggctaacgg taacagcaaa      600
tacgtgccaa aattccaggg taaagcaacc atcactgctg atacctcctc taacactgct      660
tacctgcagc tgacttccct gactagcgaa gacaccgcgg tttattactg cgctccgttc      720
ggctactatg tcagcgatta cgcaatggcc tactggggtc agggcacctc tgttaccgtt      780
tctagcacac cggtgtcaga aaacagctg gcggaggtgt cgcgaatac gattaccccg       840 ctgatgaaag cccagtctgt tccaggcatg gcggtggccg ttatttatca gggaaaaccg      900
cactattaca catttggcaa ggccgatatc gcggcgaata aacccgttac gcctcagacc      960
ctgttcgagc tgggttctat aagtaaaaac ttcaccggcg ttttaggtgg ggatgccatt     1020
gctcgcggtg aaatttcgct ggacgatgcg gtgaccagat actggccaca gctgacgggc     1080
aagcagtggc agggtattcg tatgctggat ctcgccacct acaccgctgg cggcctgccg     1140
ctacaggtac cggatgaggt cacggataac gcctccctgc tgcgcttta tcaaaactgg      1200 cagccgcagt ggaagcctgg cacaacgcgt ctttacgcca acgccagcat cggtctttt      1260 ggtgcgctgg cggtcaaacc ttctggcatg ccctatgagc aggccatgac gacgcgggtc     1320
cttaagccgc tcaagctgga ccatacctgg attaacgtgc gaaagcgga agaggcgcat       1380 tacgcctggg gctatcgtga cggtaaagcg gtgcgcgttt cgccgggtat gctggatgca     1440
caagcctatg gcgtgaaaac caacgtgcag gatatggcga ctgggtcat ggcaaacatg      1500 gcgccggaga acgttgctga tgcctcactt aagcagggca tcgcgctggc gcagtcgcgc     1560
tactggcgta tcgggtcaat gtatcagggt ctgggctggg agatgctcaa ctggcccgtg     1620
gaggccaaca cggtggtcga gacgagtttt ggtaatgtag cactggcgcc gttgcccgtg      1680
gcagaagtga atccaccggc tccccgtc aaagcgtcct gggtccataa aacgggctct        1740
actggcgggt ttggcagcta cgtggccttt attcctgaaa agcagatcgg tattgtgatg      1800
ctcgcgaata caagctatcc gaacccggca cgcgttgagg cggcatacca tatcctcgag     1860
gcgctacag                                                             1869

<210> SEQ ID NO 5
```

<211> LENGTH: 262
<212> TYPE: PRT
<213> ORGANISM: Artificial Sequence
<220> FEATURE:
<223> OTHER INFORMATION: CAB 1.11 construct

<400> SEQUENCE: 5

```
Asp Ile Val Leu Thr Gln Ser Pro Ala Ser Leu Ser Val Ser Leu Gly
1               5                   10                  15
Gln Arg Ala Thr Met Ser Cys Arg Ala Gly Glu Ser Val Asp Ile Phe
            20                  25                  30
Gly Val Gly Phe Leu His Trp Tyr Gln Gln Lys Pro Gly Gln Pro Pro
        35                  40                  45
Lys Leu Leu Ile Tyr Arg Ala Ser Asn Leu Glu Ser Gly Ile Pro Val
    50                  55                  60
Arg Phe Ser Gly Thr Gly Ser Gly Thr Asp Phe Thr Leu Ile Ile Asp
65                  70                  75                  80
Pro Val Glu Ala Asp Asp Val Ala Thr Tyr Tyr Cys Gln Gln Thr Asn
                85                  90                  95
Glu Asp Pro Tyr Thr Phe Gly Gly Gly Thr Lys Leu Glu Ile Lys Gly
            100                 105                 110
Gly Gly Gly Ser Gly Gly Gly Gly Ser Gly Gly Gly Ser Gly Gly
        115                 120                 125
Gly Gly Ser Gly Gly Gly Gly Ser Gly Gly Gly Gly Ser Glu Val Gln
    130                 135                 140
Leu Gln Gln Ser Gly Ala Glu Leu Val Glu Pro Gly Ala Ser Val Lys
145                 150                 155                 160
Leu Ser Cys Thr Ala Ser Gly Phe Asn Ile Lys Asp Thr Tyr Met His
                165                 170                 175
Trp Val Lys Gln Arg Pro Glu Gln Gly Leu Glu Trp Ile Gly Arg Ile
            180                 185                 190
Asp Pro Ala Asn Gly Asn Ser Lys Tyr Val Pro Lys Phe Gln Gly Lys
        195                 200                 205
Ala Thr Ile Thr Ala Asp Thr Ser Ser Asn Thr Ala Tyr Leu Gln Leu
    210                 215                 220
Thr Ser Leu Thr Ser Glu Asp Thr Ala Val Tyr Tyr Cys Ala Pro Phe
225                 230                 235                 240
Gly Tyr Tyr Val Ser Asp Tyr Ala Met Ala Tyr Trp Gly Gln Gly Thr
                245                 250                 255
Ser Val Thr Val Ser Ser
            260
```

<210> SEQ ID NO 6
<211> LENGTH: 786
<212> TYPE: DNA
<213> ORGANISM: Artificial Sequence
<220> FEATURE:
<223> OTHER INFORMATION: CAB 1.11 construct

<400> SEQUENCE: 6

```
gacatcgtcc tgacccagag cccggcaagc ctgtctgttt ccctgggcca gcgtgccact   60
atgtcctgca gagcgggtga gtctgttgac attttcggtg tcggttttct gcactggtac  120
caacagaaac cgggtcagcc gccaaaactg ctgatctatc gtgcttctaa cctggagtcc  180
ggcatcccgg tacgtttctc cggtactggc tctggtactg attttaccct gattatcgac  240
ccggtggaag cagacgatgt tgccacctac tattgccagc agaccaacga ggatccgtac  300
accttcggtg gcggtactaa actggagatc aaaggcggtg gtggttctgg tggtggtggt  360
```

```
agcggtggcg gtggtagcgg tggcggtggc agcggtggtg gtggctctgg tggcggtggc      420
tctgaagtgc agctgcagca gtccggtgcg gagctcgttg aaccgggcgc ttctgtgaaa      480
ctgtcttgca ctgcatctgg tttcaacatt aaggacacct acatgcactg ggtgaaacaa      540
cgcccggaac agggtctgga gtggatcggt cgcatcgatc cggctaacgg taacagcaaa      600
tacgtgccaa aattccaggg taaagcaacc atcactgctg ataccctcct taacactgct      660
tacctgcagc tgacttccct gactagcgaa gacaccgcgg tttattactg cgctccgttc      720
ggctactatg tcagcgatta cgcaatggcc tactggggtc agggcacctc tgttaccgtt      780
tctagc                                                                786
```

<210> SEQ ID NO 7
<211> LENGTH: 623
<212> TYPE: PRT
<213> ORGANISM: Artificial Sequence
<220> FEATURE:
<223> OTHER INFORMATION: CAB 1.11 construct

<400> SEQUENCE: 7

```
Asp Ile Val Leu Thr Gln Ser Pro Ala Ser Leu Ser Val Ser Leu Gly
1               5                   10                  15

Gln Arg Ala Thr Met Ser Cys Arg Ala Gly Glu Ser Val Asp Ile Phe
            20                  25                  30

Gly Val Gly Phe Leu His Trp Tyr Gln Gln Lys Pro Gly Gln Pro Pro
        35                  40                  45

Lys Leu Leu Ile Tyr Arg Ala Ser Asn Leu Glu Ser Gly Ile Pro Val
    50                  55                  60

Arg Phe Ser Gly Thr Gly Ser Gly Thr Asp Phe Thr Leu Ile Ile Asp
65                  70                  75                  80

Pro Val Glu Ala Asp Asp Val Ala Thr Tyr Tyr Cys Gln Gln Thr Asn
                85                  90                  95

Glu Asp Pro Tyr Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gly Gly
        115                 120                 125

Gly Gly Ser Gly Gly Gly Gly Ser Gly Gly Gly Gly Ser Glu Val Gln
    130                 135                 140

Leu Gln Gln Ser Gly Ala Glu Leu Val Glu Pro Gly Ala Ser Val Lys
145                 150                 155                 160

Leu Ser Cys Thr Ala Ser Gly Phe Asn Ile Lys Asp Thr Tyr Met His
                165                 170                 175

Trp Val Lys Gln Arg Pro Glu Gln Gly Leu Glu Trp Ile Gly Arg Ile
            180                 185                 190

Asp Pro Ala Asn Gly Asn Ser Lys Tyr Val Pro Lys Phe Gln Gly Lys
        195                 200                 205

Ala Thr Ile Thr Ala Asp Thr Ser Ser Asn Thr Ala Tyr Leu Gln Leu
    210                 215                 220

Thr Ser Leu Thr Ser Glu Asp Thr Ala Val Tyr Tyr Cys Ala Pro Phe
225                 230                 235                 240

Gly Tyr Tyr Val Ser Asp Tyr Ala Met Ala Tyr Trp Gly Gln Gly Thr
                245                 250                 255

Ser Val Thr Val Ser Ser Thr Pro Val Ser Glu Lys Gln Leu Ala Glu
            260                 265                 270

Val Val Ala Asn Thr Ile Thr Pro Leu Met Lys Ala Gln Ser Val Pro
        275                 280                 285
```

Gly Met Ala Val Ala Val Ile Tyr Gln Gly Lys Pro His Tyr Tyr Thr
            290                 295                 300

Phe Gly Lys Ala Asp Ile Ala Ala Asn Lys Pro Val Thr Pro Gln Thr
305                 310                 315                 320

Leu Phe Glu Leu Gly Ser Ile Ser Lys Thr Phe Thr Gly Val Leu Gly
                325                 330                 335

Gly Asp Ala Ile Ala Arg Gly Glu Ile Ser Leu Asp Asp Ala Val Thr
            340                 345                 350

Arg Tyr Trp Pro Gln Leu Thr Gly Lys Gln Trp Gln Gly Ile Arg Met
            355                 360                 365

Leu Asp Leu Ala Thr Tyr Thr Ala Gly Gly Leu Pro Leu Gln Val Pro
370                 375                 380

Asp Glu Val Thr Asp Asn Ala Ser Leu Leu Arg Phe Tyr Gln Asn Trp
385                 390                 395                 400

Gln Pro Gln Trp Lys Pro Gly Thr Thr Arg Leu Tyr Ala Asn Ala Ser
                405                 410                 415

Ile Gly Leu Phe Gly Ala Leu Ala Val Lys Pro Ser Gly Met Pro Tyr
            420                 425                 430

Glu Gln Ala Met Thr Thr Arg Val Leu Lys Pro Leu Lys Leu Asp His
            435                 440                 445

Thr Trp Ile Asn Val Pro Lys Ala Glu Glu Ala His Tyr Ala Trp Gly
450                 455                 460

Tyr Arg Asp Gly Lys Ala Val Arg Val Ser Pro Gly Met Leu Asp Ala
465                 470                 475                 480

Gln Ala Tyr Gly Val Lys Thr Asn Val Gln Asp Met Ala Asn Trp Val
                485                 490                 495

Met Ala Asn Met Ala Pro Glu Asn Val Ala Asp Ala Ser Leu Lys Gln
            500                 505                 510

Gly Ile Ala Leu Ala Gln Ser Arg Tyr Trp Arg Ile Gly Ser Met Tyr
            515                 520                 525

Gln Gly Leu Gly Trp Glu Met Leu Asn Trp Pro Val Glu Ala Asn Thr
530                 535                 540

Val Val Glu Thr Ser Phe Gly Asn Val Ala Leu Ala Pro Leu Pro Val
545                 550                 555                 560

Ala Glu Val Asn Pro Pro Ala Pro Pro Val Lys Ala Ser Trp Val His
                565                 570                 575

Lys Thr Gly Ser Thr Gly Gly Phe Gly Ser Tyr Val Ala Phe Ile Pro
            580                 585                 590

Glu Lys Gln Ile Gly Ile Val Met Leu Ala Asn Thr Ser Tyr Pro Asn
            595                 600                 605

Pro Ala Arg Val Glu Ala Ala Tyr His Ile Leu Glu Ala Leu Gln
610                 615                 620

<210> SEQ ID NO 8
<211> LENGTH: 623
<212> TYPE: PRT
<213> ORGANISM: Artificial Sequence
<220> FEATURE:
<223> OTHER INFORMATION: CAB 1.11i construct

<400> SEQUENCE: 8

Asp Ile Val Leu Thr Gln Ser Pro Ala Ser Leu Ser Val Ser Leu Gly
1               5                   10                  15

Gln Arg Ala Thr Met Ser Cys Arg Ala Gly Glu Ser Val Asp Ile Phe
            20                  25                  30

```
Gly Val Gly Phe Leu His Trp Tyr Gln Gln Lys Pro Gly Gln Pro
         35                  40                  45

Lys Leu Leu Ile Tyr Arg Ala Ser Asn Leu Glu Ser Gly Ile Pro Val
 50                  55                  60

Arg Phe Ser Gly Thr Gly Ser Gly Thr Asp Phe Thr Leu Ile Ile Asp
 65                  70                  75                  80

Pro Val Glu Ala Asp Asp Val Ala Thr Tyr Tyr Cys Gln Gln Thr Asn
                 85                  90                  95

Glu Asp Pro Tyr Thr Phe Gly Gly Thr Lys Leu Glu Ile Lys Gly
                100                 105                 110

Gly Gly Gly Ser Gly Gly Gly Ser Gly Gly Gly Ser Gly Gly
         115                 120                 125

Gly Gly Ser Gly Gly Gly Ser Gly Gly Gly Ser Glu Val Gln
         130                 135                 140

Leu Gln Gln Ser Gly Ala Glu Leu Val Glu Pro Gly Ala Ser Val Lys
145                 150                 155                 160

Leu Ser Cys Thr Ala Ser Gly Phe Asn Ile Lys Asp Thr Tyr Met His
                165                 170                 175

Trp Val Lys Gln Arg Pro Glu Gln Gly Leu Glu Trp Ile Gly Arg Ile
                180                 185                 190

Asp Pro Ala Asn Gly Asn Ser Lys Tyr Val Pro Lys Phe Gln Gly Lys
                195                 200                 205

Ala Thr Ile Thr Ala Asp Thr Ser Ser Asn Thr Ala Tyr Leu Gln Leu
                210                 215                 220

Thr Ser Leu Thr Ser Glu Asp Thr Ala Val Tyr Tyr Cys Ala Pro Phe
225                 230                 235                 240

Gly Tyr Tyr Val Ser Asp Tyr Ala Met Ala Tyr Trp Gly Gln Gly Thr
                245                 250                 255

Ser Val Thr Val Ser Ser Thr Pro Val Ser Glu Lys Gln Leu Ala Glu
                260                 265                 270

Val Val Ala Asn Thr Ile Thr Pro Leu Met Ala Ala Gln Ser Val Pro
                275                 280                 285

Gly Met Ala Val Ala Val Ile Tyr Gln Gly Lys Pro His Tyr Tyr Thr
                290                 295                 300

Phe Gly Lys Ala Asp Ile Ala Ala Asn Lys Pro Val Thr Pro Gln Thr
305                 310                 315                 320

Leu Phe Glu Leu Gly Ser Ile Ser Lys Thr Phe Thr Gly Val Leu Gly
                325                 330                 335

Gly Asp Ala Ile Ala Arg Gly Glu Ile Ser Leu Asp Asp Ala Val Thr
                340                 345                 350

Arg Tyr Trp Pro Gln Leu Thr Gly Lys Gln Trp Gln Gly Ile Arg Met
                355                 360                 365

Leu Asp Leu Ala Thr Tyr Thr Ala Gly Gly Leu Pro Leu Gln Val Pro
                370                 375                 380

Asp Glu Val Thr Asp Asn Ala Ser Leu Leu Arg Phe Tyr Gln Asn Trp
385                 390                 395                 400

Gln Pro Gln Trp Lys Pro Gly Thr Thr Arg Leu Tyr Ala Asn Ala Ser
                405                 410                 415

Ile Gly Leu Phe Gly Ala Leu Ala Val Lys Pro Ser Gly Met Pro Tyr
                420                 425                 430

Glu Gln Ala Met Thr Thr Arg Val Leu Lys Pro Leu Lys Leu Asp His
                435                 440                 445

Thr Trp Ile Asn Val Pro Lys Ala Glu Glu Ala His Tyr Ala Trp Gly
                450                 455                 460
```

```
Tyr Arg Asp Gly Lys Ala Val Arg Val Ser Pro Gly Met Leu Asp Ala
465                 470                 475                 480

Gln Ala Tyr Gly Val Lys Thr Asn Val Gln Asp Met Ala Asn Trp Val
            485                 490                 495

Met Ala Asn Met Ala Pro Glu Asn Val Ala Asp Ala Ser Leu Lys Gln
            500                 505                 510

Gly Ile Ala Leu Ala Gln Ser Arg Tyr Trp Arg Ile Gly Ser Met Tyr
        515                 520                 525

Gln Gly Leu Gly Trp Glu Met Leu Asn Trp Pro Val Glu Ala Asn Thr
    530                 535                 540

Val Val Glu Thr Ser Phe Gly Asn Val Ala Leu Ala Pro Leu Pro Val
545                 550                 555                 560

Ala Glu Val Asn Pro Pro Ala Pro Pro Val Lys Ala Ser Trp Val His
            565                 570                 575

Lys Thr Gly Ser Thr Gly Gly Phe Gly Ala Tyr Val Ala Phe Ile Pro
            580                 585                 590

Glu Lys Gln Ile Gly Ile Val Met Leu Ala Asn Thr Ser Tyr Pro Asn
        595                 600                 605

Pro Ala Arg Val Glu Ala Ala Tyr His Ile Leu Glu Ala Leu Gln
    610                 615                 620

<210> SEQ ID NO 9
<211> LENGTH: 1869
<212> TYPE: DNA
<213> ORGANISM: Artificial Sequence
<220> FEATURE:
<223> OTHER INFORMATION: CAB 1.11 construct

<400> SEQUENCE: 9
gacatcgtcc tgacccagag cccggcaagc ctgtctgttt ccctgggcca gcgtgccact     60
atgtcctgca gagcgggtga gtctgttgac attttcggtg tcggttttct gcactggtac    120
caacagaaac cgggtcagcc gccaaaactg ctgatctatc gtgcttctaa cctggagtcc    180
ggcatcccgg tacgtttctc cggtactggc tctggtactg attttaccct gattatcgac    240
ccggtggaag cagacgatgt tgccacctac tattgccagc agaccaacga ggatccgtac    300
accttcggtg cggtactaa actggagatc aaaggcggtg gtggttctgg tggtggtggt    360
agcggtggcg gtggtagcgg tggcggtggc agcggtggtg gtggctctgg tggcggtggc    420
tctgaagtgc agctgcagca gtccggtgcg gagctcgttg aaccgggcgc ttctgtgaaa    480
ctgtcttgca ctgcatctgg tttcaacatt aaggacacct acatgcactg ggtgaaacaa    540
cgcccggaac agggtctgga gtggatcggt cgcatcgatc cggctaacgg taacagcaaa    600
tacgtgccaa aattccaggg taaagcaacc atcactgctg atacctcctc taacactgct    660
tacctgcagc tgacttccct gactagcgaa gacaccgcgg tttattactg cgctccgttc    720
ggctactatg tcagcgatta cgcaatggcc tactgggtc agggcacctc tgttaccgtt    780
tctagcacac cggtgtcaga aaaacagctg cggaggtgg tcgcgaatac gattaccccg    840
ctgatgaaag cccagtctgt tccaggcatg gcggtgccg ttatttatca gggaaaaccg    900
cactattaca catttggcaa ggccgatatc gcggcgaata acccgttac gcctcagacc    960 ctgttcgagc tgggttctat aagtaaaacc ttcaccggcg ttttaggtgg ggatgccatt   1020
gctcgcggtg aaatttcgct ggacgatgcg gtgaccagat actggccaca gctgacgggc   1080
aagcagtggc agggtattcg tatgctggat ctcgccacct acaccgctgg cggcctgccg   1140
ctacaggtac cggatgaggt cacgcgataac gcctccctgc tgcgctttta tcaaaactgg   1200
```

```
cagccgcagt ggaagcctgg cacaacgcgt ctttacgcca acgccagcat cggtcttttt    1260
ggtgcgctgg cggtcaaacc ttctggcatg ccctatgagc aggccatgac gacgcgggtc    1320
cttaagccgc tcaagctgga ccatacctgg attaacgtgc cgaaagcgga agaggcgcat    1380
tacgcctggg gctatcgtga cggtaaagcg gtgcgcgttt cgccgggtat gctggatgca    1440
caagcctatg gcgtgaaaac caacgtgcag gatatggcga actgggtcat ggcaaacatg    1500
gcgccggaga acgttgctga tgcctcactt aagcagggca tcgcgctggc gcagtcgcgc    1560
tactggcgta tcgggtcaat gtatcagggt ctgggctggg agatgctcaa ctggcccgtg    1620
gaggccaaca cggtggtcga gacgagtttt ggtaatgtag cactggcgcc gttgcccgtg    1680
gcagaagtga atccaccggc tcccccggtc aaagcgtcct gggtccataa aacgggctct    1740
actggcgggt ttggcagcta cgtggccttt attcctgaaa agcagatcgg tattgtgatg    1800
ctcgcgaata caagctatcc gaacccggca cgcgttgagg cggcatacca tatcctcgag    1860
gcgctacag                                                              1869

<210> SEQ ID NO 10
<211> LENGTH: 1869
<212> TYPE: DNA
<213> ORGANISM: Artificial Sequence
<220> FEATURE:
<223> OTHER INFORMATION: CAB 1.11i construct

<400> SEQUENCE: 10
gacatcgtcc tgacccagag cccggcaagc ctgtctgttt ccctgggcca gcgtgccact     60
atgtcctgca gagcgggtga gtctgttgac attttcggtg tcggttttct gcactggtac    120
caacagaaac cggtcagcc gccaaaactg ctgatctatc gtgcttctaa cctggagtcc     180
ggcatcccgg tacgtttctc cggtactggc tctggtactg attttaccct gattatcgac    240
ccggtggaag cagacgatgt tgccacctac tattgccagc agaccaacga ggatccgtac    300
accttcggtg gcggtactaa actggagatc aaaggcggtg gtggttctgg tggtggtggt    360
agcggtggcg gtggtagcgg tggcggtggc agcggtggtg gtggctctgg tggcggtggc    420
tctgaagtgc agctgcagca gtccggtgcg gagctcgttg aaccgggcgc ttctgtgaaa    480
ctgtcttgca ctgcatctgg tttcaacatt aaggacacct acatgcactg ggtgaaacaa    540
cgcccggaac agggtctgga gtggatcggt cgcatcgatc cggctaacgg taacagcaaa    600
tacgtgccaa aattccaggg taagcaacc atcactgctg ataccctcc taacactgct    660 tacctgcagc tgacttccct gactagcgaa gacaccgcgg tttattactg cgctccgttc    720
ggctactatg tcagcgatta cgcaatggcc tactggggtc agggcacctc tgttaccgtt    780
tctagcacac cggtgtcaga aaaacagctg gcggaggtgg tcgcgaatac gattacccc    840 ctgatggcgg cccagtctgt tccaggcatg gcggtggccg ttatttatca gggaaaaccg    900
cactattaca catttggcaa ggccgatatc gcggcgaata acccgttac gcctcagacc    960 ctgttcgagc tgggttctat aagtaaaacc ttcaccggcg ttttaggtgg ggatgccatt    1020
gctcgcggtg aaatttcgct ggacgatgcg gtgaccagat actggccaca gctgacgggc    1080
aagcagtggc agggtattcg tatgctggat ctcgccacct acaccgctgg cggcctgccg    1140
ctacaggtac cggatgaggt cacggataac gcctccctgc tgcgctttta tcaaaactgg    1200
cagccgcagt ggaagcctgg cacaacgcgt ctttacgcca acgccagcat cggtcttttt    1260
ggtgcgctgg cggtcaaacc ttctggcatg ccctatgagc aggccatgac gacgcgggtc    1320
cttaagccgc tcaagctgga ccatacctgg attaacgtgc cgaaagcgga agaggcgcat    1380
```

```
tacgcctggg gctatcgtga cggtaaagcg gtgcgcgttt cgccgggtat gctggatgca    1440
caagcctatg gcgtgaaaac caacgtgcag gatatggcga actgggtcat ggcaaacatg    1500
gcgccggaga acgttgctga tgcctcactt aagcagggca tcgcgctggc gcagtcgcgc    1560
tactggcgta tcgggtcaat gtatcagggt ctgggctggg agatgctcaa ctggcccgtg    1620
gaggccaaca cggtggtcga gacgagtttt ggtaatgtag cactggcgcc gttgcccgtg    1680
gcagaagtga atccaccggc tcccccggtc aaagcgtcct gggtccataa aacgggctct    1740
actggcgggt ttggcgcgta cgtggccttt attcctgaaa agcagatcgg tattgtgatg    1800
ctcgcgaata caagctatcc gaacccggca cgcgttgagg cggcatacca tatcctcgag    1860
gcgctacag                                                             1869
```

<210> SEQ ID NO 11
<211> LENGTH: 361
<212> TYPE: PRT
<213> ORGANISM: Unknown
<220> FEATURE:
<223> OTHER INFORMATION: beta-lactamase protein

<400> SEQUENCE: 11

```
Thr Pro Val Ser Glu Lys Gln Leu Ala Glu Val Val Ala Asn Thr Ile
1               5                   10                  15

Thr Pro Leu Met Lys Ala Gln Ser Val Pro Gly Met Ala Val Ala Val
                20                  25                  30

Ile Tyr Gln Gly Lys Pro His Tyr Tyr Thr Phe Gly Lys Ala Asp Ile
            35                  40                  45

Ala Ala Asn Lys Pro Val Thr Pro Gln Thr Leu Phe Glu Leu Gly Ser
        50                  55                  60

Ile Ser Lys Thr Phe Thr Gly Val Leu Gly Gly Asp Ala Ile Ala Arg
65                  70                  75                  80

Gly Glu Ile Ser Leu Asp Asp Ala Val Thr Arg Tyr Trp Pro Gln Leu
                85                  90                  95

Thr Gly Lys Gln Trp Gln Gly Ile Arg Met Leu Asp Leu Ala Thr Tyr
            100                 105                 110

Thr Ala Gly Gly Leu Pro Leu Gln Val Pro Asp Glu Val Thr Asp Asn
        115                 120                 125

Ala Ser Leu Leu Arg Phe Tyr Gln Asn Trp Gln Pro Gln Trp Lys Pro
    130                 135                 140

Gly Thr Thr Arg Leu Tyr Ala Asn Ala Ser Ile Gly Leu Phe Gly Ala
145                 150                 155                 160

Leu Ala Val Lys Pro Ser Gly Met Pro Tyr Glu Gln Ala Met Thr Thr
                165                 170                 175

Arg Val Leu Lys Pro Leu Lys Leu Asp His Thr Trp Ile Asn Val Pro
            180                 185                 190

Lys Ala Glu Glu Ala His Tyr Ala Trp Gly Tyr Arg Asp Gly Lys Ala
        195                 200                 205

Val Arg Val Ser Pro Gly Met Leu Asp Ala Gln Ala Tyr Gly Val Lys
    210                 215                 220

Thr Asn Val Gln Asp Met Ala Asn Trp Val Met Ala Asn Met Ala Pro
225                 230                 235                 240

Glu Asn Val Ala Asp Ala Ser Leu Lys Gln Gly Ile Ala Leu Ala Gln
                245                 250                 255

Ser Arg Tyr Trp Arg Ile Gly Ser Met Tyr Gln Gly Leu Gly Trp Glu
            260                 265                 270
```

```
Met Leu Asn Trp Pro Val Glu Ala Asn Thr Val Val Glu Thr Ser Phe
    275                 280                 285

Gly Asn Val Ala Leu Ala Pro Leu Pro Val Ala Glu Val Asn Pro Pro
    290                 295                 300

Ala Pro Pro Val Lys Ala Ser Trp Val His Lys Thr Gly Ser Thr Gly
305                 310                 315                 320

Gly Phe Gly Ser Tyr Val Ala Phe Ile Pro Glu Lys Gln Ile Gly Ile
                325                 330                 335

Val Met Leu Ala Asn Thr Ser Tyr Pro Asn Pro Ala Arg Val Glu Ala
                340                 345                 350

Ala Tyr His Ile Leu Glu Ala Leu Gln
                355                 360

<210> SEQ ID NO 12
<211> LENGTH: 1083
<212> TYPE: DNA
<213> ORGANISM: Unknown
<220> FEATURE:
<223> OTHER INFORMATION: beta-lactamase encoding sequence

<400> SEQUENCE: 12
acaccggtgt cagaaaaaca gctggcggag gtggtcgcga atacgattac cccgctgatg      60
aaagcccagt ctgttccagg catggcggtg gccgttattt atcagggaaa accgcactat     120
tacacatttg gcaaggccga tatcgcggcg aataaacccg ttacgcctca gaccctgttc     180
gagctgggtt ctataagtaa aaccttcacc ggcgttttag gtggggatgc cattgctcgc     240
ggtgaaattt cgctggacga tgcggtgacc agatactggc cacagctgac gggcaagcag     300
tggcagggta ttcgtatgct ggatctcgcc acctacaccg ctggcggcct gccgctacag     360
gtaccggatg aggtcacgga taacgcctcc ctgctgcgct ttatcaaaaa ctggcagccg     420
cagtggaagc ctggcacaac gcgtctttac gccaacgcca gcatcggtct ttttggtgcg     480
ctggcggtca aaccttctgg catgcccttat gagcaggcca tgacgacgcg ggtccttaag     540
ccgctcaagc tggaccatac ctggattaac gtgccgaaag cggaagaggc gcattacgcc     600
tggggctatc gtgacggtaa agcggtgcgc gtttcgccgg gtatgctgga tgcacaagcc     660
tatggcgtga aaccaacgt gcaggatatg gcgaactggg tcatggcaaa catggcgccg     720
gagaacgttg ctgatgcctc acttaagcag ggcatcgcgc tggcgcagtc gcgctactgg     780
cgtatcgggt caatgtatca gggtctgggc tgggagatgc tcaactggcc cgtggaggcc     840
aacacggtgg tcgagacgag ttttggtaat gtagcactgg cgccgttgcc cgtggcagaa     900
gtgaatccac cggctccccc ggtcaaagcg tcctgggtcc ataaaacggg ctctactggc     960
gggtttggca gctacgtggc ctttattcct gaaaagcaga tcggtattgt gatgctcgcg    1020
aatacaagct atccgaaccc ggcacgcgtt gaggcggcat accatatcct cgaggcgcta    1080
cag                                                                  1083

<210> SEQ ID NO 13
<211> LENGTH: 361
<212> TYPE: PRT
<213> ORGANISM: Artificial Sequence
<220> FEATURE:
<223> OTHER INFORMATION: synthetic de-immunized beta-lactamase protein

<400> SEQUENCE: 13

Thr Pro Val Ser Glu Lys Gln Leu Ala Glu Val Val Ala Asn Thr Ile
1               5                   10                  15

Thr Pro Leu Met Ala Ala Gln Ser Val Pro Gly Met Ala Val Ala Val
```

|  |  |  |  | 20 |  |  |  | 25 |  |  |  | 30 |  |  |
|--|--|--|--|--|--|--|--|--|--|--|--|--|--|--|

Ile Tyr Gln Gly Lys Pro His Tyr Tyr Thr Phe Gly Lys Ala Asp Ile
        35                40                45

Ala Ala Asn Lys Pro Val Thr Pro Gln Thr Leu Phe Glu Leu Gly Ser
  50                  55                60

Ile Ser Lys Thr Phe Thr Gly Val Leu Gly Gly Asp Ala Ile Ala Arg
65                  70                75              80

Gly Glu Ile Ser Leu Asp Asp Ala Val Thr Arg Tyr Trp Pro Gln Leu
                85                90              95

Thr Gly Lys Gln Trp Gln Gly Ile Arg Met Leu Asp Leu Ala Thr Tyr
        100               105              110

Thr Ala Gly Gly Leu Pro Leu Gln Val Pro Asp Glu Val Thr Asp Asn
      115               120              125

Ala Ser Leu Leu Arg Phe Tyr Gln Asn Trp Gln Pro Gln Trp Lys Pro
    130               135              140

Gly Thr Thr Arg Leu Tyr Ala Asn Ala Ser Ile Gly Leu Phe Gly Ala
145                  150                155              160

Leu Ala Val Lys Pro Ser Gly Met Pro Tyr Glu Gln Ala Met Thr Thr
        165               170              175

Arg Val Leu Lys Pro Leu Lys Leu Asp His Thr Trp Ile Asn Val Pro
      180               185              190

Lys Ala Glu Glu Ala His Tyr Ala Trp Gly Tyr Arg Asp Gly Lys Ala
    195               200              205

Val Arg Val Ser Pro Gly Met Leu Asp Ala Gln Ala Tyr Gly Val Lys
  210                215              220

Thr Asn Val Gln Asp Met Ala Asn Trp Val Met Ala Asn Met Ala Pro
225                  230                235              240

Glu Asn Val Ala Asp Ala Ser Leu Lys Gln Gly Ile Ala Leu Ala Gln
                245              250              255

Ser Arg Tyr Trp Arg Ile Gly Ser Met Tyr Gln Gly Leu Gly Trp Glu
        260               265              270

Met Leu Asn Trp Pro Val Glu Ala Asn Thr Val Val Glu Thr Ser Phe
      275               280              285

Gly Asn Val Ala Leu Ala Pro Leu Pro Val Ala Glu Val Asn Pro Pro
    290               295              300

Ala Pro Pro Val Lys Ala Ser Trp Val His Lys Thr Gly Ser Thr Gly
305                  310                315              320

Gly Phe Gly Ala Tyr Val Ala Phe Ile Pro Glu Lys Gln Ile Gly Ile
        325               330              335

Val Met Leu Ala Asn Thr Ser Tyr Pro Asn Pro Ala Arg Val Glu Ala
      340               345              350

Ala Tyr His Ile Leu Glu Ala Leu Gln
    355               360

<210> SEQ ID NO 14
<211> LENGTH: 5232
<212> TYPE: DNA
<213> ORGANISM: Artificial Sequence
<220> FEATURE:
<223> OTHER INFORMATION: synthetic pHR19.2 plasmid nucleotide sequence

<400> SEQUENCE: 14
aggaattatc atatgaaata cctgctgccg accgctgctg ctggtctgct gctcctcgct      60
gcccagccgg ccatggccga catcgtcctg acccagagcc cggcaagcct gtctgtttcc     120
ctgggccagc gtgccactat gtcctgcaga gcgggtgagt ctgttgacat tttcggtgtc     180

```
ggttttctgc actggtacca acagaaaccg ggtcagccgc caaaactgct gatctatcgt      240
gcttctaacc tggagtccgg catcccggta cgtttctccg gtactggctc tggtactgat      300
tttaccctga ttatcgaccc ggtggaagca gacgatgttg ccacctacta ttgccagcag      360
accaacgagg atccgtacac cttcggtggc ggtactaaac tggagatcaa aggcggtggt      420
ggttctggtg gtggtggtag cggtggcggt ggtagcggtg gcggtggcag cggtggtggt      480
ggctctggtg gcggtggctc tgaagtgcag ctgcagcagt ccggtgcgga gctcgttgaa      540
ccgggcgctt ctgtgaaact gtcttgcact gcatctggtt tcaacattaa ggacacctac      600
atgcactggg tgaaacaacg cccggaacag ggtctggagt ggatcggtcg catcgatccg      660
gctaacggta acagcaaata cgtgccaaaa ttccagggta aagcaaccat cactgctgat      720
acctcctcta acactgctta cctgcagctg acttccctga ctagcgaaga caccgcggtt      780
tattactgcg ctccgttcgg ctactatgtc agcgattacg caatggccta ctggggtcag      840
ggcacctctg ttaccgtttc tagcacaccg gtgtcagaaa acagctggc ggaggtggtc      900 gcgaatacga ttaccccgct gatggcggcc cagtctgttc caggcatggc ggtggccgtt      960
atttatcagg gaaaaccgca ctattacaca tttggcaagg ccgatatcgc ggcgaataaa     1020
cccgttacgc ctcagaccct gttcgagctg ggttctataa gtaaaacctt caccggcgtt     1080
ttaggtgggg atgccattgc tcgcggtgaa atttcgctgg acgatgcggt gaccagatac     1140
tggccacagc tgacgggcaa gcagtggcag ggtattcgta tgctggatct cgccacctac     1200
accgctggcg gcctgccgct acaggtaccg gatgaggtca cggataacgc ctccctgctg     1260
cgcttttatc aaaactggca gccgcagtgg aagcctggca caacgcgtct ttacgccaac     1320
gccagcatcg gtcttttttgg tgcgctggcg gtcaaacctt ctggcatgcc ctatgagcag     1380
gccatgacga cgcgggtcct taagccgctc aagctggacc ataccgtggat taacgtgccg     1440 aaagcggaag aggcgcatta cgcctgggc tatcgtgacg gtaaagcggt gcgcgtttcg     1500
ccgggtatgc tggatgcaca agcctatggc gtgaaaacca acgtgcagga tatggcgaac     1560
tgggtcatgc caaacatggc gccggagaac gttgctgatg cctcacttaa gcagggcatc     1620
gcgctggcgc agtcgcgcta ctggcgtatc gggtcaatgt atcagggtct gggctgggag     1680
atgctcaact ggcccgtgga ggccaacacg gtgtcgaga cgagttttgg taatgtagca     1740
ctggcgccgt tgcccgtggc agaagtgaat ccaccggctc ccccggtcaa agcgtcctgg     1800
gtccataaaa cgggctctac tggcggtttt ggcgcgtacg tggcctttat tcctgaaaag     1860
cagatcggta ttgtgatgct cgcgaataca agctatccga acccggcacg cgttgaggcg     1920
gcataccata tcctcgaggc gctacagtag gaattcgagc tccgtcgaca agcttgcggc     1980
cgcactcgag atcaaacggg ctagccagcc agaactcgcc ccggaagacc ccgaggatgt     2040
cgagcaccac caccaccacc actgagatcc ggctgctaac aaagcccgaa aggaagctga     2100
gttggctgct gccaccgctg agcaataact agcataaccc cttggggcct ctaaacgggt     2160
cttgaggggt ttttgctga aaggaggaac tatatccgga ttggcgaatg ggacgcgccc     2220
tgtagcggcg cattaagcgc ggcgggtgtg gtggttacgc gcagcgtgac cgctacactt     2280
gccagcgccc tagcgcccgc tcctttcgct ttcttccctt cctttctcgc cacgttcgcc     2340
ggctttcccc gtcaagctct aaatcggggg ctccctttag ggttccgatt tagtgcttta     2400
cggcacctcg accccaaaaa acttgattag ggtgatggtt cacgtagtgg gccatcgccc     2460
tgatagacgt ttttcgccc tttgacgttg gagtccacgt tctttaatag tggactcttg     2520
ttccaaactg gaacaacact caaccctatc tcggtctatt cttttgattt ataagggatt     2580
```

```
ttgccgattt cggcctattg gttaaaaaat gagctgattt aacaaaaatt taacgcgaat    2640
tttaacaaaa tattaacgct tacaatttcc tgatgcggta ttttctcctt acgcatctgt    2700
gcggtatttc acaccgcata tggtgcactc tcagtacaat ctgctctgat gccgcatagt    2760
taagccagcc ccgacacccg ccaacacccg ctgacgcgcc ctgacgggct tgtctgctcc    2820
cggcatccgc ttacagacaa gctgtgaccg tctccgggag ctgcatgtgt cagaggtttt    2880
caccgtcatc accgaaacgc gcgagacgaa agggcctcgt gatacgccta tttttatagg    2940
ttaatgtcat gataataatg gtttcttaga cgtcaggtgg cacttttcgg ggaaatgtgc    3000
gcggaacccc tatttgttta ttttttctaaa tacattcaaa tatgtatccg ctcatgagac    3060 ataaccctg tggcagcatc acccgacgca ctttgcgccg aataaatacc tgtgacggaa    3120
gatcacttcg cagaataaat aaatcctggt gtccctgttg ataccgggaa gccctgggcc    3180
aacttttggc gaaaatgaga cgttgatcgg cacgtaagag gttccaactt tcaccataat    3240
gaaataagat cactaccggg cgtattttt gagttatcga gattttcagg agctaaggaa    3300
gctaaaatgg agaaaaaaat cactggatat accaccgttg atatatccca atggcatcgt    3360
aaagaacatt ttgaggcatt tcagtcagtt gctcaatgta cctataacca gaccgttcag    3420
ctggatatta cggccttttt aaagaccgta agaaaaata agcacaagtt tatccggcc    3480 tttattcaca ttcttgcccg cctgatgaat gctcatccgg aattccgtat ggcaatgaaa    3540
gacggtgagc tggtgatatg ggatagtgtt caccccttgtt acaccgtttt ccatgagcaa    3600
actgaaacgt tttcatcgct ctggagtgaa taccacgacg atttccggca gtttctacac    3660
atatattcgc aagatgtggc gtgttacggt gaaaacctgg cctatttccc taaagggttt    3720
attgagaata tgttttttcgt ctcagccaat ccctgggtga gtttcaccag ttttgattta    3780
aacgtggcca atatggacaa cttcttcgcc cccgttttca cgatgggcaa atattatacg    3840
caaggcgaca aggtgctgat gccgctggcg attcaggttc atcatgccgt ctgtgatggc    3900
ttccatgtcg gcagaatgct taatgaatta caacagtact gcgatgagtg gcagggcggg    3960
gcgtaaagac agatcgctga gataggtgcc tcactgatta agcattggta actgtcagac    4020
caagtttact catatatact ttagattgat ttaaaacttc atttttaatt taaaaggatc    4080
taggtgaaga tccttttttga taatctcatg accaaaatcc cttaacgtga gttttcgttc    4140
cactgagcgt cagacccccgt agaaaagatc aaaggatctt cttgagatcc ttttttttctg    4200 cgcgtaatct gctgcttgca acaaaaaaaa ccaccgctac cagcggtggt ttgtttgccg    4260
gatcaagagc taccaactct ttttccgaag gtaactggct tcagcagagc gcagatacca    4320
aatactgttc ttctagtgta gccgtagtta ggccaccact tcaagaactc tgtagcaccg    4380
cctacatacc tcgctctgct aatcctgtta ccagtggctg ctgccagtgg cgataagtcg    4440
tgtcttaccg ggttggactc aagacgatag ttaccggata aggcgcagcg gtcgggctga    4500
acggggggtt cgtgcacaca gcccagcttg gagcgaacga cctacaccga actgagatac    4560
ctacagcgtg agctatgaga aagcgccacg cttcccgaag ggagaaaggc ggacaggtat    4620
ccggtaagcg gcagggtcgg aacaggagag cgcacgaggg agcttccagg gggaaacgcc    4680
tggtatcttt atagtcctgt cgggtttcgc cacctctgac ttgagcgtcg atttttgtga    4740
tgctcgtcag ggggggggag cctatggaaa aacgccagca acgcggcctt tttacggttc    4800
ctggcctttt gctggccttt tgctcacatg ttctttcctg cgttatcccc tgattctgtg    4860
gataaccgta ttaccgcctt tgagtgagct gataccgctc gccgcagccg aacgaccgag    4920
cgcagcgagt cagtgagcga ggaagcggaa gagcgcccaa tacgcaaacc gcctctcccc    4980
```

```
gcgcgttggc cgattcatta atgcagctgg cacgacaggt ttcccgactg gaaagcgggc    5040
agtgagcgca acgcaattaa tgtgagttag ctcactcatt aggcacccca ggctttacac    5100
tttatgcttc cggctcgtat gttgtgtgga attgtgagcg gataacaatt tcacacagga    5160
aacagctatg accatgatta cgccaagcta tttaggtgac actatagaat actcaagctt    5220
tctagattaa gg                                                        5232
```

```
<210> SEQ ID NO 15
<211> LENGTH: 36
<212> TYPE: DNA
<213> ORGANISM: Artificial Sequence
<220> FEATURE:
<223> OTHER INFORMATION: synthetic primer

<400> SEQUENCE: 15
ccggccatgg cccagatcgt cctgacccag agcccg                                36

<210> SEQ ID NO 16
<211> LENGTH: 38
<212> TYPE: DNA
<213> ORGANISM: Artificial Sequence
<220> FEATURE:
<223> OTHER INFORMATION: synthetic primer

<400> SEQUENCE: 16
gccatggccg actctgtcct gacccagagc ccggcaag                              38

<210> SEQ ID NO 17
<211> LENGTH: 36
<212> TYPE: DNA
<213> ORGANISM: Artificial Sequence
<220> FEATURE:
<223> OTHER INFORMATION: synthetic primer

<400> SEQUENCE: 17
gtcctgaccc agccgccggc aagcctggct gtttcc                                36

<210> SEQ ID NO 18
<211> LENGTH: 36
<212> TYPE: DNA
<213> ORGANISM: Artificial Sequence
<220> FEATURE:
<223> OTHER INFORMATION: synthetic primer

<400> SEQUENCE: 18
acccagagcc cgtctagcct ggctgtttcc ctgggc                                36

<210> SEQ ID NO 19
<211> LENGTH: 36
<212> TYPE: DNA
<213> ORGANISM: Artificial Sequence
<220> FEATURE:
<223> OTHER INFORMATION: synthetic primer

<400> SEQUENCE: 19
ccggcaagcc tgtctgtttc cctgggccag cgtgcc                                36

<210> SEQ ID NO 20
<211> LENGTH: 36
<212> TYPE: DNA
<213> ORGANISM: Artificial Sequence
<220> FEATURE:
<223> OTHER INFORMATION: synthetic primer

<400> SEQUENCE: 20
```
ccagcgtgcc actatctcct gcagagcggg tgagtc                                    36

<210> SEQ ID NO 21
<211> LENGTH: 36
<212> TYPE: DNA
<213> ORGANISM: Artificial Sequence
<220> FEATURE:
<223> OTHER INFORMATION: synthetic primer

<400> SEQUENCE: 21
gaaaccgggt caggcgccaa aactgctgat ctatcg                                    36

<210> SEQ ID NO 22
<211> LENGTH: 36
<212> TYPE: DNA
<213> ORGANISM: Artificial Sequence
<220> FEATURE:
<223> OTHER INFORMATION: synthetic primer

<400> SEQUENCE: 22
gtccggcatc ccggaccgtt tctccggtac tggctc                                    36

<210> SEQ ID NO 23
<211> LENGTH: 39
<212> TYPE: DNA
<213> ORGANISM: Artificial Sequence
<220> FEATURE:
<223> OTHER INFORMATION: synthetic primer

<400> SEQUENCE: 23
gtacgtttct ccggttctgg ctctcgtact gattttacc                                 39

<210> SEQ ID NO 24
<211> LENGTH: 39
<212> TYPE: DNA
<213> ORGANISM: Artificial Sequence
<220> FEATURE:
<223> OTHER INFORMATION: synthetic primer

<400> SEQUENCE: 24
cgtttctccg gtactaaatc tcgtactgat tttaccctg                                 39

<210> SEQ ID NO 25
<211> LENGTH: 38
<212> TYPE: DNA
<213> ORGANISM: Artificial Sequence
<220> FEATURE:
<223> OTHER INFORMATION: synthetic primer

<400> SEQUENCE: 25
ccggtactgg ctctggtact gattttaccc tgattatc                                  38

<210> SEQ ID NO 26
<211> LENGTH: 38
<212> TYPE: DNA
<213> ORGANISM: Artificial Sequence
<220> FEATURE:
<223> OTHER INFORMATION: synthetic primer

<400> SEQUENCE: 26
ctggctctcg tactaccttt accctgatta tcgacccg                                  38

<210> SEQ ID NO 27
<211> LENGTH: 39
<212> TYPE: DNA
<213> ORGANISM: Artificial Sequence

```
<220> FEATURE:
<223> OTHER INFORMATION: synthetic primer

<400> SEQUENCE: 27
ggctctcgta ctgatgcgac cctgattatc gacccggtg                              39

<210> SEQ ID NO 28
<211> LENGTH: 39
<212> TYPE: DNA
<213> ORGANISM: Artificial Sequence
<220> FEATURE:
<223> OTHER INFORMATION: synthetic primer

<400> SEQUENCE: 28
actgatttta ccctgaccat cgacccggtg gaagcagac                              39

<210> SEQ ID NO 29
<211> LENGTH: 39
<212> TYPE: DNA
<213> ORGANISM: Artificial Sequence
<220> FEATURE:
<223> OTHER INFORMATION: synthetic primer

<400> SEQUENCE: 29
ttaccctgat tatctctccg gtggaagcag acgatgttg                              39

<210> SEQ ID NO 30
<211> LENGTH: 39
<212> TYPE: DNA
<213> ORGANISM: Artificial Sequence
<220> FEATURE:
<223> OTHER INFORMATION: synthetic primer

<400> SEQUENCE: 30
accctgatta tcgacggtgt ggaagcagac gatgttgcc                              39

<210> SEQ ID NO 31
<211> LENGTH: 39
<212> TYPE: DNA
<213> ORGANISM: Artificial Sequence
<220> FEATURE:
<223> OTHER INFORMATION: synthetic primer

<400> SEQUENCE: 31
gtggaagcag acgatgaagc cacctactat tgccagcag                              39

<210> SEQ ID NO 32
<211> LENGTH: 39
<212> TYPE: DNA
<213> ORGANISM: Artificial Sequence
<220> FEATURE:
<223> OTHER INFORMATION: synthetic primer

<400> SEQUENCE: 32
gcagacgatg ttgccgacta ctattgccag cagaccaac                              39

<210> SEQ ID NO 33
<211> LENGTH: 39
<212> TYPE: DNA
<213> ORGANISM: Artificial Sequence
<220> FEATURE:
<223> OTHER INFORMATION: synthetic primer

<400> SEQUENCE: 33
cggtactaaa ctgaccatca aaggcggtgg tggttctgg                              39
```

```
<210> SEQ ID NO 34
<211> LENGTH: 39
<212> TYPE: DNA
<213> ORGANISM: Artificial Sequence
<220> FEATURE:
<223> OTHER INFORMATION: synthetic primer

<400> SEQUENCE: 34
tactaaactg gaggttaaag gcggtggtgg ttctggtgg                        39

<210> SEQ ID NO 35
<211> LENGTH: 39
<212> TYPE: DNA
<213> ORGANISM: Artificial Sequence
<220> FEATURE:
<223> OTHER INFORMATION: synthetic primer

<400> SEQUENCE: 35
taaactggag atcctgggcg gtggtggttc tggtggtgg                        39

<210> SEQ ID NO 36
<211> LENGTH: 39
<212> TYPE: DNA
<213> ORGANISM: Artificial Sequence
<220> FEATURE:
<223> OTHER INFORMATION: synthetic primer

<400> SEQUENCE: 36
ggtgcggagc tcgttaaacc gggcgcttct gtgaaactg                        39

<210> SEQ ID NO 37
<211> LENGTH: 39
<212> TYPE: DNA
<213> ORGANISM: Artificial Sequence
<220> FEATURE:
<223> OTHER INFORMATION: synthetic primer

<400> SEQUENCE: 37
actgcatctg gtttcaccat taaggacacc tacatgcac                        39

<210> SEQ ID NO 38
<211> LENGTH: 39
<212> TYPE: DNA
<213> ORGANISM: Artificial Sequence
<220> FEATURE:
<223> OTHER INFORMATION: synthetic primer

<400> SEQUENCE: 38
gcatctggtt tcaacttcaa ggacacctac atgcactgg                        39

<210> SEQ ID NO 39
<211> LENGTH: 39
<212> TYPE: DNA
<213> ORGANISM: Artificial Sequence
<220> FEATURE:
<223> OTHER INFORMATION: synthetic primer

<400> SEQUENCE: 39
tctggtttca acatttctga cacctacatg cactgggtg                        39

<210> SEQ ID NO 40
<211> LENGTH: 39
<212> TYPE: DNA
<213> ORGANISM: Artificial Sequence
<220> FEATURE:
<223> OTHER INFORMATION: synthetic primer

<400> SEQUENCE: 40
```
tacatgcact gggtgagaca acgcccggaa cagggtctg          39

<210> SEQ ID NO 41
<211> LENGTH: 39
<212> TYPE: DNA
<213> ORGANISM: Artificial Sequence
<220> FEATURE:
<223> OTHER INFORMATION: synthetic primer

<400> SEQUENCE: 41
cactgggtga acaagcgcc ggaacagggt ctggagtgg          39

<210> SEQ ID NO 42
<211> LENGTH: 39
<212> TYPE: DNA
<213> ORGANISM: Artificial Sequence
<220> FEATURE:
<223> OTHER INFORMATION: synthetic primer

<400> SEQUENCE: 42
tgaaacaacg cccgggtcag ggtctggagt ggatcggtc          39

<210> SEQ ID NO 43
<211> LENGTH: 39
<212> TYPE: DNA
<213> ORGANISM: Artificial Sequence
<220> FEATURE:
<223> OTHER INFORMATION: synthetic primer

<400> SEQUENCE: 43
ccaaaattcc agggtagagc aaccatcact gctgatacc          39

<210> SEQ ID NO 44
<211> LENGTH: 39
<212> TYPE: DNA
<213> ORGANISM: Artificial Sequence
<220> FEATURE:
<223> OTHER INFORMATION: synthetic primer

<400> SEQUENCE: 44
aaattccagg gtaaattcac catcactgct gatacctcc          39

<210> SEQ ID NO 45
<211> LENGTH: 40
<212> TYPE: DNA
<213> ORGANISM: Artificial Sequence
<220> FEATURE:
<223> OTHER INFORMATION: synthetic primer

<400> SEQUENCE: 45
ctgctgatac ctccaaaaac actgcttacc tgcagctgac          40

<210> SEQ ID NO 46
<211> LENGTH: 39
<212> TYPE: DNA
<213> ORGANISM: Artificial Sequence
<220> FEATURE:
<223> OTHER INFORMATION: synthetic primer

<400> SEQUENCE: 46
gcttacctgc agctgaactc cctgactagc gaagacacc          39

<210> SEQ ID NO 47
<211> LENGTH: 41
<212> TYPE: DNA
<213> ORGANISM: Artificial Sequence -continued

```
<220> FEATURE:
<223> OTHER INFORMATION: synthetic primer

<400> SEQUENCE: 47
tttattactg cgctagattc ggctactatg tcagcgatta c                41

<210> SEQ ID NO 48
<211> LENGTH: 39
<212> TYPE: DNA
<213> ORGANISM: Artificial Sequence
<220> FEATURE:
<223> OTHER INFORMATION: synthetic primer

<400> SEQUENCE: 48
tattactgcg ctccgggtgg ctactatgtc agcgattac                  39

<210> SEQ ID NO 49
<211> LENGTH: 39
<212> TYPE: DNA
<213> ORGANISM: Artificial Sequence
<220> FEATURE:
<223> OTHER INFORMATION: synthetic primer

<400> SEQUENCE: 49
tggggtcagg gcaccctggt taccgtttct agcacaccg                  39

<210> SEQ ID NO 50
<211> LENGTH: 35
<212> TYPE: DNA
<213> ORGANISM: Artificial Sequence
<220> FEATURE:
<223> OTHER INFORMATION: synthetic primer

<400> SEQUENCE: 50
gattaccccg ctgatggcgg cccagtctgt tccag                      35

<210> SEQ ID NO 51
<211> LENGTH: 39
<212> TYPE: DNA
<213> ORGANISM: Artificial Sequence
<220> FEATURE:
<223> OTHER INFORMATION: synthetic primer

<400> SEQUENCE: 51
ctactggcgg gtttggcgcg tacgtggcct ttattcctg                  39
```

CAB MOLECULES

CROSS REFERENCE TO RELATED APPLICATIONS

The present application is a divisional application of U.S. patent application Ser. No. 10/590,870, filed Sep. 13, 2007, now U.S. Pat. No. 8,088,609, which is a U.S. National Stage Application of International Application No. PCT/US2005/012270, filed Apr. 12, 2005, which claims the benefit of U.S. Provisional Application Ser. Nos. 60/562,386, filed Apr. 15, 2004 and 60/636,002, filed Dec. 14, 2004, which are hereby incorporated by reference.

SEQUENCE LISTING

The sequence listing submitted via EFS, in compliance with 37 C.F.R. §1.52(e), is incorporated herein by reference. The sequence listing text file submitted via EFS contains the file "30839D1-SEQLIST-corr.txt" created on Jan. 5, 2012, which is 51,762 bytes in size.

FIELD OF THE INVENTION

The present invention relates to CAB molecules, ADEPT constructs directed against CEA and their use in therapy.

BACKGROUND

Traditional therapeutic molecules circulate freely throughout the body of patients until they are removed from circulation by the liver or another mechanism of clearance. Such non-targeted molecules can exert pharmocological effects indiscriminately on a wide range of cells and tissues. Indiscriminate targeting can cause serious side effects in a patient. The problem may be particularly acute when the molecule is highly toxic (e.g., in the case of a chemotherapeutic agent where the therapeutic window, the difference between an efficacious and injurious or even lethal dose, can be small).

In recent years, researchers have attempted to develop compounds that specifically affect particular groups of cells, tissues or organs. Most of the compounds target a particular tissue by preferentially binding a particular target molecule displayed by the tissue. By preferentially affecting targeted cells, tissues or organs, the therapeutic window can be increased, which in turn increases the opportunity for a successful treatment regimen and/or reduces the occurrence of side effects.

Preferential binding is employed in antibody-directed enzyme prodrug therapy (ADEPT). See, e.g., Xu et al., 2001, Clin Cancer Res. 7:3314-24; Denny, 2001, Eur J Med Chem. 36:577-95. In ADEPT, an antibody or antibody fragment is linked to an enzyme capable of converting an inactive prodrug into an active cytotoxic agent. An ADEPT conjugate is administered to a patient, and the conjugate is localized to a target tissue via antibody/antigen binding. The prodrug is subsequently administered, and the prodrug circulates throughout the patient's body but causes few or no side effects because the prodrug is in the inactive form and is activated by the ADEPT antibody-enzyme conjugate only in the vicinity of the target tissue. Thus, a relatively low concentration of active drug is present throughout the body, but a relatively high concentration of active drug is produced in the vicinity of the target tissue, increasing the therapeutic window of the toxin at the desired site.

In ADEPT, the antibody or antibody portion of a construct binds to an antigen to achieve localization, so selecting the proper antigen is important (e.g., an antigen that has a high tumor/normal expression profile). An antigen of particular interest frequently found on the cell surface in cancer tissues is carcinoembryonic antigen (CEA). CEA was first described by Gold and Freedman, J. Exp. Med., 121, 439-462, (1965). CEA is highly expressed in tumor tissue and also found at a lower concentration in some normal organs, particularly in the digestive tract.

Many antibodies to tumor antigens cross-react with related antigens. Systemic application of a MAb that is cross-reactive with a related antigen must be avoided to preclude risk of potentially severe side effects. Accordingly, the development of antigen-specific monoclonal antibodies for in vitro and in vivo diagnosis and therapy requires a good knowledge of the number, quality and biodistribution of related cross-reactive antigens. Careful immunochemical characterization of the MAb to be used is required with respect to its specificity and affinity for the target antigen and for related antigens.

Murine MAb T84.66 (ATCC Accession No. BH 8747) IgG1,k shows a high affinity constant to CEA and no cross reactivity to other members of the CEA gene family. A significant potential side effect of ADEPT therapy is the development of antibodies against the targeted enzyme during therapy. The production of human anti-mouse antibodies (HAMA) leads to reduced efficiency of the MAb and to potentially serious manifestations of acute and chronic allergic complications for the patient. See Levy, et al. Ann. Rev. Med. 34:107-116 (1983); Houghton, et al. Proc. Natl. Acad. Sci. USA, 82:1242-1246 (1985) and Sears, et al. J. Biol. Resp. Modifiers 3:138-150 (1984). Antibody formation has been observed during a clinical trial of a CEA-directed antibody-enzyme conjugate two weeks after treatment, which prevented subsequent rounds of treatment [Napier, M. P., S. K. Sharma, C. J. Springer, K. D. Bagshawe, A. J. Green, J. Martin, S. M. Stribbling, N. Cushen, D. O'Malley and R. H. Begent (2000) Clin Cancer Res 6, 765-72, Antibody-directed enzyme prodrug therapy: efficacy and mechanism of action in colorectal carcinoma].

The risk of eliciting an immune reaction is high for microbial proteins. The use of human enzymes for ADEPT has been investigated in pre-clinical studies [Smith, G. K., S. Banks, T. A. Blumenkopf, M. Cory, J. Humphreys, R. M. Laethem, J. Miller, C. P. Moxham, R. Mullin, P. H. Ray, L. M. Walton and L. A. Wolfe, 3rd (1997) J Biol Chem 272, 15804-16, Toward antibody-directed enzyme prodrug therapy with the T268G mutant of human carboxypeptidase A1 and novel in vivo stable prodrugs of methotrexate]. Although the risk of antibody formation can be reduced for human protein as compared to microbial protein, human proteins can also elicit immune reactions when administered to people. The consequences of eliciting an immune reaction against a human protein can be very significant, as such a treatment could trigger an auto-immune disease.

The risk of eciciting an immune reaction may be great for an ADEPT construct that contains at least two potential risks: the antibody portion and the enzyme portion.

SUMMARY OF THE INVENTION

The present invention relates to CAB molecules, ADEPT constructs directed against CEA and their use in therapy, especially with prodrugs as described herein. The molecules of the current invention have been preferably deimmunized and do not elicit an immune response and can be produced in high yield.

In a first aspect, the CAB molecule comprises an antibody/enzyme conjugate, wherein the antibody portion binds to CEA. In a preferred embodiment, the enzyme comprises a beta-lactamase.

In a preferred embodiment, the CAB molecule has an unmodified amino acid sequence. In a preferred embodiment, the CAB molecule has an amino acid sequence modified from the amino acid sequence set forth in SEQ ID NO:2, and the modification is located at least one of positions 12, 72, 283 or 586, wherein position numbering is with respect to SEQ ID NO:2 as shown in FIG. 4. In a preferred embodiment, the CAB molecule has both of the following modifications: 12 and 72. In a preferred embodiment, the CAB molecule has all of the following modifications: 12, 72, 283 and 586.

In a preferred embodiment, the CAB molecule has at least one of the following modifications: A12S, R72G, K283A or S586A, wherein position numbering is with respect to SEQ ID NO:2 as shown in FIG. 4. In a preferred embodiment, the CAB molecule comprises a CAB1.11 molecule, the CAB1.11 molecule comprising the following modifications: A12S and R72G. In a preferred embodiment, the CAB molecule comprises a CAB1.11i molecule, the CAB1.11i molecule comprising the following modifications: A12S, R72G, K283A and S586A.

In a preferred embodiment, the CAB molecule comprises CAB 1.10 having SEQ ID NO:2, CAB1.11 having SEQ ID NO:7 or CAB1.11i having SEQ ID NO:8.

In a second aspect, the invention is drawn to a nucleic acid encoding a CAB molecule as set forth herein. In a third aspect, the invention is drawn to treating a subject in need thereof, comprising administering to the subject a CAB molecule, as provided herein, and a prodrug that is a substrate of the CAB molecule. In a fourth aspect, the invention is drawn to a pharmaceutical composition comprising a CAB molecule.

BRIEF DESCRIPTION OF THE FIGURES

FIG. 1 sets forth unmodified sequences disclosed in the invention. FIG. 1A (SEQ ID NO:1) sets forth the amino acid sequence of the T84.66 antibody as described in Shively et al. and as disclosed in the invention provided herein; FIG. 1B sets forth the nucleotide sequence of the T84.66-derived antibody (SEQ ID NO:3); FIG. 1C sets forth the amino acid sequence for BLA (SEQ ID NO: 11); FIG. 1D sets forth the nucleotide sequence for BLA (SEQ ID NO:12); FIG. 1E sets forth the amino acid sequence for the 1.10 (SEQ ID NO: 2) construct that is T84.66 fused to BLA and includes a linker; FIG. 1F sets forth the nucleotide sequence for the 1.10 construct (SEQ ID NO:4). Underlining indicates the scFv portion of the molecule, and italics indicate the linker between the vl and vh portions of the scFv.

FIG. 2 sets forth the modified CAB 1.11 antibody portion of the current invention. FIG. 2A sets forth the amino acid sequence that has been modified and comprises a CAB 1.11 antibody portion (SEQ ID NO:5); FIG. 2B sets forth the nucleotide sequence sequence (SEQ ID NO:6) that has been modified and comprises a CAB 1.11 antibody portion.

FIG. 3 sets forth amino acid sequence of the deimmunized BLA portion (SEQ ID NO:13). Mutations from unmodified BLA (provided in FIG. 1) are shown in bold; numbering has been retained to remain consistent with the CAB1.11i construct.

FIG. 4 sets forth sequences for the CAB1.11 and CAB1.11i molecules. FIG. 4A sets forth the amino acid sequence of the CAB1.11 molecule (SEQ ID NO:7), which includes an antibody portion modified to improve expression, as described in the Examples, and also includes the BLA portion; FIG. 4B sets forth the nucleotide sequence of the CAB1.11 molecule (SEQ ID NO:9); FIG. 4C sets forth the amino acid sequence of the CAB1.11i molecule (SEQ ID NO:8), which includes the deimmunized BLA portion, as set forth in the Examples; FIG. 4D sets forth the nucleotide sequence that encodes the CAB1.11i molecule (SEQ ID NO:10), FIG. 4E sets forth the nucleotide sequence that encodes the plasmid, pHR19.2. In the Figure showing the CAB1.11i molecule, the scFv portion of the molecule has been underlined. The four mutations described in the Examples herein have been underlined. The linkers provided herein have been italicized. Two of the mutations are in the scFv portion of the molecule, and two of the mutations are in the BLA portion of the molecule.

FIG. 5 shows the plasmid map for pHR19.2.

FIG. 6 sets forth the binding of variants to target CEA. The x-axis shows the variant designation, as described herein, and the y-axis shows the % specific binding.

FIG. 7 shows a graph setting forth the results from the fermentation runs of EB101.1/pHR19.2 as set forth in Example 6. The x-axis shows EFT measured in hours, and the y-axis shows lactamase activity, measured in mg/L.

FIG. 8 sets forth the purification process for CAB1.11i, as described in Example 7.

FIG. 9 shows an SDS PAGE electrophoresis of CAB 1.11i. Lane 1 shows a molecular weight standard, lanes 3-5 show unrelated proteins and lane 6 shows 1.11i.

FIG. 10 shows binding and off-rate curves for CAB1.11i. FIG. 10A shows a binding curve, the x-axis showing amount, in nM, of CAB1.11i bound, and the y-axis shows how much CAB1.11i was added, again shown in nM. FIG. 10B shows off-rate, as described in Example 9, with time measured in minutes on the y-axis and percent BLA activity bound shown on the x-axis.

FIG. 11 shows CD, as set forth in Example 10.

FIG. 12 is a graph demonstrating tissue localization of CAB 1.11i. The x-axis shows time after administration, in hours, of the CAB 1.11i construct. The y-axis shows concentration in ug/g, of the CAB construct in different organs, as indicated by color, as shown in the chart at the right. The graph shows that CAB1.11i was eliminated rapidly from plasma, liver and kidney and localized to tumor.

FIG. 13 shows the tumor to blood ratio of CAB 1.11i. The x-axis shows time, in hours, after administration of the CAB 1.11i construct. The y-axis shows the level of tumor to blood. High tumor to blood ratios were achieved and sustained.

FIG. 14 shows demonstrated activity in a human colorectal cancer xenograft mouse model. The x-axis shows day number. The y-axis shows tumor volume measured in cubic millimeters. See, for example, Example 12.

FIG. 15 shows the results of IHC staining as set forth in Example 14. Column 1 shows Case ID; column 4 shows sample pathology; column 5 shows sample diagnosis; column 6 shows tissue of origin/site of finding; column 7 shows results of H&E staining, as set forth in Examples; column 8 shows results of staining against the control, human cytokeratin; columns 9-12 show results of staining against relevant CAB; column 13 shows results of no antibody staining.

FIG. 16 shows relevant plasma/tumor concentrations. FIG. 16A shows plasma and tumor CAB 1.11i concentration-time profiles (log-linear scale). The x-axis shows time, in hours, and the y-axis shows concentration. FIG. 16B shows dosing interval related to plasma GC-mel and melphalan exposure. Top right and left show GC-Mel and Mel, respectively, with the x-axis showing time, in hours, and the y-axis showing concentration. The bottom graphs, right and left, show GC- Mel and Mel, respectively, with the y-axis being the AUC and the bars, as indicated, being time, in hours.

FIG. 17 shows that plasma and kidney exposure to Mel is decreased woth increased interval between CAB 1.11i and GC-Mel doses. The x-axis shows AUC, and the y-axis shows time, in hours. Codes for kidney, plasma and tumor are indicated in the inset legend, at right.

FIG. 18 shows that efficacious tumor melphalan exposures are achieved at each time period while systemic melphalan exposure is decreased. The y-axis shows AUC, and the x-axis indicates the sample, plasma or tumor. Time is as set forth in the inset at the right of graph.

FIG. 19 shows the average tumor volume (19A) and average body weight (19B), as set forth in Example 16. The x-axis shows time, measured in days, and the y-axis shows tumor volume, measured in $mm^3$, and percent body weight change, respectively.

FIG. 21 shows the results of the dose-ranging efficacy study, as set forth in Example 18. The Figure shows efficacy of several dose levels of GC-mel, with the x-axis showing days post-CAB 1.11i dose, and the y-axis showing tumor volume, as measured in $mm^3$.

FIG. 22 shows the results of the dose ranging profile of GC-Mel administered after CAB1.11I in NCR nude mice bearing TLS174T xemograft tumors, specifically the average percent body weight loss, as set forth in Example 19. FIGS. 22A and 22B shows the average percent body weight loss with a dosing interval of 72 hours and 96 hours, respectively. The x-axis shows time in days, and the y-axis shows the average percent body weight change. The inset provides a key as to administered drug.

FIG. 23 shows CAB1.11i plasma concentration-time profile in rats as set forth in Example 20. The left graph shows female rats, and the right graph shows male rats. The x-axis shows time in hours, and the y-axis shows concentration of CAB1.11i.

FIG. 24 shows the pharmacokinetics of CAB1.11i following intravenous bolus administration to Sprague-Dawley rats. Specifically, FIG. 24A shows CAB1.11i concentration-time profiles in rats, as set forth in Example 21. The x-axis shows time in hours, and the y-axis shows concentration.

FIG. 25 shows CAB1.11i concentration-time profiles in cynomolgus monkey following 2 weekly doses. The x-axis shows time, in hours, and the y-axis shows concentration of CAB1.11i. The inset provides a legend, with F and M standing for female and male, respectively.

FIG. 26 shows CAB1.11i with or without CEA coadministration, as set forth in Example 22. The x-axis shows time, in hours, and the y-axis shows CAB1.11i concentration.

DETAILED DESCRIPTION OF THE INVENTION

Figure 20:
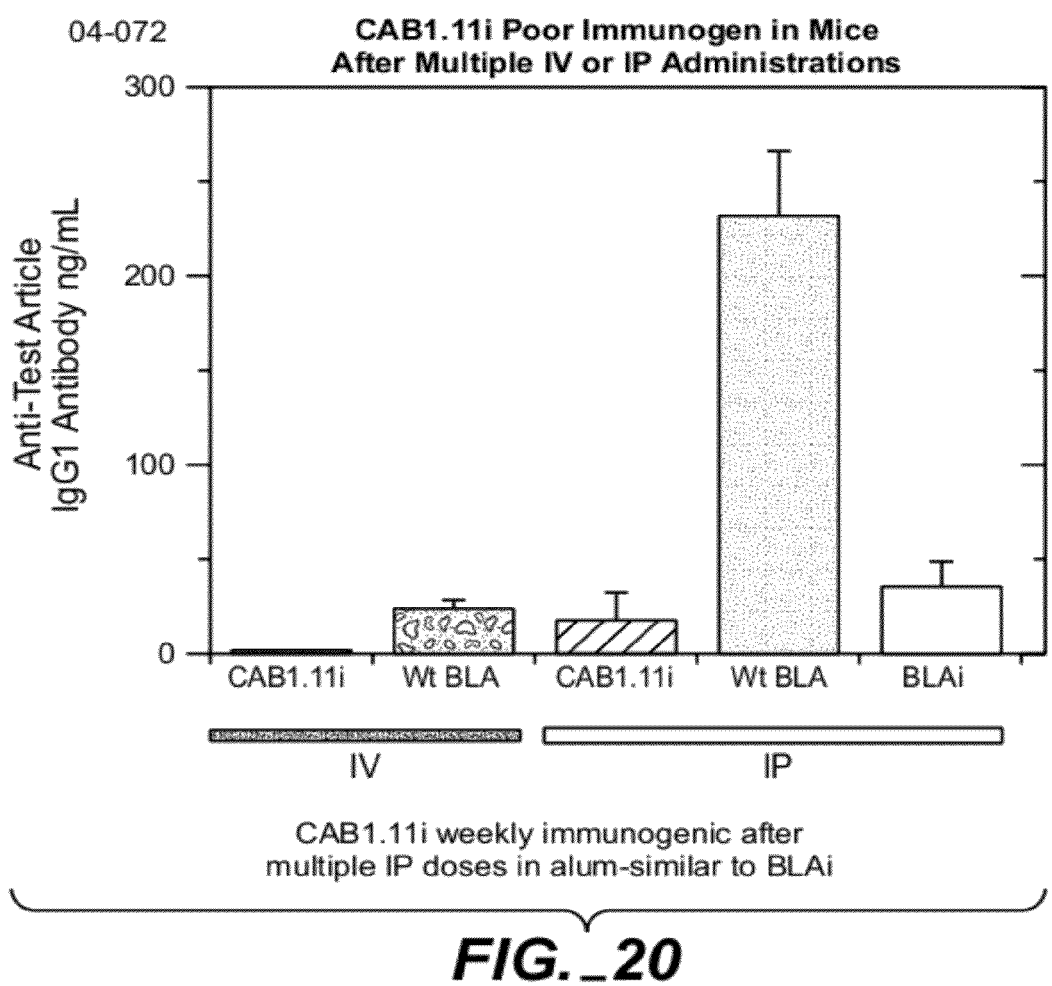
FIG. 20 shows the results of a possible or potential immunogen, specifically CAB1.11i or wt BLA administered IV or CAB1.11i, wt BLA or BLAi administered IP. The x-axis shows the molecule or test article or protein administered, and the y-axis shows response, as measured in IgG antibodies.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are used as described below.

"CAB" molecule shall mean a targeted agent that binds to a carcinoembryonic antigen (CEA) target or microtarget and an enzyme, such as BLA. A CAB molecule may have an unmodified sequence or a modified sequence, wherein the unmodified sequence comprises the amino acid sequence set forth in SEQ ID NO:2. SEQ ID NO:2 sets forth a CAB molecule that includes BLA as shown in FIG. 4. Position numbering as described in this document is with respect to SEQ ID NO:2, as set forth FIG. 4.

A "modified" sequence refers to a sequence that includes at least one mutation.

An "unmodified" sequence, as set forth herein, refers to a sequence that has not been modified and, thus, does not include at least one mutation, as set forth herein. Examples of unmodified sequences of the invention include, but may not be limited to, T84.66 (SEQ ID NO:1), CAB 1.10 (SEQ ID NO:2) and BLA (SEQ ID NO:11). Unmodified sequences may be modified, as described herein, to produce preferred embodiments of the invention.

A "targeted agent" is a chemical entity that binds selectively to a microtarget of interest. Examples of targeted agents are antibodies, peptides and inhibitors. Of interest are targeted enzymes that have a desired catalytic activity and that can bind to one or more target structures with high affinity and selectivity. Targeted enzymes retain at least most of their activity while bound to a target.

A "binding moiety" is a part of a targeted agent (or an ADEPT construct, e.g., CAB molecule) that binds a microtarget. A binding moiety can comprise more than one region, either contiguous or non-contiguous, of a CAB.

An "active moiety" is a part of a targeted agent (or an ADEPT construct, e.g., CAB molecule) that confers functionality to the agent. An active moiety can comprise more than one region, either contiguous or non-contiguous, of, for example, a CAB molecule. In particular, an active moiety can be a beta-lactamase.

The term "protein" is used interchangeably here with the terms "peptide" and "polypeptide," and refers to a molecule comprising two or more amino acid residues joined by a peptide bond.

The terms "cell", "cell line", and "cell culture" can be used interchangeably and all such designations include progeny. The words "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants. The cells can be prokaryotic or eukaryotic.

The term "oligonucleotide" as used herein is defined as a molecule comprised of two or more deoxyribonucleotides or ribonucleotides. The exact size will depend on many factors, which in turn depend on the ultimate function or use of the oligonucleotide. Oligonucleotides can be prepared by any suitable method, including, for example, cloning and restriction of appropriate sequences and direct chemical synthesis by a method such as the phosphotriester method of Narang et al., 1979, Meth. Enzymol. 68:90-99; the phosphodiester method of Brown et al., 1979, Meth. Enzymol. 68:109-151; the diethylphosphoramidite method of Beaucage et al., 1981, Tetrahedron Lett. 22:1859-1862; and the solid support method of U.S. Pat. No. 4,458,066, each incorporated herein by reference. A review of synthesis methods is provided in Goodchild, 1990, Bioconjugate Chemistry 1(3):165-187, incorporated herein by reference.

The term "primer" as used herein refers to an oligonucleotide capable of acting as a point of initiation of synthesis when placed under conditions in which primer extension is initiated. Synthesis of a primer extension product that is complementary to a nucleic acid strand is initiated in the presence of the requisite four different nucleoside triphosphates and a DNA polymerase in an appropriate buffer at a suitable temperature. A "buffer" includes a buffer, cofactors (such as divalent metal ions) and salt (to provide the appropriate ionic strength), adjusted to the desired pH.

A primer that hybridizes to the non-coding strand of a gene sequence (equivalently, is a subsequence of the noncoding strand) is referred to herein as an "upstream" or "forward" primer. A primer that hybridizes to the coding strand of a gene sequence is referred to herein as a "downstream" or "reverse" primer.

Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine), nonpolar side chains (e.g., alanine, valine, leucine, isoleucine, proline, phenylalanine, methionine, tryptophan, cysteine, glycine), beta-branched side chains (e.g., threonine, valine, isoleucine) and aromatic side chains (e.g., tyrosine, phenylalanine, tryptophan, histidine). Standard three-letter or one-letter amino acid abbreviations are used herein. Equivalent substitutions may be included within the scope of the claims.

The peptides, polypeptides and proteins of the invention can comprise one or more non-classical amino acids. Non-classical amino acids include but are not limited to the D-isomers of the common amino acids, α-amino isobutyric acid, 4-aminobutyric acid (4-Abu), 2-aminobutyric acid (2-Abu), 6-amino hexanoic acid (Ahx), 2-amino isobutyric acid (2-Aib), 3-amino propionoic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general.

The term "Ab" or "antibody" refers to polyclonal and monoclonal antibodies (MAb), chimeric antibodies, humanized antibodies, human antibodies, immunoglobulins or antibody or functional fragments of an antibody that binds to a target antigen. Examples of such functional entities include complete antibody molecules, antibody fragments, such as Fv, single chain Fv, complementarity determining regions (CDRs), $V_L$ (light chain variable region), $V_H$ (heavy chain variable region) and any combination of those or any other functional portion of an immunoglobulin peptide capable of binding to target antigen. In Example 1, the construct has the following order: vL-(GGGGS)$_6$-vH; however, the example is non-limiting, and all orders of vL and vH, are contemplated to be within the scope of the invention. Furthermore, the length of the linker need not be 30 amino acids in length, as disclosed herein, and different linker lengths are contemplated to be within the scope of the invention.

The term "prodrug" refers to a compound that is converted via one or more enzymatically-catalyzed or physiologically-catalyzed steps into an active compound that has an increased pharmacological activity relative to the prodrug. A prodrug can comprise a pro-part or inactive moiety and a drug or active drug or detectable moiety. Optionally, the prodrug also contains a linker. For example, the prodrug can be cleaved by an enzyme to release an active drug. Alternatively, an enzyme could alter the prodrug to release a detectable moiety. In a more specific example, prodrug cleavage by the targeted enzyme releases the active drug into the vicinity of the target bound to the targeted enzyme. "Pro-part" and "inactive moiety" refer to the inactive portion of the prodrug after it has been converted. For example, if a prodrug comprises a PEG molecule linked by a peptide to an active drug, the pro-part is the PEG moiety with or without a portion of the peptide linker.

As used herein, "GC-Mel" shall refer to the prodrug glutaryl-cephalosporin-melphalan as disclosed, for example, in Senter et al., U.S. Pat. No. 5,773,435, which is incorporated by reference herein, including any drawings The term "drug" and "active drug" and "detectable moiety" refer to the active moieties of a prodrug. After cleavage of the prodrug by a targeted enzyme, the active drug acts therapeutically upon the targeted tumor, cell, infectious agent or other agent of disease. The detectable moiety acts as a diagnostic tool, and such detectable moieties are intended to be within the scope of the claims. The active drug can be any chemical entity that is able to kill a cell, inhibit cell proliferation or act in concert with another drug to facilitate cell killing or inhibition of cell proliferation (e.g., drugs that predispose cells to apoptosis).

As used herein, "Mel" shall mean Melphalan. The structure of Mel is well known in the art and can also be found in U.S. Pat. No. 5,773,435.

As used herein, "dosing interval" shall mean the interval between administration of the protein and subsequent administration of the pro-drug. For example, in Example 20, dosing intervals of 72 and 96 hours are given, as set forth in Example 18.

As used herein, "cycle" shall mean the interval between one round or therapy of protein and prodrug and the next round, whatever that round may be The term "% sequence homology" is used interchangeably herein with the terms "% homology," "% sequence identity" and "% identity" and refers to the level of amino acid sequence identity between two or more peptide sequences, when aligned using a sequence alignment program. For example, as used herein, 80% homology means the same thing as 80% sequence identity determined by a defined algorithm, and accordingly, a homologue of a given sequence has greater than 80% sequence identity over a length of the given sequence. Exemplary levels of sequence identity include, but are not limited to, 60, 70, 80, 85, 90, 95, 98 or 99% or more sequence identity to a given sequence.

Exemplary computer programs that can be used to determine identity between two sequences include, but are not limited to, the suite of BLAST programs, e.g., BLASTN, BLASTX, and TBLASTX, BLASTP and TBLASTN, which are well-known to one skilled and the art. See also Altschul et al., 1990, *J. Mol. Biol.* 215: 403-10 and Altschul et al., 1997, *Nucleic Acids Res.,* 25:3389-3402. Sequence searches are typically carried out using the BLASTP program when evaluating a given amino acid sequence relative to amino acid sequences in the GenBank Protein Sequences and other public databases. The BLASTX program is preferred for searching nucleic acid sequences that have been translated in all reading frames against amino acid sequences in the GenBank Protein Sequences and other public databases. Both BLASTP and BLASTX are run using default parameters of an open gap penalty of 11.0, and an extended gap penalty of 1.0, and utilize the BLOSUM-62 matrix. See Altschul, et al., 1997.

A preferred alignment of selected sequences in order to determine "% identity" between two or more sequences, is performed using for example, the CLUSTAL-W program in MacVector version 6.5, operated with default parameters, including an open gap penalty of 10.0, an extended gap penalty of 0.1, and a BLOSUM 30 similarity matrix.

The present invention relates to CAB molecules, ADEPT constructs directed against CEA, and their use in therapy, especially with prodrugs as described herein. The molecules of the current invention have been preferably deimmunized and do not elicit an immune response.

In a first aspect, the CAB molecule comprises an antibody/enzyme conjugate, wherein the antibody portion binds to CEA. In a preferred embodiment, the enzyme comprises a beta-lactamase.

In a preferred embodiment, the CAB molecule has an unmodified amino acid sequence. In a preferred embodiment, the CAB molecule has an amino acid sequence modified from the amino acid sequence set forth in SEQ ID NO:2, and the modification is located at least one of positions 12, 72, 283 or 586, wherein position numbering is with respect to SEQ ID NO:2 as shown in FIG. 4. In a preferred embodiment, the CAB molecule has both of the following modifications: 12 and 72. In a preferred embodiment, the CAB molecule has all of the following modifications: 12, 72, 283 and 586.

In a preferred embodiment, the CAB molecule has at least one of the following modifications: A 12S, R72G, K283A or S586A, wherein position numbering is with respect to SEQ ID NO:2 as shown in FIG. 4. In a preferred embodiment, the CAB molecule comprises a CAB1.11 molecule, the CAB1.11 molecule comprising the following modifications: A12S and R72G. In a preferred embodiment, the CAB molecule comprises a CAB1.11i molecule, the CAB1.11i molecule comprising the following modifications: A12S, R72G, K283A and S586A.

In a preferred embodiment, the CAB molecule comprises CAB 1.10 having SEQ ID NO:2, CAB1.11 having SEQ ID NO:7 or CAB1.11i having SEQ ID NO:8.

In another embodiment, the CAB is an MDTA as described in PCT Application Number US03/18200, filed Jun. 12, 2002 and incorporated herein by reference in its entirety. Some of the CAB molecules of the present invention have been shown to preferentially bind to a microtarget present on a target relative to binding of a non-target. The difference in binding can be caused by any difference between the target and non-target such as, for example, a difference in pH, oxygen pressure, concentration of solutes or analytes (e.g., lactic acid, sugars or other organic or inorganic molecules), temperature, light or ionic strength. Preferential binding of the CABs of the current invention can be used to bind to a microtarget under a desired set of conditions, identify a target in vitro, ex vivo, in situ or in vivo (e.g., a target tissue in a subject), kill a target cell or tissue, convert a prodrug into an active drug in or near a target tissue. It also can be used as a surface catalyst, for example, a targeted laccase. Other uses include, e.g., targeted generation of a compound (e.g., $H_2O_2$ from glucose) and the targeted destruction of compounds (e.g., a metabolite or signalling molecule from a particular tissue).

In one embodiment, the CAB is selected, made or modified using an affinity maturation method, e.g., as described in PCT application US03/18187, with a priority date filed Jun. 12, 2002 and incorporated herein by reference in its entirety.

In another embodiment, the CAB is selected, made or modified using a loop-grafting method, e.g., as described in U.S. patent application Ser. No. 10/170,387, filed Jun. 12, 2002 and incorporated herein by reference in its entirety.

In another embodiment, the CAB is a multifunctional polypeptide, e.g., as described in U.S. patent application Ser. No. 10/170,729, filed Jun. 12, 2002 and incorporated herein by reference in its entirety.

In another embodiment, the CABs of the invention are used for diagnostic or therapeutic applications such as those disclosed, for example, in U.S. Pat. No. 4,975,278, which is incorporated herein by reference in its entirety, as well as methods well-known in the art.

In one embodiment, the CAB molecule further comprises an active moiety. The active moiety can be any molecule, or a part of a molecule, that has an activity. The activity can be any activity. Examples of types of activities that the active moiety can have include, for example, a detectable activity, an enzymatic activity, a therapeutic activity, a diagnostic activity, a toxic activity or a binding activity. The active moiety can be a discrete part of the CAB, for example, an enzyme that is fused or conjugated to the binding moiety, or it can be an integral part of the CAB, for example, binding of the CAB to the microtarget can activate or inhibit an activity of the microtarget or the target, or the CAB can be a targeted enzyme of the type discussed below and in copending U.S. patent application Ser. Nos. 10/022,073 and 10/022,097, incorporated herein by reference in their entireties.

In another embodiment, the active moiety exhibits enzymatic activity, e.g., it is an enzyme or an active fragment or derivative of an enzyme. Of particular interest are enzymes that can be used to activate a prodrug in a therapeutic setting. A large number of enzymes with different catalytic modes of action have been used to activate prodrugs. See, e.g., Melton & Knox Enzyme-prodrug strategies for cancer therapy (1999) and Bagshawe et al., *Curr Opin Immunol* 11:579 (1999). Examples of types of enzymes that can be used to make the CABs of the present invention include, but are not limited to, proteases, carboxypeptidases, β-lactamases, asparaginases, oxidases, hydrolases, lyases, lipases, cellulases, amylases, aldolases, phosphatases, kinases, tranferases, polymerases, nucleases, nucleotidases, laccases, reductases, and the like. See, e.g., co-pending U.S. patent application Ser. No. 09/954,385, filed Sep. 12, 2001, incorporated herein by reference in its entirety. As such, CABs of the invention can, for example, exhibit protease, carboxypeptidase, β-lactamase, asparaginase, oxidase, hydrolase, lyase, lipase, cellulase, amylase, aldolase, phospatase, kinase, tranferase, polymerase, nuclease, nucleotidase, laccase or reductase activity or the like. Examples of enzymes that can be used are those that can activate a prodrug, discussed below, and those that can produce a toxic agent from a metabolite, e.g., hydrogen peroxide from glucose. See Christofidou-Solomidou et al, 2000, *Am J Physiol Lung Cell Mol Physiol* 278: L794.

In one embodiment, the present invention provides a CAB further comprising a β-lactamase ("BLA"). In another embodiment, the BLA is a targeted enzyme as described in co-pending U.S. patent application Ser. Nos. 10/022,073 and 10/022,097, incorporated herein by reference in their entirety.

BLA enzymes are widely distributed in both gram-negative and gram-positive bacteria. BLA sequences are well known. A representative example of a BLA sequence is depicted in FIG. 3. BLA enzymes vary in specificity, but have in common that they to hydrolyze β-lactams, producing substituted β-amino acids. Thus, they confer resistance to antibiotics containing β-lactams. Because BLA enzymes are not endogenous to mammals, they are subject to minimal interference from inhibitors, enzyme substrates, or endogenous enzyme systems (unlike proteases), and therefore are particularly well-suited for therapeutic administration. BLA enzymes are further well-suited to the therapeutic methods of the present invention because of their small size (BLA from *E. cloacae* is a monomer of 39 kD; BLA from *E. coli* is a monomer of 30 kD) and because they have a high specific activity against their substrates and have optimal activity at 37° C. See Melton et al., Enzyme-Prodrug Strategies for Cancer Therapy, Kluwer Academic/Plenum Publishers, New York (1999).

Examples of specific BLAs that can be used to make the CABs of the present invention include, but are not limited to, Class A, B, C or D β-lactamase, β-galactosidase, see Benito et al., *FEMS Microbiol. Lett.* 123:107 (1994), fibronectin, glucose oxidase, glutathione S-transferase, see Napolitano et al., *Chem. Biol.* 3:359 (1996) and tissue plasminogen activator, see Smith et al., *J. Biol. Chem.* 270:30486 (1995). The β-lactamases have been divided into four classes based on their sequences. See Thomson et al., 2000, *Microbes and Infection* 2:1225-35. The serine β-lactamases are subdivided into three classes: A (penicillinases), C (cephalosporinases) and D (oxacillnases). Class B β-lactamases are the zinc-containing or metallo β-lactamases. Any class of BLA can be utilized to generate a CAB of the invention.

In one embodiment of the invention, the BLA has a specific activity greater than about 0.01 U/pmol against nitrocefin using the assay described in U.S. patent application Ser. No. 10/022,097. In another embodiment, the specific activity is greater than about 0.1 U/pmol. In another embodiment, the specific activity is greater than about 1 U/pmol. Preferably, these specific activities refer to the specific activity of the BLA when it is bound to a microtarget.

In one embodiment, the BLA enzyme in the CAB comprises the amino acid sequence set forth in SEQ ID NO:11. In another embodiment, the BLA enzyme in the CAB is at least 50%, 60%, 70%, 80%, 90%, 95%, 98% or 99% or more identical to the sequence depicted in FIG. 4.

In a preferred embodiment, the CAB is CAB1.11 or CAB1.11i.

The targets bound by the CAB, or one or more binding moieties, can be any substance or composition to which a molecule can be made to bind to CEA. In one embodiment, the target is a surface. In one embodiment, the surface is a biological surface. In another embodiment, the biological surface is a surface of an organ. In another embodiment, the biological surface is a surface of a tissue. In another embodiment, the biological surface is a surface of a cell. In another embodiment, the biological surface is a surface of a diseased organ, tissue or cell. In another embodiment, the biological surface is a surface of a normal or healthy organ, tissue or cell. In another embodiment, the surface is a macromolecule in the interstitial space of a tissue. In another embodiment, the biological surface is the surface of a virus or pathogen. In another embodiment, the surface is a non-biological surface. In another embodiment, the non-biological surface is a surface of a medical device. In another embodiment, the medical device is a therapeutic device. In another embodiment, the therapeutic device is an implanted therapeutic device. In another embodiment, the medical device is a diagnostic device. In another embodiment, the diagnostic device is a well or tray.

Sources of cells or tissues include human, all other animals, bacteria, fungi, viruses and plant. Tissues are complex targets and refer to a single cell type, a collection of cell types or an aggregate of cells generally of a particular kind. Tissue may be intact or modified. General classes of tissue in humans include but are not limited to epithelial tissue, connective tissue, nerve tissue and muscle tissue.

In another embodiment, the target is a cancer-related target that expresses CEA or that has CEA bound to itself or that has CEA located in its vicinity. The cancer-related target can be any target that a composition of the invention binds to as part of the diagnosis, detection or treatment of a cancer or cancer-associated condition in a subject, for example, a cancerous cell, tissue or organ, a molecule associated with a cancerous cell, tissue or organ, or a molecule, cell, tissue or organ that is associated with a cancerous cell, tissue or organ (e.g., a tumor-bound diagnostic or therapeutic molecule administered to a subject or to a biopsy taken from a subject, or a healthy tissue, such as vasculature, that is associated with cancerous tissue).

In a second aspect, the invention is drawn to a nucleic acid encoding a CAB molecule as set forth herein. The nucleic acid can be, for example, a DNA or an RNA. The present invention also provides a plasmid comprising a nucleic acid encoding a polypeptide comprising all or part of a CAB. The plasmid can be, for example, an expression plasmid that allows expression of the polypeptide in a host cell or organism, or in vitro. The expression vector can allow expression of the polypeptide in, for example, a bacterial cell. The bacterial cell can be, for example, an *E. coli* cell.

Because of the redundancy in the genetic code, typically a large number of DNA sequences encode any given amino acid sequence and are, in this sense, equivalent. As described below, it may be desirable to select one or another equivalent DNA sequences for use in an expression vector, based on the preferred codon usage of the host cell into which the expression vector will be inserted. The present invention is intended to encompass all DNA sequences that encode the desired CAB.

An operable expression clone may be used and is constructed by placing the coding sequence in operable linkage with a suitable control sequence in an expression vector. The vector can be designed to replicate autonomously in the host cell or to integrate into the chromosomal DNA of the host cell. The resulting clone is used to transform a suitable host, and the transformed host is cultured under conditions suitable for expression of the coding sequence. The expressed CAB is then isolated from the medium or from the cells, although recovery and purification of the CAB may not be necessary in some instances.

Construction of suitable clones containing the coding sequence and a suitable control sequence employ standard ligation and restriction techniques that are well understood in the art. In general, isolated plasmids, DNA sequences or synthesized oligonucleotides are cleaved, modified and religated in the form desired. Suitable restriction sites can, if not normally available, be added to the ends of the coding sequence so as to facilitate construction of an expression clone.

Site-specific DNA cleavage is performed by treating with a suitable restriction enzyme (or enzymes) under conditions that are generally understood in the art and specified by the manufacturers of commercially available restriction enzymes. See, e.g., product catalogs from Amersham (Arlington Heights, Ill.), Roche Molecular Biochemicals (Indianapolis, Ind.), and New England Biolabs (Beverly, Mass.). Incubation times of about one to two hours at a temperature that is optimal for the particular enzyme are typical. After each incubation, protein is removed by extraction with phenol and chloroform; this extraction can be followed by ether extraction and recovery of the DNA from aqueous fractions by precipitation with ethanol. If desired, size separation of the cleaved fragments may be performed by polyacrylamide gel or agarose gel electrophoresis using standard techniques. See, e.g., Maxam et al., 1980, Methods in Enzymology 65:499-560.

Ligations can be performed, for example, in 15-30 μl volumes under the following standard conditions and temperatures: 20 mM Tris-Cl, pH 7.5, 10 mM $MgCl_2$, 10 mM DTT, 33

µg/ml BSA, 10-50 mM NaCl, and either 40 µM ATP and 0.01-0.02 (Weiss) units T4 DNA ligase at 0° C. (for ligation of fragments with complementary single-stranded ends) or 1 mM ATP and 0.3-0.6 units T4 DNA ligase at 14° C. (for "blunt end" ligation). Intermolecular ligations of fragments with complementary ends are usually performed at 33-100 µg/ml total DNA concentrations (5-100 nM total ends concentration). Intermolecular blunt end ligations (usually employing a 20-30 fold molar excess of linkers, optionally) are performed at 1 µM total ends concentration.

Correct ligations for plasmid construction can be confirmed using any suitable method known in the art. For example, correct ligations for plasmid construction can be confirmed by first transforming a suitable host, such as *E. coli* strain DG101 (ATCC 47043) or *E. coli* strain DG116 (ATCC 53606), with the ligation mixture. Successful transformants are selected by ampicillin, tetracycline or other antibiotic resistance or sensitivity or by using other markers, depending on the mode of plasmid construction, as is understood in the art. Plasmids from the transformants are then prepared according to the method of Clewell et al., 1969, Proc. Natl. Acad. Sci. USA 62:1159, optionally following chloramphenicol amplification. See Clewell, 1972, J. Bacteriol. 110: 667. Alternatively, plasmid DNA can be prepared using the "Base-Acid" extraction method at page 11 of the Bethesda Research Laboratories publication Focus 5 (2), and very pure plasmid DNA can be obtained by replacing steps 12 through 17 of the protocol with CsCl/ethidium bromide ultracentrifugation of the DNA. As another alternative, a commercially available plasmid DNA isolation kit, e.g., HISPEED™, QIAFILTER™ and QIAGEN® plasmid DNA isolation kits (Qiagen, Valencia Calif.) can be employed following the protocols supplied by the vendor. The isolated DNA can be analyzed by, for example, restriction enzyme digestion and/or sequenced by the dideoxy method of Sanger et al., 1977, Proc. Natl. Acad. Sci. USA 74:5463, as further described by Messing et al., 1981, Nuc. Acids Res. 9:309, or by the method of Maxam et al., 1980, Methods in Enzymology 65:499.

The control sequences, expression vectors and transformation methods are dependent on the type of host cell used to express the gene. Generally, prokaryotic, yeast, insect or mammalian cells are used as hosts. Prokaryotic hosts are in general the most efficient and convenient for the production of recombinant proteins and are therefore preferred for the expression of the protein.

The prokaryote most frequently used to express recombinant proteins is *E. coli*. However, microbial strains other than *E. coli* can also be used, such as bacilli, for example *Bacillus subtilis*, various species of *Pseudomonas* and *Salmonella*, and other bacterial strains. In such prokaryotic systems, plasmid vectors that contain replication sites and control sequences derived from the host or a species compatible with the host are typically used.

For expression of constructions under control of most bacterial promoters, *E. coli* K12 strain MM294, obtained from the *E. coli* Genetic Stock Center under GCSC #6135, can be used as the host. For expression vectors with the $P_L N_{RBS}$ or $P_L T7_{RBS}$ control sequence, *E. coli* K12 strain MC1000 lambda lysogen, $N_7 N_{53} cI857$ $SusP_{80}$, ATCC 39531, may be used. *E. coli* DG116, which was deposited with the ATCC (ATCC 53606) on Apr. 7, 1987, and *E. coli* KB2, which was deposited with the ATCC (ATCC 53075) on Mar. 29, 1985, are also useful host cells. For M13 phage recombinants, *E. coli* strains susceptible to phage infection, such as *E. coli* K12 strain DG98 (ATCC 39768), are employed. The DG98 strain was deposited with the ATCC on Jul. 13, 1984.

For example, *E. coli* is typically transformed using derivatives of pBR322, described by Bolivar et al., 1977, Gene 2:95. Plasmid pBR322 contains genes for ampicillin and tetracycline resistance. These drug resistance markers can be either retained or destroyed in constructing the desired vector and so help to detect the presence of a desired recombinant. Commonly used prokaryotic control sequences, i.e., a promoter for transcription initiation, optionally with an operator, along with a ribosome binding site sequence, include the β-lactamase (penicillinase) and lactose (lac) promoter systems, see Chang et al., 1977, Nature 198:1056, the tryptophan (trp) promoter system, see Goeddel et al., 1980, Nuc. Acids Res. 8:4057, and the lambda-derived $P_L$ promoter, see Shimatake et al., 1981, Nature 292:128, and gene N ribosome binding site ($N_{RBS}$). A portable control system cassette is set forth in U.S. Pat. No. 4,711,845, issued Dec. 8, 1987. This cassette comprises a $P_L$ promoter operably linked to the $N_{RBS}$ in turn positioned upstream of a third DNA sequence having at least one restriction site that permits cleavage within six base pairs 3' of the $N_{RBS}$ sequence. Also useful is the phosphatase A (phoA) system described by Chang et al., in European Patent Publication No. 196,864, published Oct. 8, 1986. However, any available promoter system compatible with prokaryotes can be used to construct a expression vector of the invention.

In addition to bacteria, eukaryotic microbes, such as yeast, can also be used as recombinant host cells. Laboratory strains of *Saccharomyces cerevisiae*, Baker's yeast, are most often used, although a number of other strains are commonly available. While vectors employing the two micron origin of replication are common, see Broach, 1983, Meth. Enz. 101:307, other plasmid vectors suitable for yeast expression are known. See, e.g., Stinchcomb et al., 1979, Nature 282:39; Tschempe et al., 1980, Gene 10:157; and Clarke et al., 1983, Meth. Enz. 101:300. Control sequences for yeast vectors include promoters for the synthesis of glycolytic enzymes. See Hess et al., 1968, J. Adv. Enzyme Reg. 7:149; Holland et al., 1978, Biotechnology 17:4900; and Holland et al., 1981, J. Biol. Chem. 256:1385. Additional promoters known in the art include the promoter for 3-phosphoglycerate kinase, see Hitzeman et al., 1980, J. Biol. Chem. 255:2073, and those for other glycolytic enzymes, such as glyceraldehyde 3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase and glucokinase. Other promoters that have the additional advantage of transcription controlled by growth conditions are the promoter regions for alcohol dehydrogenase 2, isocytochrome C, acid phosphatase, degradative enzymes associated with nitrogen metabolism and enzymes responsible for maltose and galactose utilization.

Terminator sequences may also be used to enhance expression when placed at the 3' end of the coding sequence. Such terminators are found in the 3' untranslated region following the coding sequences in yeast-derived genes. Any vector containing a yeast-compatible promoter, origin of replication and other control sequences is suitable for use in constructing yeast expression vectors.

The coding sequence can also be expressed in eukaryotic host cell cultures derived from multicellular organisms. See, e.g., Tissue Culture, Academic Press, Cruz and Patterson, editors (1973). Useful host cell lines include COS-7, COS-A2, CV-1, murine cells such as murine myelomas N51 and VERO, HeLa cells and Chinese hamster ovary (CHO) cells. Expression vectors for such cells ordinarily include promoters and control sequences compatible with mammalian cells such as, for example, the commonly used early and late promoters from Simian Virus 40 (SV 40), see Fiers et al., 1978, Nature 273:113, or other viral promoters such as those derived from polyoma, adenovirus 2, bovine papilloma virus (BPV) or avian sarcoma viruses, or immunoglobulin promoters and heat shock promoters.

Enhancer regions are also important in optimizing expression; these are, generally, sequences found upstream of the promoter region. Origins of replication may be obtained, if needed, from viral sources. However, integration into the chromosome is a common mechanism for DNA replication in eukaryotes.

Plant cells can also be used as hosts, and control sequences compatible with plant cells, such as the nopaline synthase promoter and polyadenylation signal sequences, see Depicker et al., 1982, J. Mol. Appl. Gen. 1:561, are available. Expression systems employing insect cells utilizing the control systems provided by baculovirus vectors have also been described. See Miller et al., in Genetic Engineering (1986), Setlow et al., eds., Plenum Publishing, Vol. 8, pp. 277-97. Insect cell-based expression can be accomplished in *Spodoptera frugipeida*. These systems are also successful in producing recombinant enzymes.

Depending on the host cell used, transformation is done using standard techniques appropriate to such cells. The calcium treatment employing calcium chloride, as described by Cohen, 1972, Proc. Natl. Acad. Sci. USA 69:2110, is used for prokaryotes or other cells that contain substantial cell wall barriers. Infection with *Agrobacterium tumefaciens*, see Shaw et al., 1983, Gene 23:315, is used for certain plant cells. For mammalian cells, the calcium phosphate precipitation method of Graham et al., 1978, Virology 52:546 is preferred. Transformations into yeast are carried out according to the method of Van Solingen et al., 1977, J. Bact. 130:946, and Hsiao et al., 1979, Proc. Natl. Acad. Sci. USA 76:3829.

It may be desirable to modify the sequence of a DNA encoding a polypeptide comprising all or part of a CAB of the invention to provide, for example, a sequence more compatible with the codon usage of the host cell without modifying the amino acid sequence of the encoded protein. Such modifications to the initial 5-6 codons may improve expression efficiency. DNA sequences which have been modified to improve expression efficiency, but which encode the same amino acid sequence, are considered to be equivalent and encompassed by the present invention.

A variety of site-specific primer-directed mutagenesis methods are available and well-known in the art. See, e.g., Sambrook et al., Molecular Cloning: A Laboratory Manual, Cold Spring Harbor, 1989, second edition, chapter 15.51, "Oligonucleotide-mediated mutagenesis," which is incorporated herein by reference. The polymerase chain reaction (PCR) can be used to perform site-specific mutagenesis. In another technique now standard in the art, a synthetic oligonucleotide encoding the desired mutation is used as a primer to direct synthesis of a complementary nucleic acid sequence contained in a single-stranded vector, such as pBSM13+ derivatives, that serves as a template for construction of the extension product of the mutagenizing primer. The mutagenized DNA is transformed into a host bacterium, and cultures of the transformed bacteria are plated and identified. The identification of modified vectors may involve transfer of the DNA of selected transformants to a nitrocellulose filter or other membrane and the "lifts" hybridized with kinased synthetic mutagenic primer at a temperature that permits hybridization of an exact match to the modified sequence but prevents hybridization with the original unmutagenized strand. Transformants that contain DNA that hybridizes with the probe are then cultured (the sequence of the DNA is generally confirmed by sequence analysis) and serve as a reservoir of the modified DNA.

Once the polypeptide has been expressed in a recombinant host cell, purification of the polypeptide may be desired. A variety of purification procedures can be used.

In another embodiment, a nucleic acid encoding the CAB hybridizes to a nucleic acid complementary to a nucleic acid encoding any of the amino acid sequences disclosed herein under highly stringent conditions. The highly stringent conditions can be, for example, hybridization to filter-bound DNA in 0.5 M $NaHPO_4$, 7% sodium dodecyl sulfate (SDS), 1 mM EDTA at 65° C. and washing in 0.1×SSC/0.1% SDS at 68° C. (Ausubel et al., eds., 1989, *Current Protocols in Molecular Biology*, Vol. I, Green Publishing Associates, Inc., and John Wiley & Sons, Inc., New York, at p. 2.10.3). Other highly stringent conditions can be found in, for example, *Current Protocols in Molecular Biology*, at pages 2.10.1-16 and *Molecular Cloning: A Laboratory Manual*, 2d ed., Sambrook et al. (eds.), Cold Spring Harbor Laboratory Press, 1989, pages 9.47-57. In another embodiment, moderately stringent conditions are used. The moderately stringent conditions can be, for example, washing in 0.2×SSC/0.1% SDS at 42° C. (Ausubel et al., 1989, supra). Other moderately stringent conditions can be found in, for example, *Current Protocols in Molecular Biology*, Vol. I, Ausubel et al. (eds.), Green Publishing Associates, Inc., and John Wiley & Sons, Inc., 1989, pages 2.10.1-16 and *Molecular Cloning: A Laboratory Manual*, 2d ed., Sambrook et al. (eds.), Cold Spring Harbor Laboratory Press, 1989, pages 9.47-57.

In a third aspect the present invention provides a method of treating a subject in need thereof comprising administering to a subject a CAB and a prodrug that is a substrate of the CAB. In another embodiment, the invention provides a method of treating a subject by administering to the subject a CAB, further comprising a BLA, and a prodrug that is converted by the BLA into an active drug. In another embodiment, the CAB is specifically CAB1.11 or CAB1.11i.

Melphalan derivatives are especially suitable as the prodrug for this embodiment of the invention. Examples of enzyme/prodrug/active drug combinations can be found in, e.g., Senter et al., U.S. Pat. No. 5,773,435, which is incorporated by reference herein, including any drawings. Other examples of suitable prodrugs for this embodiment are provided in, e.g., Melton et al., Enzyme-Prodrug Strategies for Cancer Therapy, Kluwer Academic/Plenum Publishers, New York (1999), Bagshawe et al., *Current Opinion in Immunology* 11:579-83 (1999) and Kerr et al., *Bioconjugate Chem.* 9:255-59 (1998). Wil-man, "Prodrugs In Cancer Chemotherapy," *Biochemical Society Transactions*, 14, pp. 375-82 (615th Meeting, Belfast 1986) and V. J. Stella et al., "Prodrugs: A Chemical Approach To Targeted Drug Delivery," *Directed Drug Delivery*, R. Borchardt et al. (ed), pp. 247-67 (Humana Press 1985).

In one embodiment, the prodrug is a peptide. Examples of peptides as prodrugs can be found in Trouet et al., *Proc Natl Acad Sci USA* 79:626 (1982), and Umemoto et al., *Int J Cancer* 43:677 (1989). These and other reports show that peptides are sufficiently stable in blood. Another advantage of peptide-derived prodrugs is their amino acid sequences can be chosen to confer suitable pharmacological properties like half-life, tissue distribution and low toxicity to the active drugs. Most reports of peptide-derived prodrugs relied on relatively nonspecific activation of the prodrug by, for instance, lysosomal enzymes.

The prodrug can be one that is converted to an active drug in more than one step. For example, the prodrug can be converted to a precursor of an active drug by the CAB. The precursor can be converted into the active drug by, for example, the catalytic activity of one or more additional CABs, the catalytic activities of one or more other enzymes administered to the subject, the catalytic activity of one or more enzymes naturally present in the subject or at the target site in the subject (e.g., a protease, a phosphatase, a kinase or a polymerase), by a drug that is administered to the subject or by a chemical process that is not enzymatically catalyzed (e.g., oxidation, hydrolysis, isomerization or epimerization).

Most studies involving prodrugs are generated after programs with existing drugs are found to be problematic. In particular anticancer drugs were generally characterized by a very low therapeutic index. By converting these drugs into prodrugs with reduced toxicity and then selectively activating them in the diseased tissue, the therapeutic index of the drug was significantly increased. See, e.g., Melton et al., Enzyme-prodrug strategies for cancer therapy (1999), and Niculescu-Duvaz et al., *Anticancer Drug Des* 14:517 (1999).

The literature describes many methods to alter the substrate specificity of enzymes by protein engineering or directed evolution. Thus one skilled in the art is able to evolve the specificity of an enzyme to accommodate even structures that would be poor substrates for naturally-occurring enzymes. Accordingly, prodrugs can be designed even though the drugs were otherwise not amenable to a prodrug strategy.

The prodrugs of the invention can include, but are not limited to, auristatins, camptothecins, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted by the enzyme of the conjugate into the more active cytotoxic free drug. Examples of cytotoxic drugs that can be derivatized into a prodrug form for use in this invention include, but are not limited to, etoposide, temposide, adriamycin, daunomycin, caminomycin, aminopterin, dactinomycin, mitomycins, cis-platinum and cis-platinum analogues, bleomycins, esperamicins (see U.S. Pat. No. 4,675,187), 5-fluorouracil, melphalan, other related nitrogen mustards and derivatives thereof. (See, e.g., U.S. Pat. No. 4,975,278).

In one embodiment of the invention, the CAB comprises an alkaline phosphatase (AP) that converts a 4'-phosphate derivative of the epipodophyl-lotoxin glucosides into an active anti-cancer drug. Such derivatives include etoposide-4'-phosphate, etoposide-4'-thiophosphate and teniposide-4'-phosphate. Other embodiments of the invention may include phosphate derivatives of these glucosides wherein the phosphate moiety is placed at other hydroxyl groups on the glucosides. According to another embodiment, however, the phosphate derivative used as a pro-drug in this invention is etoposide-4'-phosphate or etoposide-4'-thiophosphate. The targeted AP removes the phosphate group from the prodrug, releasing an active antitumor agent. The mitomycin phosphate prodrug of this embodiment may be an $N^7$—$C_{1-8}$ alkyl phosphate derivative of mitomycin C or porfiromycin or pharmaceutically acceptable salts thereof. $N^7$ refers to the nitrogen atom attached to the 7-position of the mitosane nucleus of the parent drug. According to another embodiment, the derivative used is 7-(2'-aminoethylphosphate)mitomycin ("MOP"). Alternatively, the MOP compound may be termed, 9-methoxy-7-[[(phos-phonooxy)ethyl]amino]mitosane disodium salt. Other embodiments of the invention may include the use of $N^7$-alkyl mitomycin phosphorothioates as prodrugs.

In still another embodiment of the invention, the CAB comprises a penicillin amidase enzyme that converts a novel adriamycin prodrug into the active antitumor drug adriamycin. In another embodiment, the penicillin amidase is a penicillin V amidase ("PVA") isolated from *Fusarium oxysporum* that hydrolyzes phenoxyacetyl amide bonds. The prodrug utilized can be N-(p-hydroxyphenoxyacetyl)adriamycin ("APO"), which is hydrolyzed by the amidase to release the potent antitumor agent or adriamycin.

The present invention also comprises, for example, the use of the adriamycin prodrug, N-(p-hydroxyphenoxyacetyl) adriamycin and other related adriamycin prodrugs that can be derivatized in substantially the same manner. For example, use of the prodrug N-(phenoxyacetyl) adriamycin is also within the scope of the invention. In addition, it is to be understood that the adriamycin prodrugs of this invention include other N-hydroxyphenoxyacetyl derivatives of adriamycin, e.g., substituted at different positions of the phenyl ring, as well as N-phenoxyacetyl derivatives containing substituents on the phenyl ring other than the hydroxyl group described herein.

Furthermore, the present embodiment encompasses the use of other amidases, such as penicillin G amidase, as part of the CAB as well as other prodrugs correspondingly derivatized such that the particular amidase can hydrolyze that prodrug to an active antitumor form. For example, when the CAB further comprises penicillin G amidase, the prodrug should contain a phenylacetylamide group (as opposed to the phenoxyacetylamide group of APO) because penicillin G amidases hydrolyze this type of amide bond (see, e.g., A. L. Margolin et al., *Biochim. Biophys Acta.* 616, pp. 283-89 (1980)). Thus, other prodrugs of the invention include N-(p-hydroxyphenylacetyl) adriamycin, N-(phenylacetyl) adriamycin and other optionally substituted N-phenylacetyl derivatives of adriamycin.

It should also be understood that the present invention includes any prodrug derived by reacting the amine group of the parent drug with the carboxyl group of phenoxyacetic acid, phenylacetic acid or other related acids. Thus, prodrugs of anthracyclines other than adriamycin that are capable of being derivatized and acting in substantially the same manner as the adriamycin prodrugs described herein falls within the scope of this invention. For example, other prodrugs that can be produced and used in accordance with this invention include hydroxyphenoxyacetylamide derivatives, hydroxyphenylacetylamide derivatives, phenoxyacetamide derivatives and phenylacetylamide derivatives of anthracyclines such as daunomycin and caminomycin. Other amine-containing drugs such as melphalan, mitomycin, aminopterin, bleomycin and dactinomycin can also be modified described herein to yield prodrugs of the invention.

Another embodiment of the invention involves a CAB form of the enzyme cytosine deaminase ("CD"). The deaminase enzyme catalyzes the conversion of 5-fluorocytosine ("5-FC"), a compound lacking in antineoplastic activity, to the potent antitumor drug, 5-fluorouracil ("5-FU").

Another embodiment of the method of this invention provides a method of combination chemotherapy using several prodrugs and a single CAB. According to this embodiment, a number of prodrugs are used that are all substrates for the same CAB. Thus, a particular CAB converts a number of prodrugs into cytotoxic form, resulting in increased antitumor activity at the tumor site.

There is often a requirement for extending the blood circulation half-lives of pharmaceutical peptides, proteins, or small molecules. Typically short half-lives—lasting minutes to hours—require not only frequent, but also high doses for therapeutic effect—often so high that initial peak doses cause side effects. Extending the half-life of such therapeutics permits lower, less frequent, and therefore potentially safer doses, which are cheaper to produce. Previously researchers have increased protein half-life by fusing them covalently to PEG, see U.S. Pat. No. 5,711,944, human blood serum albumin, see U.S. Pat. No. 5,766,883, or Fc fragments, see WO 00/24782. In addition, nonspecific targeting of drugs to human serum albumin has been accomplished by chemical coupling drugs in vivo. See U.S. Pat. No. 5,843,440. Furthermore, in the case of cancer drugs it has been proposed that high molecular weight drugs may localize in tumors due to enhanced permeability and retention. Therefore, improvement in the therapeutic index of a drug can be obtained by linking the drug to a protein or other high molecular weight polymer.

In another embodiment the present invention provides a method of treating a condition in a subject in need thereof, comprising administering to the subject a CAB with β-lactamase activity and a prodrug. In one embodiment, the subject in need thereof is a cancer patient. In another embodiment, the CAB is targeted to a CEA expressing cell, tissue, tumor or organ. In another embodiment, the prodrug is converted by the CAB into an active drug. In another embodiment, the active drug is an alkylating agent. In another embodiment, the prodrug is an anticancer nitrogen mustard prodrug. In another embodiment, the active drug is melphalan. In another embodiment, the prodrug is C-Mel. In another embodiment, the prodrug is glutaryl-C-Mel or glutaryl-C-Mel-L-Phe-NH2 (see, for example, Senter et al, U.S. Pat. No. 5,773,435, which is incorporated by reference herein, including any drawings and Kerr et al., *Bioconjugate Chem.* 9:255-59 (1998)). In another embodiment, the prodrug is vinca-cephalosporin or doxorubicin cephalosporin. See Bagshawe et al., *Current Opinion in Immunology,* 11:579-83 (1999). Other prodrug/enzyme combinations that can be used in the present invention include, but are not limited to, those found in U.S. Pat. No. 4,975,278 and Melton et al., Enzyme-Prodrug Strategies for Cancer Therapy Kluwer Academic/Plenum Publishers, New York (1999).

In a fourth aspect, the invention is drawn to a pharmaceutical composition comprising a CAB molecule. The CABs, nucleic acids encoding them and, in certain embodiments, prodrugs described herein can be incorporated into pharmaceutical compositions suitable for administration. Such compositions typically comprise the active compound and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes methods for preparing pharmaceutical compositions for modulating the expression or activity of a CAB, prodrug or nucleic acid of interest. Such methods comprise formulating a pharmaceutically acceptable carrier with an agent that modulates expression or activity of an active compound of interest. Such compositions can further include additional active agents. Thus, the invention further includes methods for preparing a pharmaceutical composition by formulating a pharmaceutically acceptable carrier with an agent that modulates expression or activity of a CAB, prodrug or nucleic acid of interest and one or more additional active compounds.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include normal saline, Water for Injection, 5% dextrose or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like) and suitable mixtures thereof. The proper fluidity can be maintained by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols such as mannitol, sorbitol, sodium chloride in the composition.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation is freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches or capsules.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate or orange flavoring.

For administration by inhalation, the compounds are delivered in the form of an aerosol spray from a pressurized container or dispenser that contains a suitable propellant, e.g., a gas such as carbon dioxide or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

In one embodiment, the formulation comprises sulfobutylether-7-beta-cyclodextrin and 2-hydroxypropyl-β-cyclodextrin, as disclosed, for example, in U.S. Pat. No. 6,216,375 and U.S. Pat. No. 6,537,988, each of which are incorporated by reference, herein, including any drawings.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved and the limitations inherent in the art of compounding such an active compound for the treatment of individuals.

Typically, the amount of CAB to be delivered to a subject will depend on a number of factors, including, for example, the route of administration, the activity of the CAB, the degree to which it is specifically targeted to the desired cells, tissues or organs of the subject, the length of time required to clear the non-specifically bound CAB from the subject, the desired therapeutic effect, the body mass of the subject, the age of the subject, the general health of the subject, the sex of the subject, the diet of the subject, the subject's immune response to the CAB, other medications or treatments being administered to the subject, the severity of the disease and the previous or future anticipated course of treatment.

For applications in which a prodrug also is administered, other factors affecting the determination of a therapeutically effective dose will include, for example, the amount of prodrug administered, the activity of the prodrug and its corresponding active drug and the side effects or toxicities of the prodrug and the active drug.

Examples of ranges of mass of CAB/mass of subject include, for example, from about 0.001 to 30 mg/kg body weight, from about 0.01 to 25 mg/kg body weight, from about 0.1 to 20 mg/kg body weight, and from about 1 to 10 mg/kg, 2 to 9 mg/kg, 3 to 8 mg/kg, 4 to 7 mg/kg, or 5 to 6 mg/kg body weight.

In a particular example, a subject is treated with a CAB in the range of between about 0.1 to 20 mg/kg body weight, one time per week for between about 1 to 10 weeks, preferably between 2 to 8 weeks, preferably between about 3 to 7 weeks and preferably for about 4, 5, or 6 weeks. It will also be appreciated that the effective dosage of CAB may increase or decrease over the course of a particular treatment, and that the treatment will continue, with or without modification, until a desired result is achieved or until the treatment is discontinued for another reason. Changes in dosage may result and become apparent from the results of diagnostic assays as described herein.

It is understood that appropriate doses of prodrugs depend upon a number of factors within the ken of the ordinarily skilled physician, veterinarian or researcher. The dose(s) of the prodrug will depend, for example, on the same factors provided above as factors affecting the effective dose of the CAB. Exemplary doses include milligram or microgram amounts of the prodrug per kilogram of subject or sample weight (e.g., about 1 microgram per kilogram to about 500 milligrams per kilogram, about 100 micrograms per kilogram to about 5 milligrams per kilogram or about 1 microgram per kilogram to about 50 micrograms per kilogram). It is furthermore understood that appropriate doses of a prodrug depend upon the potency of the prodrug with respect to the desired therapeutic effect. When one or more of these prodrugs is to be administered to an animal (e.g., a human), a physician, veterinarian or researcher may, for example, prescribe a relatively low dose at first, subsequently increasing the dose until an appropriate response is obtained.

Preferably, the CAB is administered to the subject, then the prodrug is administered. More preferably, the time between the administration of the CAB and administration of the prodrug is sufficient to allow the CAB to accumulate at its target site by binding to its target, and to allow unbound CAB to be cleared from the non-targeted portions of the subject's body. Most preferably, the ratio of target-bound CAB to unbound CAB in the subject's body will be at or near its maximum when the prodrug is administered. The time necessary after administration of the CAB to reach this point is called the clearing time. The clearing time can be determined or approximated in an experimental system by, for example, administering a detectable CAB (e.g., a radiolabeled or fluorescently labeled CAB) to a subject and simultaneously measuring the amount of enzyme at the target site and at a non-targeted control site at timed intervals. For some prodrugs, particularly those whose counterpart active drugs are highly toxic, it may be more important to ensure that the levels of unbound CAB in the subject's system are below a certain threshold. This too can be determined experimentally, as described above.

In one embodiment, administration of the prodrug is systemic. In another embodiment, administration of the prodrug is at or near the target.

The pharmaceutical compositions can be included in a container, pack, dispenser or kit together with instructions for administration.

EXAMPLES

Example 1

Construction of CAB1.10

The amino acid sequence of the scFv portion of CAB1.10 molecule was derived from murine anti-CEA monoclonal antibody (MAb) T84.66 sequence (Neumaier et. al., (1990) Cancer Research 50:2128-2134). The nucleotide sequence of the synthetic gene was designed based on *E. coli* codon usage plus a 30-aa linker connecting vL and vH domains with the following genetic configuration: vL-(GGGGS)$_6$-vH. A 968-bp DNA fragment containing the designed gene was synthesized by DNA2.0 (Menlo Park, Calif.) with flanking NcoI and EcoRV restriction sites and cloned into their pDriveCloningVector resulting in plasmid pG00229.

Plasmid pNA31.1 is a stuffer vector with an inactive BLA gene that was used to clone the scFv portion from plasmid pG00229. This was derived from plasmid pME27.1 (see WIPO publication WO03105757A2, which is incorporated by reference, herein, including any drawings) upon digestion with PstI enzyme to remove the 461-bp region containing a large part of the exigent antibody and a small part of BLA followed by self-ligation.

Upon digestion of plasmids pG00229 and pNA31.1 with NcoI and EcoRV enzymes, a 0.9-kb insert fragment and a 4.3-kb vector fragment, respectively, were gel purified. They were then ligated, followed by transformation into *E. coli* TOP10F' (Invitrogen, Carlsbad, Calif.) competent cells and selection on agar plates containing Luria-Bertani medium and 5 ppm chloramphenicol (cmp) and 0.1 ppm cephotaxim (CTX). Out of hundreds of colonies, six clones were checked for proper size and orientation of the scFv fragment by isolating plasmid DNAs and digesting them with EcoRI and SacI enzymes. With both enzymes, expected restriction patterns were observed for all six clones tested. After testing four of them for expression and binding, plasmid pHR03.1 was selected for further engineering and named as CAB1.10 molecule harboring plasmid.

Example 2

Combinatorial Consensus Mutagenesis of CAB1.10

To improve the expression of CAB1.10 protein, a combinatorial consensus mutagenesis CCM approach as described before (see U.S. patent application Ser. No. 10/688,255, filed Oct. 16, 2003 which is incorporated by reference in its entirety, including any drawings) was pursued by targeting 35 amino acid residues in the frame work regions of vL and vH domains using plasmid pHR03.1 as a template. These 35 residues (14 positions in vH and 21 positions in vL) were identified as being significantly different (<10% abundance) compared to a typical human antibody sequence. Using a modified version of Multi-site Quikchange Mutagenesis (Stratagene, CA) protocol as described before (see U.S. patent application Ser. No. 10/688,255, filed Oct. 16, 2003 which is incorporated by reference herein, including any drawings), CCM libraries HR12 and HR14 with combined primer concentrations of 2 uM and 0.4 uM, respectively, were constructed employing 35 phosphorylated primers as shown in table 1. After mutagenesis and DpnI digestion, 2.5 ul out of 25 ul PCR reaction mix was transformed into *E. coli* TOP10F' cells followed by selection on agar plates containing Luria-Bertani medium and 5 ppm chloramphenicol (cmp) and 0.1 ppm cephotaxim (CTX). 100 clones from library HR12 and 200 clones from library HR14 were initially screened for improved expression in 96-well microtiter plates as described below resulting in the selection of clone HR14.8. Sequencing of this clone revealed that it recruited A12S and R72G mutations in the vL region of the scFv fragment. Complete sequencing of the entire fusion gene of clone HR14.8 revealed no additional mutations elsewhere in the gene. This clone HR14.8 (encoded and was named) the CAB1.11 molecule.

Table. 1. Sequence of primers used for combinatorial consensus mutagenesis (CCM) of CAB1.10 protein. Primer name corresponds to the amino acid to be changed in the light (L) or heavy (H) chain, its position, and the intended mutation (mutated codon shown in upper case). So, for example, LD1Q corresponds to Asp (D) at position 1 of the light (L) chain to be changed to Gln (Q). The numbering starts with the first residue of either light or heavy chains. All primers were designed to the sense strand. The LA12S and LR68G primers incorporate A12S and R72G mutations in the CAB1.11 protein, respectively, and are shown in bold.

| Combinatorial Consensus Mutagenesis (CCM) Primers | | |
|---|---|---|
| Name | Sequence (5'-3') | Length |
| LD1Q | CcggccatggccCAGatc gtcctgacccagagcccg | 36 |
| LI2S | GccatggccgacTCTgtcc tgacccagagcccggcaag | 38 |
| LS7P | GtcctgacccagCCGccg gcaagcctggctgtttcc | 36 |
| LA9S | AcccagagcccgTCTagc ctggctgtttccctgggc | 36 |
| LA12S | CcggcaagcctgTCTgtt tccctgggccagcgtgcc | 36 |
| LM21I | CcagcgtgccactATCtc ctgcagagcgggtgagtc | 36 |
| LP43A | GaaaccgggtcagGCGcc aaaactgctgatctatcg | 36 |
| LV60D | GtccggcatcccgGACcg tttctccggtactggctc | 36 |
| LT65S | GtacgtttctccggtTCTgg ctctcgtactgattttacc | 39 |
| LG66K | CgtttctccggtactAAAtc tcgtactgattttaccctg | 39 |
| LR68G | CcggtactggctctGGTac tgattttaccctgattatc | 38 |

Combinatorial Consensus Mutagenesis (CCM) Primers

| Name | Sequence (5'-3') | Length |
|---|---|---|
| LD70T | CtggctctcgtactACCtt taccctgattatcgacccg | 38 |
| LF71A | GgctctcgtactgatGCGac cctgattatcgacccggtg | 39 |
| LI74T | ActgattttaccctgACCat cgacccggtggaagcagac | 39 |
| LD76S | TtaccctgattatcTCTccg gtggaagcagacgatgttg | 39 |
| LP77G | AccctgattatcgacGGTgt ggaagcagacgatgttgcc | 39 |
| LV83E | GtggaagcagacgatGAAgc cacctactattgccagcag | 39 |
| LT85D | GcagacgatgttgccGACta ctattgccagcagaccaac | 39 |
| LE105T | CggtactaaactgACCatca aaggcggtggtggttctgg | 39 |
| LI106V | TactaaactggagGTTaaag gcggtggtggttctggtgg | 39 |
| LK106aL | TaaactggagatcCTGggcg gtggtggttctggtggtgg | 39 |
| HE13K | GgtgcggagctcgttAAAcc gggcgcttctgtgaaactg | 39 |
| HN28T | ActgcatctggtttcACCat taaggacacctacatgcac | 39 |
| HI29F | GcatctggtttcaacTTCaa ggacacctacatgcactgg | 39 |
| HK30S | TctggtttcaacattTCTga cacctacatgcactgggtg | 39 |
| HK38R | TacatgcactgggtgAGAca acgcccggaacagggtctg | 39 |
| HR40A | CactgggtgaaacaaGCGcc ggaacagggtctggagtgg | 39 |
| HE42G | TgaaacaacgcccgGGTcag ggtctggagtggatcggtc | 39 |
| HK66R | CcaaaattccagggtAGAgc aaccatcactgctgatacc | 39 |
| HA67F | AaattccagggtaaaTTCac catcactgctgatacctcc | 39 |
| HS75K | CtgctgatacctccAAAaac actgcttacctgcagctgac | 40 |
| HT82aN | GcttacctgcagctgAACtc cctgactagcgaagacacc | 39 |
| HP94R | TttattactgcgctAGAttcg gctactatgtcagcgattac | 41 |
| HF95G | TattactgcgctccgGGTgg ctactatgtcagcgattac | 39 |
| HS108L | TggggtcagggcaccCTGgt taccgtttctagcacaccg | 39 |

Example 3

Screening of the HR14 Library

Library pHR14 was plated onto agar plates containing LB medium and 5 mg/l chloramphenicol and 0.1 mg/l cephotaxime (CTX, Sigma). Colonies from each library and parent colonies were transferred into 96 well plates containing 100 ul LB+5 ppm cmp. Plates were incubated at 30 C in a humidified box with shaking for 48-72 hrs. On the day of screening, 100 ul of B-Per reagent (PIERCE) was added into each well and shaken at room temperature for 30 min.

Target protein CEA (Biodesign International) was immobilized in a 96 well polystyrene plate by adding 100 of 5 ug/ml CEA in 50 mM NaHCO3 and the plate was incubated at 4 C overnight. The plate was then washed with PBST (PBS+0.1% Tween 20) and blocked with 300 ul/well of 1% Casein in PBS for 2 hours at room temp. On the day of screening, the plate was washed with PBST, subsequently, 80 ul/well of PBSO (PBS+0.125% Octylglucopyranoside) was first added into the plate, followed by 20 ul of diluted B-Per extracted cell culture of each well from expression plate. The plate was incubated at room temperature with gentle shaking for 1 hour. After 1 hour, the plate was washed with PBST, 200 ul of BLA substrate (nitrocefin in PBSO) was added into each well, the bound CAB molecule was measured by monitoring hydrolysis of nitrocefin at wavelength 490 nm.

Seven variants of interest from the primary screening were streaked out on LA+5 ppm cmp agar plate. Colonies from each variant were inoculated in 5 ml of LB+5 ppm cmp. The tubes were incubated at 25 C for 70 hours. The culture was pelleted and resuspended in B-Per reagent. Target protein CEA was immobilized in 96 well polystyrene plate at 5 ug/ml of 100 ul/well, the plate was then blocked with 1% Casein. On the day of screening, 80 ul/well of PBS buffer pH7.1 was added into target plate, and 20 ul/well of 2-fold serial diluted B-Per extract was added to the target plate. The plates were incubated at room temperature for 1 hour and were then washed with PBST. 200 ul of BLA substrate nitrocefin in PBSO was added into each well, the bound CAB molecules was measured by monitoring hydrolysis of nitrocefin at wavelength 490 nm. Assay results are shown in FIG. 6. The best variant, HR14.8 was chosen for further refinement.

Example 4

Epitope Removal of BLA

The i-mune assay was performed on the sequence for beta-lactamase as described (U.S. patent application Ser. No. 09/060,872, filed Apr. 15, 1998). Human population-based identification of CD4+ T cell peptide epitope determinants. (Journal of Immunological Methods, 281:95-108). Community donor peripheral blood cell samples were used. Four CD4+ T cell epitopes were identified. For each epitope peptide sequence, critical residue testing was performed. Critical residue testing included both an alanine scan of the peptide sequences, as well as specific amino acid modifications guided by functional and structural constraints. Peptide epitope sequences that reduced the level of proliferation to background levels were chosen and incorporated into a DNA construct of the beta-lactamase enzyme sequence. Modified enzyme protein variants were expressed and purified, then tested for their ability to induce cellular proliferation using human peripheral blood cells in vitro. The variant that induced the lowest level of cellular proliferation in vitro (which included BLA-epitope removing mutations at sites K21A and S324A) was selected for inclusion in CAB1.11i, as described below.

Example 5

Construction of CAB1.11i

Plasmid pHR19.2 was constructed from template HR14.8 (CAB1.11) by the Multi-site Quikchange Mutagenesis protocol (Stratagene, CA) to recruit the BLA-epitope-removing mutations K21A and S324A in the BLA protein.

Using phosphorylated primers HR016F and HR017F (HR016F: 5'-[Phosp]GATTACCCCGCTGATGGCGGC-CCAGTCTGTTCCAG-3'; HR017F: 5'-[Phosp]CTACTG-GCGGGTTTGGCGCGTACGTGGCCTTTATTCCTG-3') for recruiting mutations K21A and S324A, respectively, a multi-site Quikchange mutagenesis (Stratagene, CA) reaction was performed followed by digestion with DpnI enzyme. 2.5 ul out of 2.5 ul PCR product was transformed into $E.\ coli$ TOP10F' competent cells followed by selection of transformants on LA+Cm5+0.1 CTX plates. Plasmid DNAs from 16 clones were isolated and sequenced to confirm the recruitment of both mutations into the same plasmid. Only 2 (pHR19.2 and pHR19.15) clones were found to have both mutations in the same plasmid. Complete sequencing of the entire fusion gene of plasmid pHR19.2 revealed no additional mutations elsewhere in the gene. Finally, plasmid pHR19.2 was selected as the molecule that encodes the CAB1.11i molecule.

Example 6

Expression of CAB1.11i $E\ Coli.$ strain EB101.1 was obtained as a random isolate of strain NL106. Strain NL106 was transformed with a plasmid directing the production of an ADEPT construct and cultured in a 14 liter fermentor. Isolates from the fermetor were tested in shake flasks for production of lactamase activity, and one isolate NL106EB was chosen as host. Strain NL106 was subjected to serial shake flask cultures in defined medium and a faster growing strain, EB101.1, was isolated.

One glycerol vial containing strain EB101.1 carrying plasmid pHR19.2 was used to inoculate a flask containing 600 ml of MDM+1% Glucose media, the ingredients being shown in Table 2. The flask was incubated at 30 C and 150 rpm in an incubator shaker. The growth was monitored by sampling flask and measuring Absorbance at A550. When the broth reached a reading of approximately A550=1, the content of the flask was transferred to a seed fermenter containing the same medium. When the broth inside the seed fermenter reached a cell density of A550=7-8, then 600 ml was transferred to the production fermenter containing production medium as shown in Table 2. The production fermenter was pH controlled and fed a 60% Glucose solution. The production fermenter was allowed to run for 32-40 h until the amount of CAB1.11i reached its maximum. Typical production profiles are shown in FIG. 7, where lactamase activity is measured in in mg/ml.

TABLE 2

| MDM + 1% Glucose Medium (Flask and Seed Tank medium) | |
|---|---|
| Ingredient | Concentration in g/L |
| K2HPO4 | 13.6 |
| KH2PO4 | 13.6 |
| MgSO4*7H2O | 2 |
| Citric Acid Monohydrate | 2 |
| Ferric Ammonium Citrate | 0.3 |
| (NH4)2SO4 | 3.2 |
| Monosodium Glutamate | 3.75 or L-Serine at 2.11 g/L |
| L-Tryptophan | 0.40 |
| Trace Metal Solution | 1 ml |
| Glucose | 10 |

TABLE 3

| Production Medium | |
|---|---|
| Ingredient | Concentration in g/L |
| Calcium chloride dihydrate | 0.1818 |
| Monosodium Glutamate | 3.75 or L-Serine at 2.11 g/L |
| L-Tryptophan | 0.40 |
| Potassium phosphate monobasic | 13.63 |
| Citric Acid monohydrate | 1.818 |
| Magnesium sulfate heptahydrate | 1.82 |
| Ferric Ammonium citrate | 0.303 |
| Trace Metal Solution | 0.909 |
| Mazu DF204 | 0.78 |
| Glucose | 10 |
| Sulfuric Acid | As required to adjust pH to 7.0 |
| Ammonium Hydroxide | To control the pH at 7.0 during the fermentation |

Example 7

Purification of CAB1.11i

Preparation of high purity samples of CAB1.11i was achieved using the process outlined in FIG. 8. This process was highly efficient as the end product at each step can be input into the next step without the need for pH adjustment, buffer exchange or salt removal.

Step 1: B-PER Cell Wall Disruption and 60% Ammonium Sulfate Cut

Add 2.5 ml B-PER Reagent (in Phosphate Buffer, Pierce Biotechnology Inc., product #78266) per gram of frozen $E.\ coli$ cell paste. Benzonase Nuclease (Novagen, product #70664-3) is also added at a dilution of 1:1000 during this step to hydrolyze DNA. Mixture is stirred vigorously for 60 minutes at Room temperature.

Remove cell debris by centrifugation at 4° C. for 20 minutes and 12,000 rpm. Discard pellet.

Add 390 grams solid ammonium sulfate (Sigma, product #A-2939) per 1 liter of supernatant to achieve 60% saturation at 25° C. Stir 40 minutes at room temperature. Recover precipitated protein by centrifugation at 4° C. for 20 minutes and 12,000 rpm. Solubilize pellet into TEA Buffer (20 mM triethanolamine/0.5M NaCl, pH 7). The crude protein solution should be centrifuged at 14,000 rpm and filtered through a 0.22 μm filter prior to loading onto the PBA column.

Step 2: CAB1.11i Protein Capture Via PBA Affinity Chromatography

A 30 ml PBA column (m-Aminophenylboronic acid immobilized onto agarose beads from Sigma, product #A-8530) was 'cleaned' with 150 ml borate buffer (0.5M borate/0.5M NaCl, pH7), and equilibrated with 150 ml TEA buffer prior to loading crude protein. After loading sample, the column was washed with 150 ml TEA buffer (5 column volumes).

After loading the sample, the column is washed with 150 ml TEA buffer.

CAB protein is eluted with 150 ml borate buffer and collected in 10 ml fractions.

Eluted fractions are assayed for β-lactamase using the nitrocefin plate assay, described, for example, in WO 0247717A2.

Step 3: Removal of CAB Degradation Products Via Hydrophobic Charge Induction

Chromatography 5 ml of CAB protein eluted from the PBA column loaded directly onto a 7 ml MEP HyperCel column (produced by BioSepra) equilibrated in phosphate buffered saline (PBS). After loading the sample, the column was washed with 10 column volumes of PBS. CAB protein was eluted from the resin using a 10 column volume gradient elution with 75 mM sodium citrate buffer at pH 5.2.

Eluted fractions assayed for β-lactamase using the nitrocefin plate assay, as set forth above.

Step 4: Size Exclusion Chromatography for Obtaining Pure Monomer CAB1.11i 5 ml of concentrated CAB protein was loaded onto a Superdex 75 preparative grade column (Amersham Biosciences, product #17-1070-01) equilibrated with PBS. Proteins were separated with a flow rate of 2 ml/min of PBS and collected in 5 ml fractions.

Step 5: Removal of Endotoxin Via Detoxi-Gel 1-4 ml of concentrated CAB protein was loaded onto a 10 ml Detoxi-Gel (immobilized polymixin-B, Pierce, product #20339) column equilibrated with PBS. The sample was left bound to the resin for 2.5 hours before eluting with PBS. Collect 20 1 ml fractions.

Assay individual fractions for β-lactamase using the nitrocefin plate assay and for endotoxin using the BioWhittaker QCL-1000 Chromogenic Endpoint LAL assay. Calculated endotoxin units per mg of CAB protein. The maximum limit for in vivo murine studies is 5 units/mg and, for PBMC immunogenicity assays, 0.2 units/mg.

FIG. 9 shows an SDS PAGE analysis of CAB1.11i protein of the protein that was purified by the above described procedure.

Example 8

PBMC Assay of CAB1.11i

In order to test the potential immunogenicity of the CAB1.11i protein, the protein was tested in the PBMC proliferation assay. Community donor PBMC samples were purchased from the Stanford University Blood Center (Palo Alto, Calif.) or from BloodSource (Sacramento). Each sample was tested for common human bloodborne pathogens. PBMC were isolated from the buffy coat samples by differential centrifugation using Lymphocyte Separation Media (Gibco). PBMC were adjusted to $4 \times 10^6$ per ml in 5% heat-inactivated human AB serum-containing RPMI 1640. Cultures were seeded at 2 ml per well in a 24 well plate (Costar). Purified proteins were added at 20 ug/ml final concentration, and the bulk cultures were incubated at 37° C., 5% $CO_2$ for 5 days. Five days was selected after testing cultures at 4, 5, 6 and 7 days. The optimum responses were seen at 5 days for most proteins, with the exception of robust secondary responses to proteins such as tetanus toxoid that often peaked at day 4. On day 5 the bulk cultures were resuspended and 100 ul aliquots of each culture were replicately plated into a 96 well plate. From 4 to 12 replicates were performed for each bulk culture. Tritiated thymidine was added at 0.25 uCi per well, and the replicates were cultured for 6 hours. Cultures were harvested to glass filtermats (Wallac) and the samples were counted in a scintillation counter (Wallac TriBeta). The CPM for each bulk culture were averaged. A control well with no added protein provided background CPM for each donor. A stimulation index for each test was calculated by dividing the experimental CPM by the control. An SI of 1.0 indicated that there was no proliferation above the background level. All purified protein samples were prepared in house. All proteins were tested for endotoxin using a commercially available kit (Pierce). All samples were adjusted to 1-2 mg/ml protein in PBS and were filter sterilized.

Thirty-six community donor samples were tested with the CAB1.11i protein. The average stimulation index was 1.06+/−0.25. This value is not different from background proliferation (SI=1.0). None of the thirty-six donors mounted a proliferative response greater than 1.99, the cut-off value for a positive response. This is in contrast to previously collected data for the unmodified beta-lactamase protein, which showed an average stimulation index of 2.35+/−3.50, and a 27% response rate in 26 community donor samples. The proliferation results for the CAB1.11i are lower than the stimulation index results for the beta-lactamase (p=0.03). No donors mounted a stimulation index of 1.99 or greater when tested with the CAB1.11i protein, as compared to the 27% responses to the beta-lactamase protein. Finally, the PBMC data for staphylokinase, a protein known to cause immune responses in community donors, was an average stimulation index was 3.68+/−2.16, with a 70% response rate. The data for CAB1.11i is highly different from the staphylokinase data. These results are interpreted to suggest that the CAB1.11i protein is comparatively non-immunogenic when tested in this human cell based, in vitro proliferation assay.

Example 9

Binding of CAB1.11i to CEA

Purified CEA (Biodesign International) was immobilized onto 96 well Costar High binding plates by incubation with a 5 ug/ml solution in 50 mM NaHCO3 buffer at pH 9.6. A blocking step using casein to prevent non-specific binding was performed. Samples of purified CAB1.11i protein were pre-tested for their BLA enzymatic activity against nitrocefin substrate to determine the specific activity. CAB1.11i was diluted in 10 mM PBS buffer pH 7.1 to 30,000 units/ml concentration. A 2 fold serial dilution was prepared in the same buffer and 100 ul aliquots were added to the wells (8 samples: 3000, 1500, 750, 375, 187, 94, 47, 24 units). The protein was allowed to bind to the plates at ambient temperature for 1.5 h. The wells were extensively washed with PBS buffer containing Tween-20. The amount of CAB1.11i protein bound to the plates was determined my monitoring the amount of BLA remaining on the wells. The nitrocefin substrate (200 ul/well of 0.1 mg/ml solution) was added to the wells and the product of the reaction was recorded by measuring the Absorbance at 490 nm over a 20 min incubation period (ambient temperature). The $V_{max}$ was determined for each protein concentration, and a binding curve was generated by plotted protein bound versus protein added, to determine the $K_d$ apparent for the material.

Binding curves are plotted in FIG. 10A. CAB1.11i concentration was determined from measured BLA activity using a pre-determined conversion factor.

For apparent $t_{1/2}$ determinations, the CAB1.11i protein bound following the above-described procedure was sequentially allowed to wash off by incubation of the wells in PBS buffer pH 7.1 at ambient temperature. At prescribed times (0, 40, 80, 120 min) the buffer on the wells was removed and replaced with a nitrocefin substrate solution, and the BLA activity was determined as described above. The enzyme activity remaining bound (relative to time zero) was calculated, and the percent BLA activity bound (remaining) was plotted versus time to determine the 50% retention time.

The results can be seen in FIG. 10B.

Example 10

CAB1.11i Circular Dichroism

Circular-dichroism (CD) spectra were collected on an Aviv 215 spectrophotometer equipped with a 5-position thermo-electric cell holder supplied by Aviv. Buffer conditions were phosphate buffered saline at pH7.4 and protein concentration was 1 µM. Data was collected from 265 to 195 nm every 1 nm with a 1 nm bandwith in a 0.1 cm path length cell at 25° C. Data was collected for 5 seconds at each wavelength and three replicate spectra were averaged. The CD signal was converted to mean residue ellipticity (MRE). The CD Spectrum of CAB1.11i is indicative of a folded protein with both alpha helix and beta strand secondary structural components.

Example 11

Pharmacokinetics and Tissue Distribution of CAB1.11i in Xenograft Mouse Model of Human Colorectal Cancer Ncr athymic nude mice), 18-22 g, approximately 6-8 weeks of age, were implanted subcutaneously with approximately 2 million tumor-derived LS174T human colorectal cancer cells. When tumors reached approximately >250 mm³, 12 animals were administered a single IV bolus injection of CAB1.11i (1 mg/kg) via the tail vein and 3 animals were untreated to provide control tissues. Three animals were anaesthetized and sacrificed at 0, 6, 12, 24 and 48 hr. Liver, kidney and tumor were harvested from each animal, snap frozen in liquid nitrogen and stored at approximately −70° C. until analysis. Blood was collected via cardiac puncture onto EDTA. Blood samples were centrifuged to separate plasma that was then stored at approximately −70° C. until analysis.

Tissue samples were homogenized on ice in PBS with 15 ug/mL aprotinin (2 mL buffer:gram tissue). Homogenate was mixed with B-PER (1:1) (from Pierce) and centrifuged. CAB1.11i concentrations in the tissue supernatant and plasma samples were determined by measuring BLA activity using a nitrocefin assay.

The results of this experiment indicated that CAB1.11i was rapidly eliminated from plasma, liver and kidney and localized to the TLS174T tumor (FIG. 12). High tumor to blood ratio of CAB1.11i concentrations were sustained and achieved (FIG. 13).

Example 12

Efficacy of CAB1.11i in a Xenograft Mouse Model of Human Colorectal Cancer

Ncr athymic nude mice, 18-22 g, approximately 6-8 weeks of age, were implanted subcutaneously with approximately 2 million tumor-derived LS174T human colorectal cancer cells (TLS174T). LS174T cells were obtained from ATCC, passaged through mice and re-isolated to generate TL174T. When tumors reach approximately >250 mm³, ten mice each were administered nothing or CAB1.11i (1 or 0.25 mg/kg followed by administration of, Glutaryl-C-Mel, GCR-2141, shown for example, in U.S. Pat. No. 5,773,435, as (150 mg/kg) 24 hours after CAB administration. All drugs were administered by IV bolus injections via the tail vein. Tumors were measured twice weekly.

The results of this study demonstrated that CAB1.11i at both 1 m/kg and 0.25 mg/kg doses in combination with the prodrug GCR-2141 at 150 mg/kg was active in a mouse model of human colorectal cancer (see FIG. 14).

Example 13

Construction of a Ropo2 Antibody

An antibody specific for BLA, Ropo2, was constructed as described. BLA was suspended in PBS Buffer (1 mg/ml), emulsified by mixing with an equal volume of Complete Freund's Adjuvant (Total volume of 0.6 ml) and injected into three to four subcutantous dorsal sites for primary immunization. Subsequent immunizations were performed using Incomplete Freund's Adjuvant at a dose of 200 ug/rabbit. For collection, animals were bled from the articular artery. The blood was allowed to clot and serum was collected by centrifugation. Serum was stored at −20 C.

Example 14

Tumor Panel IHCs to Assess Distribution of Target Antigen and Binding Specificity Frozen tissue samples used in this study were obtained from Ardais' BIGR® Library (Ardais). Genencor provided preparations of CABs as well as the rabbit polyclonal anti-BLA antibody, Ropo2. IHC analysis was used and as a positive control, a cytokeratin antibody (Dako Cytomation) was used. Please see Table 4.

TABLE 4

| Antibody | Source | Concentration | Species |
|---|---|---|---|
| CAB 1.2i with 15-mer | | 1.4 mg/ml | N/A |
| CAB 1.11i | | 1.0 mg/ml | N/A |
| CAB 1.2i with 30-mer | | 3.0 mg/ml | N/A |
| CAB 1.14i | | 1.8 mg/ml | N/A |
| Ropo 2 αBLA | | 436 µg/ml | Rabbit |
| Cytokeratin | Dako Cytomation | 0.2 mg/ml | Mouse |

Frozen samples were removed at temperatures between −80° C. and placed in −20° C. for 2 hours. The cryostat was set at −20° C. and section samples were cut at 5 µm thickness. Sections were placed on Plus Slides and stored in a microscope slide box on dry ice while sectioning. Sections were air dried at room temperature for 30 minutes. Sections were placed in acetone at room temperature for 10 minutes. Sections were rinsed in Wash Buffer (Dako Cytomation, Code #S3006, Lot #044312) 2-3×5 min at room temperature.

IHC was performed on a Dako autostainer. Antibodies were diluted in Antibody Diluent (Dako Cytomation, Code #S0809, Lot #123113) to the following concentrations: CAB antibodies to 0.2 µg/ml and Ropo 2 antibody to 0.1 µg/ml. Samples were incubated with approximately ~200 µl Peroxidase Block for 5 minutes at room temperature. Antibodies were rinsed with wash buffer for 2×5 minutes. Samples were incubated with approximately ~200 µl Protein Block (Dako Cytomation, Code #X0909, Lot #103183) for 10 minutes. ~200 µl CAB antibody was added for 30 minutes at room temperature. Samples were washed with Wash Buffer 2×5 minutes. Approximately ~200 µl Ropo 2 antibody was added and incubation occurred for 30 minutes at room temperature. Samples were rinsed with Wash Buffer for 2×5 minutes. ~200 µl Secondary Antibody from Detection System was added and incubated for 30 minutes. The samples were rinsed with wash buffer for 2×5 minutes. Samples were incubated in ~200 µl Chromagen (DAB+ provided in Detection System (Envision+ System, HRP (DAB) Rabbit)—Dako Cytomation, Code #K4011, Lot #11367)) for 5 minutes. The samples were washed with distilled water for 5 minutes. The samples were counterstained with Hematoxylin (Richard Allen, Code #7211, Lot #35053), which provides a blue nuclear stain, for 30 seconds. The samples were rinsed for 5 minutes. Samples were dipped twice in a Bluing Reagent (Richard Allen, Code #7301, Lot #19540). Samples were rinsed with distilled water for 5 minutes. Samples were dehydrated in 95% Ethanol 2×2 minutes, 100% Ethanol 2×2 minutes and cleared in Xylene. Samples were mounted with Medium (Richard Allen, Code #4111, Lot #18071), and a coverslips were added.

In this IHC study, the four CAB antibodies CAB 1.2i, 15-mer linker, CAB 1.2i, 30-mer linker, CAB 1.11i and Cab 1.14i were analyzed against a tissue panel consisting of 5 lung, 3 colon, and 5 pancreatic tumor samples.

FIG. 15 shows the full results of the study. The first column details the case diagnosis; the second column details the tissue of origin and site of finding; the fourth column shows staining with the anti-human cytokeratin AE1/AE3, columns five through eight show staining against the four antibodies, CAB 1.2i with a 15-mer linker, CAB 1.2i with a 30-mer linker, CAB 1.11i and CAB 1.14i.

The four antibodies showed robust immunostaining (intensity of 2-3+) in all of the tumor samples tested and were very similar if not identical in their staining patterns. All samples with the exception of one, CI000005496-FF5, demonstrated staining in greater than 75% of tumor cells present. Minimal, pale (1-2+) staining, which is sometimes seen with frozen tissue sections, was also observed in stromal cells, including fibroblasts and occasional mixed inflammatory cells. Necrotic cells and intra-alveolar macrophages (seen in samples of lung tissue) consistently showed positive staining.

Adjacent normal tissue present in the samples was largely negative, with no positive staining seen in normal lung or pancreatic tissue. Normal liver tissue seen in sample CI0000008475, a case of colon cancer metastatic to the liver, showed pale staining that was limited to the sinusoidal regions with 3 of the antibodies (CAB 1.2i 15-mer linker, CAB 1.11i, and CAB 1.2i, 30-mer linker). The fourth antibody (CAB 1.14i) showed stronger, more diffuse staining of 90% of normal liver parenchyma.

In comparing the staining characteristics of the four antibodies tested, there was only minimal variability observed. Of the four antibodies tested, CAB 1.14i appeared to show slightly more background staining.

The cytokeratin antibody, which was used on selected samples to ensure that the tissue antigens were properly preserved, showed strong positive staining of epithelial cells. There was no staining seen in the 'no-primary antibody' controls.

Example 15

Pharmacokinetics and Tissue Distribution of GC-Mel Administered at Various Intervals Following CAB 1.11i in LS174T Xenograft Bearing Nude Mice We assessed the tumor retention characteristics of CAB1.11i by monitoring the formation of Mel from the administration of GC-Mel. Dosing solutions were prepared on the day of dosing, within 60 minutes of administration.

The concentration of the formulation of GC-Mel in bicarbonate/sucrose was based on average rat weight, the desired volume of administration and a dose level of 150 mg/kg. GC-Mel was weighed out and, based on this weight, the appropriate amount of sodium bicarbonate to neutralize all 3 equivalents of the three carboxylic acid sites of GC-Mel was determined. Vehicle was prepared in the required volume by adding the precalculated sodium bicarbonate solution in 5% aqueous sucrose. Vehicle was prechilled at 4° C. Cold vehicle was added to the GC-Mel powder and the mixture was vortexed and sonicated to achieve speedy dissolution.

Female Ncr athymic nude mice (n=250), having a body weight of 18-22 g and being approximately 6-8 weeks of age, were obtained from Taconic (Germantown, N.Y.).

The animals were be implanted subcutaneously on the flank with $2 \times 10^6$ TLS174T cells, a human colorectal tumor line, in 100 µl of phosphate buffered saline. Beginning approximately one week after tumor cell implant, tumors were measured every 3 to 4 days. When the tumors reached approximately 100-250 mm$^3$, 156 animals were selected based on tumor size and randomized into 7 groups, resulting in a non-significant difference in the mean tumor size between groups at the start of the experiment.

Mice were warmed with a heating lamp and heating pad, placed in a restrainer and the test compounds were administered by bolus intravenous injection via the tail vein. For the blood sampling, all mice were anesthetized by isoflurane inhalation at the time of sample collection. Blood was collected by cardiac puncture into tubes containing EDTA and placed on ice. Tubes were centrifuged at 4000 RPM for two minutes. The plasma fraction was removed into a pre-labeled microfuge tube and placed on dry ice or liquid nitrogen. Sample concentrations were determined.

Tissue samples were rinsed 1× in phosphate buffered saline to remove blood. The samples were snap frozen using liquid nitrogen or dry ice. Tissue samples were stored at –70° C. prior to analysis.

TLS174T is a cell line established from LS174T by passaging the parental cell line in-vivo. TLS174T cell line was originally purchased from ATCC (Manassas, Va.). TLS174T cells routinely test negative for mycoplasma contamination (MycoAlert Mycoplasma Detection Kit, Cambrex). TLS174T cells were used for the in-vivo studies between passage 3 and 15 and were in log phase growth at the time of harvest for implanting. The cells were maintained in 87% Dulbecco's Modified Eagle's Medium (Cellgro (Herndon, Va.))/Hams F12 (Cellgro (Herndon, Va.)) (1:1) containing 10% fetal calf serum (HyClone (Salt Lake City, Utah)), 1% sodium pyruvate (final concentration=1 mM) (Cellgro (Herndon, Va.)), 1% non-essential amino acids (Cellgro (Herndon, Va.)), 1% L-glutamine (final concentration=2 mM) (Cellgro (Herndon, Va.)). The passage number of the cells used for this study was 5. The level of CEA expression was checked by FACS analysis.

For implantation, TLS174T were plated at 4-5E4 cells/cm$^2$ (2-2.5E7 cells/500 cm$^2$ (Nunc Triple Flask or 0.9-1.1E7 cells/ 225 cm$^2$). This is equivalent to a $\frac{1}{12}$ split. Cells were expected to reach approximately 85-90% confluency in 72 hrs with approximate cell recovery of 1.3-1.5E8 cells per TF or 5.9-6.8E7 cells per T-225.

The study design is outlined in Table 5. Animals in Group 1 (n=3) served as the non-treated control group. Animals in Group 2 (n=42) were dosed intravenously with CAB 1.11i (1 mg/kg). Animals in group 3 (n=3) were dosed intravenously with Mel (150 mg/kg). Animals in group 4 (n=27) were dosed intravenously with CAB 1.11i (1 mg/kg). After 24 hr, the animals were dosed intravenously with 150 mg/kg GC-Mel in sucrose/NaHCO$_3$ buffer. The animals in Group 5 (n=27) were dosed intravenously with CAB 1.11i (1 mg/kg). After 48 hr, the animals were dosed intravenously with 150 mg/kg GC-Mel in sucrose/NaHCO$_3$ buffer. The animals in Group 6 (n=27) were dosed intravenously with CAB 1.11i (1 mg/kg). After 72 hr, the animals were dosed intravenously with 150 mg/kg GC-Mel in sucrose/NaHCO$_3$ buffer. The animals in Group 7 (n=27) were dosed intravenously with CAB 1.11i (1 mg/kg). After 96 hr, the animals were dosed intravenously with 150 mg/kg GC-Mel in sucrose/NaHCO$_3$ buffer.

TABLE 5

| Group | N/sex | CAB 1.11i (1 mg/kg) | GC-Mel (150 mg/kg) | Time of GC-Mel admin. |
|---|---|---|---|---|
| 1 | 3/F | − | − | — |
| 2 | 42/F | + | − | — |
| 3 | 3/F | − | + | — |
| 4 | 27/F | + | + | 24 |
| 5 | 27/F | + | + | 48 |
| 6 | 27/F | + | + | 72 |
| 7 | 27/F | + | + | 96 |

[1]Time of administration, post CAB 1.11i administration
[2]Collected post GC-Mel administration Blood samples for plasma were taken from the animals in Group 1 at time 0. Blood samples were taken from the animals in Group 2 at 0.033, 0.083, 0.25, 0.5, 1, 2, 3, 4, 6, 8, 24, 48, 72 and 96 hr after CAB 1.11i injection. Blood samples for plasma were taken from the animals in Group 3 at 0.033 hr. Blood samples for plasma were taken from the animals in Groups 4-7; 0.033, 0.083, 0.25, 0.5, 1, 2, 3, 4 and 6 hr after GC-Mel injection.

Tissue (tumor, kidney, liver) samples were taken from the animals in group 1 at zero time. Tissue (tumor, kidney, liver) samples were taken from the animals in group 2 at 0.033, 0.083, 0.25, 0.5, 1, 2, 3, 4, 6, 8, 24, 48, 72 and 96 hr after CAB 1.11i injection. No tissue samples were collected from group 3. Tissue (tumor, kidney) samples were taken from the animals in groups 4-7 at 0.033, 0.083, 0.25, 0.5, 1, 2, 3, 4 and 6 hr. The samples were snap frozen using liquid nitrogen or dry ice and methanol. The tissue samples were stored at −70° C. prior to analysis.

The results are shown in FIGS. 16-18. As can be seen from the results, plasma Mel decreased to near background (concomitant) levels at 96 hrs. Also, efficacy demonstrated with 24 hour intervals suggest similar anti-tumor activity likely at later intervals for GC-Mel with reduced plasma concentration. It is important that exposure to Mel is increased at the tumor site and decreased at locations not affected by tumor (to minimize potential side affects). This may require that CAB 1.11i be given sufficient time in advance of the prodrug so that CAB can localize to the tumor and unbound CAB can clear. From our data, it appears that some interval, such as 24 hours, is essential. Accordingly, dosing interval may be very important, even critical.

Example 16

Antitumor Activity of CAB 1.2i, 15-Mer, CAB 1.2i 30-Mer CAB 1.14i and Cab 1.11i Followed by Administration of GC-Mel in the Tumor-Derived TLS174T Tumor Bearing Female Athymic Mice Dosing solutions were prepared on the day of dosing, within 60 minutes of administration. An aliquot of each formulated dosing solution was retained and stored at −70° C. prior to analysis. CABs were analyzed for protein concentration and BLA activity. GC-Mel and Mel were analyzed for compound concentration.

Bulk GC-Mel was weighed and dissolved in 3.0 eq of 1.0 M NaHCO$_3$. Solutions were mixed well by vortex and diluted with 5% aqueous sucrose solution to 30 mg/mL final concentration, as above. Animals received 100 μL formulated dosing solution.

Bulk Mel was weighed and dissolved in 20% DMSO in acidified PBS (pH 4.0) to 2 mg/mL final concentration. Animals received 100 μL each formulated dosing solution.

One hundred and fifty female Ncr athymic mice, 18-22 g, approximately 6-8 weeks, from Taconic Labs were implanted with TLS174T human colorectal tumors. One hundred animals were selected for dose administration based on tumor size and growth rate.

Study design is outlined in Table 6. Mice were implanted with TLS174T cells (Study Day 0) and when tumors reached approximately ≥250 mm$^3$, 100 animals were selected based on tumor size and growth rate and sorted into 10 groups resulting in similar mean tumor size between groups. Ten mice each were administered CAB 1.2i, 15-mer, CAB 1.14i or CAB 1.11i (1 or 0.25 mg/kg) or CAB 1.2i, 30-mer (0.25 mg/ml) followed by GC-Mel (150 mg/kg) 24 hours after CAB administration. Ten mice each were administered vehicle, Mel (10 mg/kg) or GC-Mel (150 mg/kg).

TABLE 6

| Group | N/Sex | Test Article | Dose (mg/kg) | GC-Mel Dose[2] (mg/kg) | Observations |
|---|---|---|---|---|---|
| 1 | 10/F | Vehicle[1] | — | — | Body weight: weekly Cage side observations: daily Tumor Measurements: twice weekly |
| 2 | 10/F | Mel | 10 | — | |
| 3 | 10/F | CAB 1.2i | 0.25 | 150 | |
| 4 | 10/F | — | — | 150 | |
| 5 | 10/F | CAB 1.2i, 15-mer | 0.25 | 150 | |
| 6 | 10/F | CAB 1.2i, 15-mer | 1 | 150 | |
| 7 | 10/F | CAB 1.11i | 0.25 | 150 | |
| 8 | 10/F | CAB 1.11i | 1 | 150 | |
| 9 | 10/F | CAB 1.14i | 0.25 | 150 | |
| 10 | 10/F | CAB 1.14i | 1 | 150 | |

[1]Five animals will be administered 1:10 dilutions in PBS of 20 mM sodium citrate, 150 mM NaCl, pH 6.0 and five animals will be administered 20% DMSO in acidified PBS (pH 4.0)
[2]GC-Mel administered 24 hours post-CAB administration.

One hundred and fifty female mice were implanted with TLS174T cells by subcutaneous injection suspended in DMEM at 2×10$^7$ cells/mL. Animals were anesthetized by isofluorane inhalation, and cells were implanted by subcutaneous injection of 100 μL cell suspension (approximately 2×10$^6$ cells/mouse). The day of implantation was designated as Study Day 0.

After tumor implantation, animals were observed daily at minimum and moribund or distressed animals were euthanized. Tumors were measured twice weekly, and body weights were recorded weekly.

When tumors reached ≥250 mm³, animals were assigned to groups. Mice were weighed on the day of dosing, and doses were based on the average weight of all animals. Mice were warmed with a heating lamp and heating pad and placed in a restrainer. The tail was wiped with 70% alcohol and doses were administered by bolus intravenous injection via the tail vein.

Treatment groups whose average tumor volume exceeded 1500 mm³ were euthanized, and individual animals whose tumor was excessively large and/or necrotic were euthanized. A treatment group was euthanized if fewer than 6 animals remain in the study, except to monitor individual animals that achieved a complete response for tumor regrowth.

On Day 45, remaining mice were euthanized by $CO_2$ inhalation and underwent necropsy. Abnormal tissues or organs were formalin fixed for histopathology. Tumors were collected from all animals into formalin for histopathology.

Results can be seen in FIG. 19. The CABs, followed by administration of prodrug, showed a decrease in tumor volume. However, the same group, showed some weight loss.

Example 17

Immunogenicity of wt BLA, GCR-8886 and CAB1.2i After IV or IP Administration to Normal Mice CAB1.11i and CAB1.2i were diluted in PBS to 200 ug/ml. For the i.p. group (group 5), CAB1.11i was diluted in a 1:1 solution of alum to PBS (resulting concentration=200 ug/ml) and vortexed rapidly for 10 minutes. The mixture was left at 2-8° C. for a minimum of 15 minutes. The mixture was revortexed 1 minute prior to injection into mice. The dosing solution was stored on ice prior to administration.

Wt BLA was diluted in PBS to 400 ug/ml. For the i.p. group, group 4, wt BLA was diluted in a 1:1 solution of alum to a PBS with resulting concentration=200 ug/ml and vortexed rapidly for 10 minutes. The mixture was left at 2-8° C. for a minimum of 15 minutes. The mixture was then revortexed 1 minute prior to injection into mice. The solution was stored on ice prior to administration.

Study design is outlined in Table 7. Female CB6F1/J mice were used for each group. Mice undergoing i.v. injections were placed under a heating lamp for approximately 3 minutes to vasodilate the tail vein, and then placed in a mouse restrainer for the i.v. injection. On days 1, 8 and 15, three mice of each strain each were administered CAB1.2i (20 ug), CAB1.11i (20 ug), or wt BLA (20 ug) intravenously, or wt BLA (20 ug) or CAB1.11i (20 ug) complexed with alum administered by an i.p. injection. Dose concentrations and volumes are outlined in Table 8. Dose concentrations were formulated based on a 100 uL injection/mouse.

TABLE 7

Study Design

| Group | Number Animals | Test Article | ROA | Dose (ug) | # of Doses | Days of administration |
|---|---|---|---|---|---|---|
| 1 | 3 | wt BLA | iv | 20 | 3 | 1, 8 and 15 |
| 2 | 3 | CAB1.11i | iv | 20 | | |
| 3 | 3 | CAB1.2i | iv | 20 | | |
| 4 | 3 | wt BLA in alum | ip | 20 | | |
| 5 | 3 | CAB1.11i in Alum | ip | 20 | | |

TABLE 8

Dose Concentrations

| Group | Test Article | Dose (ug) | Concentration (ug/mL) |
|---|---|---|---|
| 1 | wt BLA | 20 | 200 |
| 2 | CAB1.11i | 20 | 200 |
| 3 | CAB1.2i | 20 | 200 |
| 4 | wt BLA in alum | 20 | 200 |
| 5 | CAB1.11i in alum | 20 | 200 |

After CAB1.2i or CAB1.11i injection, animals were observed twice weekly and moribund or distressed animals were euthanized. On Days 8, 13 and 20, mice were anesthetized using isofluorane and blood was collected into microtainer serum tubes by tail bleed. On Day 20, mice were euthanized for collection of spleens and lymph nodes.

Cells were recovered for T-cell proliferation assays (see, for example, U.S. Pat. No. 6,835,550, which is incorporated by reference, herein, including any drawings). Results are shown in FIG. 20, where the x-axis shows the type of conjugate administered, and the y-axis shows the anti-test article measured in IgG1 antibodies ng/ml. As can be seen from the Figure, wt BLA administered IP showed the greatest antibody response.

Example 18

Dose-Ranging Efficacy Study in LS174t Xenograft Bearing NCR Nude Mice

Materials were prepared as above.

Female Ncr athymic nude mice (n=100) having a body weight of 18-22 g and being approximately 6-8 weeks of age, were obtained from Taconic (Germantown, N.Y.). The animals (n=100) were implanted, study day 0, subcutaneously on the flank with $5 \times 10^6$ LS174T cells in 100 µl of phosphate buffered saline. Beginning approximately one week after tumor cell implant, the tumors were measured every 3 to 4 days. When the tumors reached approximately 100-250 mm³, 93 animals were selected based on tumor size and randomized into 9 groups, resulting in a non-significant difference in the mean tumor size between groups at the start of the experiment.

Mice were warmed with a heating lamp and heating pad, placed in a restrainer and the test compounds were administered by bolus intravenous injection via the tail vein. For blood sampling, all mice were anesthetized by isoflurane inhalation at the time of sample collection. Blood was collected by cardiac puncture into tubes containing EDTA and placed on ice. Tubes were centrifuged at 4000 RPM for two minutes. The plasma fraction was removed into a pre-labeled microfuge tube and placed on dry ice or liquid nitrogen. All plasma samples were stored at −70° C. prior to analysis.

LS174T cells were originally purchased from ATCC (Manassas, Va.). The cells were routinely tested negative for mycoplasma contamination (MycoAlert Mycoplasma Detection Kit, Cambrex). LS174T cells were used for the in vivo studies between passage 2 and 15 and were in log phase growth at the time of harvest for implanting. Cells were maintained in 87% Dulbecco's Modified Eagle's Medium (Cellgro (Herndon, Va.))/Hams F12 (Cellgro (Herndon, Va.)) (1:1) containing 10% fetal calf serum (HyClone (Salt Lake City, Utah)), 1% sodium pyruvate (final concentration=1 mM) (Cellgro (Herndon, Va.)), 1% non-essential amino acids (Cellgro (Herndon, Va.)), 1% L-glutamine (final concentration=2 mM) (Cellgro (Herndon, Va.)). Passage number of the cells used for this study was 2. CEA expression was checked by FACS analysis.

Study design is outlined in Table 9. The animals in Group 3 (n=10) served as the non-treated control group. The animals in Group 1 and 2 (n=3) were dosed intravenously with CAB1.11i (1 mg/kg). After 72 and 96 hours, the animals were dosed intravenously with 50 mg/kg GC-Mel in sucrose/NaHCO$_3$ buffer respectively. The animals in Group 3 (n=10) served as the non-treated control group. The animals in Group 4 (n=10) were dosed intravenously with CAB1.11i (1 mg/kg). After 72 hr, the animals were dosed intravenously with vehicle of GC-Mel-sucrose/NaHCO$_3$ buffer. The animals in Group 5 (n=10) were dosed intravenously with CAB1.11i (1 mg/kg). After 72 hr, the animals were dosed intravenously with 150 mg/kg GC-Mel in sucrose/NaHCO$_3$ buffer. The animals in Group 6 (n=10) were dosed intravenously with CAB1.11i (1 mg/kg). After 72 hours, the animals were dosed intravenously with 300 mg/kg GC-Mel in sucrose/NaHCO$_3$ buffer. The animals in Group 7 (n=10) were dosed intravenously with CAB 1.11i (1 mg/kg). After 72 hr, the animals were dosed intravenously with 600 mg/kg GC-Mel in sucrose/NaHCO$_3$ buffer. The animals in Group 8 (n=10) were dosed intravenously with CAB 1.11i (1 mg/kg). After 72 hr, the animals were dosed intravenously with 900 mg/kg GC-Mel in sucrose/NaHCO$_3$ buffer. The animals in Group 9 (n=10) were dosed intravenously with CAB1.11i (1 mg/kg). After 96 hr, the animals were dosed intravenously with 900 mg/kg GC-Mel in sucrose/NaHCO$_3$ buffer. The animals in Group 10 (n=10) were dosed intravenously with CAB1.11i (5 mg/kg). After 96 hr, the animals were dosed intravenously with 900 mg/kg GC-Mel in sucrose/NaHCO$_3$ buffer. The animals in Group 11 (n=10) were dosed intravenously with CAB1.11i (5 mg/kg).

TABLE 9

| Group | N/sex Tumor (Size, mm$^3$) | CAB1.11i (mg/kg) | GC-Mel (mg/kg) | Time of GC-Mel administration (Post CAB 1.11i) | PK plasma sampling for GC-Mel, Mel: (Hr) | Tumor sampling for GC-Mel, Mel: (Hr) |
|---|---|---|---|---|---|---|
| 1 | 3/F (55-130) | 1 | 50 | 72 | 0.25 | 0.25 |
| 2 | 3/F (55-130) | 1 | 50 | 96 | 0.25 | 0.25 |
| 3 | 10/F (55-130) | none | none | none | N/A | N/A |
| 4 | 10/F (55-130) | 1 | 0 vehicle | 72 | N/A | N/A |
| 5 | 10/F (55-130) | 1 | 150 | 72 | N/A | N/A |
| 6 | 10/F (55-130) | 1 | 300 | 72 | N/A | N/A |
| 7 | 10/F (55-130) | 1 | 600 | 72 | N/A | N/A |
| 8 | 10/F (55-130) | 1 | 900 | 72 | N/A | N/A |
| 9 | 10/F (55-130) | 1 | 900 | 96 | N/A | N/A |
| 10 | 10/F (55-130) | 5 | 900 | 96 | N/A | N/A |
| 11 | 10/F (55-130) | 5 | 0 | 96 | N/A | N/A |

Blood and tissue samples were taken from the animals in Groups 1 and 2 at time 0.25 hours after GC-Mel injection for pharmacokinetic analysis done by LC/MS/MS. Tumor and body weight of the animals were measured periodically.

Results are shown in FIG. 21. The Figure shows cytotoxic activity of CAB1.11i/GC-Mel. The x-axis shows days, and the y-axis shows the average tumor volume as measured in mm.$^3$ From the Figure, one can see tumor volume shrank in all lines, except those of the control and species treated with CAB1.11i, alone.

Example 19

Dose-Ranging Toxicity Profile of GC-Mel Administered 72 or 96 Hours After CAB1.11i in NCR Nude Mice Bearing TLS174T Xenograft Tumors Materials were prepared as above.

The concentration of the GC-Mel formulation in bicarbonate/sucrose was based on average rat weight, the desired volume of administration and the dose level of 150 mg/kg. GC-Mel was weighed out. Based on GC-Mel weight, the appropriate amount of sodium bicarbonate to neutralize all 3 equivalents of the three carboxylic acid sites of GC-Mel was determined. Vehicle was prepared in the required volume by adding the precalculated sodium bicarbonate solution in 5% aqueous sucrose. 5% sucrose was used since bicarbonate serves as neutralizing agent and does not persist in the above formulation of GC-Mel. Vehicle was prechilled at 4° C. Cold vehicle was added to the GC-Mel powder and the mixture and vortexed and sonicated, if needed, to achieve speedy dissolution.

Female Ncr athymic nude mice (n=250), having a body weight of 18-22 g and being approximately 6-8 weeks of age, were obtained from Taconic (Germantown, N.Y.). Animals (n=150) were implanted on study day 0, subcutaneously on the flank with 10×10$^6$ TLS174T cells in 100 μl of phosphate buffered saline. Approximately one week after tumor cell implant, tumors were measured every 3 to 4 days. When the tumors reached approximately 100-250 mm$^3$, 108 animals were selected based on tumor size and randomized into 22 groups, resulting in a non-significant difference in the mean tumor size between groups at the start of the experiment.

Mice were warmed with a heating lamp and heating pad, placed in a restrainer and test compounds were administered by bolus intravenous injection via tail vein. For the blood sampling, all mice were anesthetized by isoflurane inhalation at the time of sample collection. Blood was collected by cardiac puncture into tubes containing EDTA and placed on ice. Tubes were centrifuged at 4000 RPM for two minutes. Plasma fraction was removed into a pre-labeled microfuge tube and placed on dry ice or liquid nitrogen. All plasma samples were stored at −70° C. prior to analysis.

For implantation, TLS174T were plated at 4-5E4 cells/cm$^2$ (2-2.5E7 cells/500 cm$^2$ (Nunc Triple Flask or 0.9-1.1E7 cells/225 cm$^2$). This is equivalent to a $\frac{1}{12}$ split. Cells reach approximately 85-90% confluency in 72 hrs with approximate cell recovery of 1.3-1.5E8 cells per TF or 5.9-6.8E7 cells per T-225.

Study design is outlined in Table 10. The animals in Group 1 (n=5) served as the non-treated control group. The animals in Group 2 (n=5) were dosed intravenously with PBS—CAB 1.11i vehicle followed with sucrose/NaHCO$_3$ buffer—GC-Mel vehicle. The animals in Group 3 (n=5) were dosed intravenously with Cab1.11 i (1 mg/kg). The animals in Groups 4 (n=3), 7 and 13 (n=5) were dosed intravenously with CAB1.11i (1 mg/kg). After 72 hr (Groups 4 and 7) and after 96 hr (Group 13), the animals were dosed intravenously with 150 mg/kg GC-Mel in sucrose/NaHCO$_3$ buffer. The animals in Group 5 (n=5) were dosed intravenously with CAB1.11i (1 mg/kg). After 72 hr the animals were dosed intravenously with GC-Mel vehicle sucrose/NaHCO$_3$ buffer. The animals in Groups 6 and 12 (n=5) were dosed intravenously with CAB1.11i (1 mg/kg). After 72 hr (Group 6) and after 96 hr (Group 12), the animals were dosed intravenously with 75 mg/kg GC-Mel in sucrose/NaHCO$_3$ buffer. The animals in Groups 8 and 14 (n=5) were dosed intravenously with CAB1.11i (1 mg/kg). After 72 hr (Group 8), and after 96 hr (Group 14), the animals were dosed intravenously with 300 mg/kg GC-Mel in sucrose/NaHCO$_3$ buffer. The animals in Groups 9 and 15 (n=5) were dosed intravenously with CAB1.11i (1 mg/kg). After 72 hr (Groups 9) and after 96 hr (Groups 15), the animals were dosed intravenously with 450 mg/kg GC-Mel in sucrose/NaHCO$_3$ buffer. The animals in Groups 10 and 16 (n=5) were dosed intravenously with CAB1.11i (1 mg/kg). After 72 hr (Group 10) and after 96 hr (Group 16), the animals were dosed intravenously with 600 mg/kg GC-Mel in sucrose/NaHCO$_3$ buffer. The animals in Groups 11 and 17, (n=5) were dosed intravenously with CAB1.11i (1 mg/kg). After 72 hr (Group 11) and after 96 hr (Group 17), the animals were dosed intravenously with 750 mg/kg GC-Mel in sucrose/NaHCO$_3$ buffer. The animals in Groups 18, 19, 20 and 21 (n=5) were dosed only with GC-Mel at 300 mg/mL, 450 mg/mL, 600 mg/mL and 750 mg/mL, respectively.

TABLE 11

| Group | N/sex | CAB1.11i (mg/kg) | GC-Mel (mg/kg) | Time of GC-Mel administration (Post GCR-8886) (Hr) | PK Sampling: GC-Mel/Mel (plasma) (Hr) | Tissue Sampling: (tumor) (Hr) | Body weights |
|---|---|---|---|---|---|---|---|
| 1 | 5/F | none | none | N/A | N/A | N/A | 2x weekly |
| 2 | 5/F | Vehicle | Vehicle | N/A | N/A | N/A | 2x weekly |
| 3 | 5/F | 1 | 0 | N/A | N/A | 2 | N/A |
| 4 | 3/F | 1 | 150 | 72 | 0.033 | N/A | N/A |
| 5 | 5/F | 1 | 0 vehicle | 72 | N/A | N/A | 2x weekly |
| 6 | 5/F | 1 | 75 | 72 | N/A | N/A | 2x weekly |
| 7 | 5/F | 1 | 150 | 72 | N/A | N/A | 2x weekly |
| 8 | 5/F | 1 | 300 | 72 | N/A | N/A | 2x weekly |
| 9 | 5/F | 1 | 450 | 72 | N/A | N/A | 2x weekly |
| 10 | 5/F | 1 | 600 | 72 | N/A | N/A | 2x weekly |
| 11 | 5/F | 1 | 750 | 72 | N/A | N/A | 2x weekly |
| 12 | 5F | 1 | 75 | 96 | N/A | N/A | 2x weekly |
| 13 | 5/F | 1 | 150 | 96 | N/A | N/A | 2x weekly |
| 14 | 5/F | 1 | 300 | 96 | N/A | N/A | 2x weekly |
| 15 | 5/F | 1 | 450 | 96 | N/A | N/A | 2x weekly |
| 16 | 5/F | 1 | 600 | 96 | N/A | N/A | 2x weekly |
| 17 | 5/F | 1 | 750 | 96 | N/A | N/A | 2x weekly |
| 18 | 5/F | 0 | 300 | N/A | N/A | N/A | 2x weekly |
| 19 | 5/F | 0 | 450 | N/A | N/A | N/A | 2x weekly |
| 20 | 5/F | 0 | 600 | N/A | N/A | N/A | 2x weekly |
| 21 | 5/F | 0 | 750 | N/A | N/A | N/A | 2x weekly |

The results can be seen in FIG. 22 Average body weight loss was less than 20% for all dose groups, indicating that dose limiting toxicity was not achieved using these dose regimens.

Example 20

Pharmacokinetics of CAB1.11i Following Intravenous Bolus Administration to Sprague-Dawley Rats Materials were formulated as described above.

Male and female Sprague-Dawley rats were assigned to the study based on catheter patency and acceptable health as determined by an attending veterinarian. Animals were placed into three groups of four animals per sex per group. For Group 1, each animal received CAB1.11i (0.25 mg/mL) as an intravenous bolus injection into the femoral vein cannula at a target dose level of 0.25 mg/kg, and at a dose volume of 1 mL/kg. For Group 2, each animal received CAB1.11i (0.25 mg/mL) as an intravenous bolus injection into the femoral vein cannula at a target dose level of 1 mg/kg, and at a dose volume of 4 mL/kg. For Group 3, each animal received CAB1.11i (1.36 mg/mL) as an intravenous bolus injection into the femoral vein cannula at a target dose level of 5 mg/kg and at a dose volume of 3.68 mL/kg.

Following each dose, the femoral vein catheter was flushed with 0.5 mL of saline and tied-off to prevent re-access. All doses were administered without incident except for animal number 16 (Group 2), number 20 (Group 3) and number 24

(Group 3). Due to insufficient dose solution, animal numbers 16 and 20 were not dosed and animal number 24 did not receive its full dose volume.

Throughout dosing and sample collection, the animals were observed for any clinically relevant abnormalities, and the following were noted (Table 10):

TABLE 10

| Group No. | Animal No. | Time Post-Dose | Clinical Observation |
|---|---|---|---|
| 2 | 11 | 2 minutes | Animal exhibited mild soft feces. |
| 3 | 8 | 30 min | Animal exhibited mild soft feces. |

Blood samples (0.25 mL; EDTA anticoagulant) were collected via the jugular vein cannula prior to each dose and at 0.033, 0.083, 0.25, 0.5, 1, 2, 4, 8, 12, 24, 48, 72 and 96 hours following intravenous administration. Blood samples were placed on ice and were centrifuged at 1000×g (5° C.) to harvest plasma within 15 minutes of blood collection.

Figure 24B:
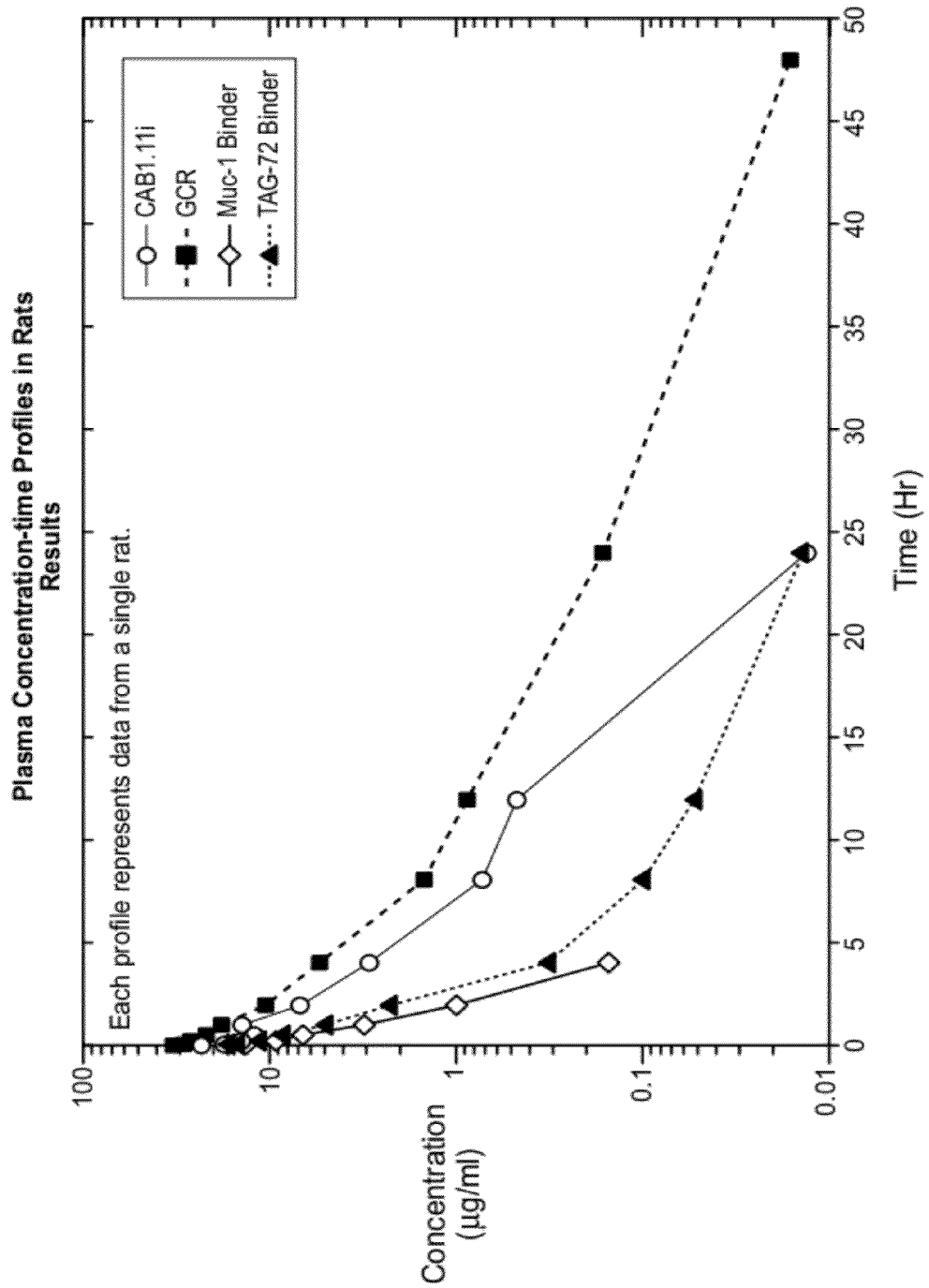
FIG. 24B shows the plasma concentration-time profiles in rats, the x-axis showing time, in hours, and the y-axis shows concentration. The inset shows symbols for two representative CAB1.11i (circles and squares, 15% dimer and monomer, respectively)

The results can be seen in FIG. 23. This study was compromised by dimer, but does indicate that PK is dose proportional in the animal model. FIG. 24 shows that dimer content effects disposition-low dimer (squares) CAB1.11i is eliminated more rapidly than high dimmer (circles).

Example 21

Pharmacokinetics of CAB 1.11i Following Intravenous Bolus Administration of Sprague-Dawley Rats 0.0049 g Mel was prepared as set forth above. Mel was combined with 4.91 mL (4.87 g) of DMSO vehicle (20% DMSO, 80% aqueous containing 0.15 M NaCl and $5 \times 10^{-4}$ M HCl). The formulation was mixed by inversion and vortexed for a total of 8 minutes to produce a clear colorless solution with a target concentration of 1 mg/mL for intravenous administration. No dosing was required for Group 1.

Nineteen male Sprague-Dawley rats were assigned to the study based on catheter patency and acceptable health as determined by an attending veterinarian. The animals were placed into five groups of three animals per group and one group of four animals. The animals in Group 1 received no dose administration and were used to provide blank plasma and urine to be used for sample analysis. The animals in Group 2 received Mel as an intravenous bolus injection into the femoral vein catheter at a target dose level of 2 mg/kg and at a dose volume of 2 mL/kg. The animals in Group 3 received a TAG-72 binding construct as an intravenous bolus injection into the femoral vein catheter at a target dose level of 1 mg/kg and at a dose volume of 1 mL/kg. The animals in Group 4 received a Muc-1 binding construct as an intravenous bolus injection into the femoral vein catheter at a target dose level of 1 mg/kg and at a dose volume of 1 mL/kg. The animals in Group 5 received CAB1.11i as an intravenous bolus injection into the femoral vein catheter at a target dose level of 1 mg/kg and at a dose volume of 1.02 mL/kg. The animals in Group 6 received a similar CAB1.11i as an intravenous bolus injection into the femoral vein catheter at a target dose level of 1 mg/kg and at a dose volume of 1 mL/kg.

Following dosing, the femoral dosing catheter was flushed with 0.5 mL of saline and tied-off to prevent re-access. Throughout dosing and sample collection, the animals were observed for any clinically relevant abnormalities, and the following were noted (Table 12):

Following dosing, each animal was transferred to a separate Nalge rodent metabolism cage for collection of voided urine. Urine was collected on cold packs from each animal in Group 1 for 48 hours. Voided urine was collected on dry ice from each animal in Groups 2-6 at 0-24 and 24-48 hours following dose administration. The urine collected from the Group 1 animals was pooled, then divided into two approximately equal aliquots.

Blood samples were collected from each animal via the jugular vein catheter into tubes containing EDTA anticoagulant. For Group 1, the maximum obtainable volume was collected from each animal following the 48-hour urine collection. For Groups 2-6, blood samples (0.3 mL each, but the maximum obtainable volume at last the timepoint) were collected via the jugular vein catheter prior to each dose and at 0.033, 0.083, 0.25, 0.5, 1, 2, 4, 8, 12, 24, and 48 hours following intravenous administration. Additional blood samples were collected from the animals in Groups 3-6 at 72 and 96 hours post-dose. Due to a technician error, a terminal blood sample was collected from animal number 8 (Group 3) at 48 hours post-dose. As a result, the 72 and 96-hour post-dose blood samples were not collected from this animal. Blood samples were placed on ice until centrifuged at about 5° C. to isolate plasma within 30 minutes after blood collection. Each plasma sample from the Group 1 animals was divided into two approximately equal aliquots. A single plasma aliquot was prepared from each blood sample collected from the animals in Groups 2-6.

Following terminal blood collection and euthanasia, the bone marrow (both femurs), kidneys and liver were collected from the Group 2 animals only. The weights of the tissues were not recorded.

The results are shown in FIG. 24.

Example 22

The Effect of CEA Administration on the Pharmacokinetics of CAB1.11i Following Intravenous Administration to Cynomolgus Monkeys Materials were prepared as set forth above.

Aliquots of the CAB1.11i formulations for Groups 1-3 were diluted in PBS and the absorbance of each diluted sample was determined in triplicate at 280 nm using a spectrophotometer. For Group 5, CEA stock solution (0.862 mg/mL, 325 uL) was combined with PBS (325 uL) to produce a total volume of 650 uL at a concentration of 0.431 mg/mL. The diluted CEA (0.508 mL, 0.431 mg/mL) was added to a tube containing 8.75 mL of CAB1.11i at 1 mg/mL concentration. The CEA was added to CAB1.11i 30 minutes prior to dosing and kept at room temperature. For Group 6, 2.54 mL of stock CEA (0.862 mg/mL) was added to a tube containing 8.75 mL of CAB1.11i at 1 mg/mL concentration. The CEA was added to CAB1.11i 30 minutes prior to scheduled dosing and kept at room temperature. For the Day 8 dosing of the Group 3 animals, additional pre-formulated 5 mg/mL CAB1.11i was used. A dose formulation sample (0.1 mL each) was collected from this dose solution. The dose formulation sample and residual dose formulation were stored at 5±3° C.

Six male and four female cynomolgus monkeys were selected and placed into six groups of two animals per group. One male and one female were assigned to Groups 1, 2, 4 and 6, and two males were assigned to Group 5. One treatment naïve male and one treatment naïve female cynomolgus monkey were assigned to Group 3. All animals were equipped with a chronic venous catheter and subcutaneous vascular access port (VAP) to facilitate blood collection. The animals were assigned to the study based on acceptable health as determined by a staff veterinarian following a pre-study health evaluation. The pre-study health evaluation included serum chemistry and hematology evaluations as well as a physical exam. Animals had previously been acclimated to primate chairs and rope/pole and collar restraint. Animals were restrained in primate chairs for dosing and for up to the first two hours of blood collection before being returned to their individual cages. Fasting of the animals before or after dosing was not required.

Prior to dosing, a temporary percutaneous catheter was placed in a saphenous or cephalic vein of each animal. All doses were administered via a percutaneous venous catheter. The animals in Group 1 received a bolus administration of prepared CAB1.11i at a target dose level of 0.25 mg/kg and at a dose volume of 1 mL/kg. The animals in Group 2 received a bolus administration of prepared CAB1.11i at a target dose level of 1 mg/kg and at a dose volume of 1 mL/kg. On Day 1 and Day 8, the animals in Group 3 received a bolus administration of prepared CAB1.11i at a target dose level of 5 mg/kg and at a dose volume of 1 mL/kg. The animals in Group 4 received a bolus administration of prepared CEA at a target dose level of 0.25 mg/kg and at a dose volume of 0.290 mL/kg. The animals in Group 5 received a bolus administration of the prepared CAB1.11i/CEA mixture at target dose levels of 1 mg/kg CAB1.11i and 0.025 mg/kg CEA and at a dose volume of 1.058 mL/kg. The animals in Group 6 received a bolus administration of the prepared CAB1.11i/CEA mixture at target dose levels of 1 mg/kg CAB1.11i and 0.25 mg/kg CEA and at a dose volume of 1.290 mL/kg.

Immediately following each intravenous dose, the dosing catheter was flushed with approximately 3 mL saline prior to removal. Each dosing syringe was weighed before and after dosing to gravimetrically determine the quantity of formulation administered. Dose administration data including pre-dose animal body weights are presented in Table 13.

Blood samples (5 mL or 1 mL; EDTA anticoagulant) were collected via the chronic venous catheter and subcutaneous access port or by venipuncture of a femoral vein if the catheter became impatent. Blood samples were placed on ice for no longer than 30 minutes prior to processing. The blood samples were centrifuged at 3500 RPM for 10 minutes at 5° C. to harvest plasma. Each plasma sample was split into two approximately equal aliquots, transferred to separate polypropylene tubes, and stored at $-70\pm10°$ C. For Group 3, the plasma from all 5 mL pre-dose samples (Day 1 pre-dose, Day 8 pre-dose, and Day 22) were split into 3 approximately equal aliquots, transferred to separate polypropylene tubes, and stored at $-70\pm10°$ C. Voided urine was collected from each animal.

The results, shown in FIG. 25 and FIG. 26, show that CAB1.11i serum concentration profiles were similar after 2 doses, separated by one week, indicating that significant levels of neutralizing antibodies had not formed within this time frame. The elimination phase of CAB1.11i was similar in the presence or absence of CEA.

Having described the preferred embodiments of the present invention, it will appear to those ordinarily skilled in the art that various modifications may be made to the disclosed embodiments, and that such modifications are intended to be within the scope of the present invention.

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments, are exemplary, and are not intended as limitations on the scope of the invention. It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limi-

TABLE 13

| | | | | | | | Treatment | | | | |
|---|---|---|---|---|---|---|---|---|---|---|---|
| Group Number | Number of Animals Male | Number of Animals Female | Test Article | Dose Level (mg/kg) | Dose Conc. (mg/mL) | Dose Volume (mL/kg) | Total Dose combined (mL/kg) | Dose Regimen | Dose Vehicle | Dose Route | Flush |
| 1 | 1 | 1 | CAB1.11i | 0.25 | 0.25 | 1 | 1 | Day 1 | PBS + 25 mM Phosphate (Na & | Intravenous bolus | 3 mL saline |
| 2 | 1 | 1 | CAB1.11i | 1 | 1 | 1 | 1 | Day 1 | K)/145 mM NaCl, 5% (w/v) sucrose, pH 7.0 | Intravenous bolus | 3 mL saline |
| 3 | 1 (naïve) | 1 | CAB1.11i | 5 | 5 | 1 | 1 | Day 1 and Day 8 | 25 mM Phosphate (Na & K)/145 mM NaCl, 5% (w/v) sucrose, pH 7.0 | Intravenous bolus | 3 mL saline |
| 4 | 1 | 1 | CEA | 0.25 | 0.862 | 0.290 | 0.290 | Day 1 | PBS | Intravenous bolus | 3 mL saline |
| 5 | 2 | 0 | CAB1.11i CEA | 1 0.025 | 1 0.431 | 1 0.058 | 1.058 | Day 1 | PBS + 25 mM Phosphate (Na & | Intravenous bolus | 3 mL saline |
| 6 | 2 | 0 | CAB1.11i CEA | 1 0.25 | 1 0.862 | 1 0.290 | 1.290 | Day 1 | K)/145 mM NaCl, 5% (w/v) sucrose, pH 7.0 | Intravenous bolus | 3 mL saline | tation or limitations that is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

The invention claimed is:

1. A method of treating a cancer that expresses carcinoembryonic antigen (CEA) or that has CEA bound to itself or that has CEA located in its vicinity, the method comprising administering to a subject in need of thereof a CAB molecule and a prodrug that is a substrate of the CAB molecule,
   wherein the CAB molecule comprises an unmodified amino acid sequence, the unmodified amino acid sequence being set forth in SEQ ID NO:2, or
   wherein the CAB molecule comprises an amino acid sequence modified from the amino acid sequence set forth in SEQ ID NO:2, the modification comprising at least one of the following positions: 12, 72, 283 or 586, wherein position numbering is with respect to SEQ ID NO:2.

2. The method according to claim 1, wherein the subject is a mammal.

3. The method according to claim 1, wherein the subject is a human.

4. The method according to claim 1, wherein the CAB molecule comprises an unmodified amino acid sequence, the unmodified amino acid sequence being set forth in SEQ ID NO:2.

5. The method according to claim 1, wherein the CAB molecule comprises an amino acid sequence modified from the amino acid sequence set forth in SEQ ID NO:2, the modification comprising at least one of the following positions: 12, 72, 283 or 586, wherein position numbering is with respect to SEQ ID NO:2.

6. The method according to claim 1, wherein the CAB molecule comprises an amino acid sequence set forth in SEQ ID NO:5.

7. The method according to claim 1, wherein the CAB molecule comprises an amino acid sequence set forth in SEQ ID NO:7.

8. The method according to claim 1, wherein the CAB molecule and the prodrug are administered at different times.

9. The method according to claim 8, wherein the CAB molecule is administered before the prodrug so that the time between them comprises a dosing interval.

10. The method according to claim 9, wherein the dosing interval is between about 1 day and about 14 days.

11. The method according to claim 10, wherein the dosing interval is between about 3 days and about 10 days.

12. The method according to claim 11, wherein the dosing interval is between about 7 days and between about 10 days.

13. The method according to claim 11, wherein the dosing interval is between about 3 days and about 7 days.

14. The method according to claim 13, wherein the dosing interval is about 3 days.

15. The method according to claim 13, wherein the dosing interval is about 4 days.

16. The method according to claim 13, wherein the dosing interval is about 5 days.

17. The method according to claim 13, wherein the dosing interval is about 6 days.

18. The method according to claim 13, wherein the dosing interval is about 7 days.

19. The method according to claim 1, wherein the prodrug is a Melphalan-based prodrug.

20. The method according to claim 19, wherein the Melphalan-based prodrug is GC-Mel.

\* \* \* \* \*